(12) United States Patent
Blanco et al.

(10) Patent No.: US 10,766,855 B2
(45) Date of Patent: Sep. 8, 2020

(54) HYDROXAMATE TRITERPENOID DERIVATIVES

(71) Applicant: VIVACELL BIOTECHNOLOGY ESPANA S.L., Cordova (ES)

(72) Inventors: Eduardo Munoz Blanco, Cordova (ES); Alberto Minassi, Novara (IT); Maria Luz Bellido Cabello De Alba, Cordova (ES); Giovanni Appendino, Turin (IT)

(73) Assignee: VIVACELL BIOTECHNOLOGY ESPAÑA, S.L., Cordova (ES)

( * ) Notice: Subject to any disclaimer, the term of this patent is extended or adjusted under 35 U.S.C. 154(b) by 0 days.

(21) Appl. No.: 16/099,800

(22) PCT Filed: Oct. 3, 2017

(86) PCT No.: PCT/EP2017/075042
§ 371 (c)(1),
(2) Date: Nov. 8, 2018

(87) PCT Pub. No.: WO2018/069086
PCT Pub. Date: Apr. 19, 2018

(65) Prior Publication Data
US 2019/0367447 A1 Dec. 5, 2019

(30) Foreign Application Priority Data
Oct. 13, 2016 (EP) .................................. 16193684

(51) Int. Cl.
| A61P 25/28 | (2006.01) |
| A61P 3/06 | (2006.01) |
| C07C 259/08 | (2006.01) |
| C07D 231/56 | (2006.01) |
| C07D 261/20 | (2006.01) |
| A61K 31/575 | (2006.01) |

(52) U.S. Cl.
CPC .............. *C07C 259/08* (2013.01); *A61P 3/06* (2018.01); *A61P 25/28* (2018.01); *C07D 231/56* (2013.01); *C07D 261/20* (2013.01)

(58) Field of Classification Search
CPC .. C07C 259/08; C07D 261/20; C07D 231/56; A61P 3/06; A61P 25/28; A61P 9/10; C07J 63/008; C07J 63/00
See application file for complete search history.

(56) References Cited

U.S. PATENT DOCUMENTS
8,324,264 B1 12/2012 Eldridge et al.
2012/0238767 A1 9/2012 Jiang et al.

FOREIGN PATENT DOCUMENTS
WO 2009146216 A2 12/2009

OTHER PUBLICATIONS

Wiemann et al. Bioorg. Med. Chem. Lett. 2016, 26, 907-909. (Year: 2015).*
Karna et al. Mol. Cell. Biochem. 2010, 340, 15-20. (Year: 2010).*
Wang et al., "Nutrition and metabolism in hepatocellular carcinoma," Redox. Rep. Apr. 2, 1996,(2): 89-96.
Semeza et al., "Transcriptional regulation of genes encoding glycolytic enzymes by hypoxia-inducible factor 1," J. Biol. Chem. Sep. 23, 1994 269(38): 23757-63.
Eltzschig et al., "Targeting hypoxia signalling for the treatment of ischaemic and inflammatory diseases," Nat. Rev. Drug Discov. Nov. 2014; 13(11): 852-69.
Rabinowitz, et al., "Inhibition of Hypoxia-Inducible Factor Prolyl Hydroxylase Domain Oxygen Sensors: Tricking the Body into Mounting Orchestrated Survival and Repair Responses," J. Med. Chem. Dec. 12, 2013; 56(23): 9369-4025.
Ratcliffe et al., "HIF-1 and HIF-2: working alone or together in hypoxia?" Clin. Invest. Apr. 2007; 117(4): 862-5.
(Continued)

*Primary Examiner* — Amanda L. Aguirre
(74) *Attorney, Agent, or Firm* — Tristan A. Fuierer; Olive Law Group, PLLC

(57) ABSTRACT

Triterpenoid derivatives and compositions comprising said triterpenoids derivatives of Formula (I) are described, wherein R=—C(O)NHOH. Said triterpenoids and compositions show capacity to bind PHD2, stabilize HIF-1α and HIF-2α proteins, activate the HIF pathway in different cell types, induce angiogenesis in human endothelial vascular cell, show neuroprotective activity in vitro and in vivo, antidiabetic activity and reduce the levels of lipids in vivo, and increase the plasma levels of Erythropoietin in vivo. The triterpenoid derivatives described act also in a selective manner and do not induce Nrf2 activation, NF-κB inhibition, STAT3 inhibition, and TGR5 activation, which are known activities of the natural triterpenoid precursors. Said triterpenoid derivatives are useful in the treatment of conditions and diseases which are responsive to HIF activation such as stroke, cerebral palsy, traumatic injuries and neurodegenerative diseases; and also IBD, myocardial ischaemia-reperfusion injury, acute lung injury, diabetic and chronic wounds, organ transplantation, acute kidney injury or arterial diseases.

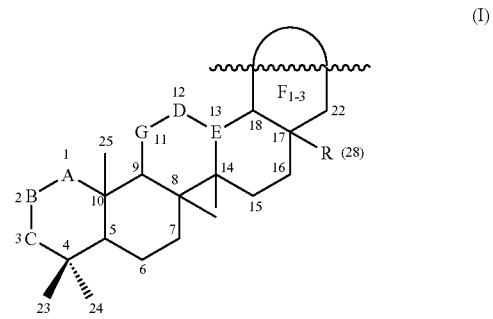

(I)

17 Claims, 17 Drawing Sheets
Specification includes a Sequence Listing.

(56) References Cited

OTHER PUBLICATIONS

Bruick, McKnight et al., "A conserved family of prolyl-4-hydroxylases that modify HIF," Science Nov. 9, 2001; 294(5545): 1337-40.
Takeda et al., "Essential Role for Prolyl Hydroxylase Domain Protein 2 in Oxygen Homeostasis of the Adult Vascular System," Circulation Aug. 14, 2007; 116(7): 774-81.
Karhausen et al., "Epithelial hypoxia-inducible factor-1 is protective in murine experimental colitis," J. Clin. Invest. Oct. 2004; 114(8): 1098-1106.
Aragonés et al., "Oxygen sensors at the crossroad of metabolism," Cell Metab. Jan. 2009; 9(1): 11-22.
Wu et al., The protective role of hypoxic preconditioning in CNS, Anoxia, Dr. Pamela Padilla (Ed.), 2012, InTech, DOI 10.5772/27621.
Speer et al., "Hypoxia-inducible factor prolyl hydroxylases as targets for neuroprotection by "antioxidant" metal chelators: From ferroptosis to stroke," Free Radio. Biol. Med. Sep. 2013; 62:26-36.
Sun et al., "Glucocorticoid Protection of Oligodendrocytes against Excitotoxin Involving Hypoxia-Inducible Factor-1 in a Cell-Type-Specific Manner," Neurosci. Jul. 14, 2010; 30(28): 9621-30.
Peng et al., "The efficacy of erythropoietin in treating experimental traumatic brain injury: a systematic review of controlled trials in animal models," J. Neurosurg. Sep. 2014: 121(3): 653-64.
Ehrenreich et al., "Recombinant human erythropoietin in the treatment of acute ischemic stroke," Stroke Dec. 2009; 40 (12): e647-56.
Li et al., Ann. "Dowling P. Beneficial effect of erythropoietin on experimental allergic encephalomyelitis," Ann Neurol. 2004;56:767-777. doi: 10.1002/ana.20274.
Yang et al., "Induction of hypoxia inducible factor-1 attenuates metabolic insults induced by 3-nitropropionic acid in rat C6 glioma cells," J. Neurochem. May 2005; 93: 513-25, doi.10.1111/j.1471-4159.2005.03032.x.
Sheng et al., "Synthesis, biology and clinical significance of pentacyclic triterpenes: a multi-target approach to prevention and treatment of metabolic and vascular diseases," Nat. Prod. Rep. Mar. 2011 ; 28(3) : 543-93.
Yadav et al ; "Targeting inflammatory pathways by triterpenoids for prevention and treatment of cancer," Toxins (Basel) Oct. 2010 ; 2(10) : 2428-66.
Sato et al., "Anti-hyperglycemic activity of a TGR5 agonist isolated from Olea europaea," Biochem. Biophys. Res. Comm. Nov. 3, 2007; 362(4): 793-8.
Wiemann et al., "Betulinic acid derived hydroxamates and betulin derived carbamates are interesting scaffolds for the synthesis of novel cytotoxic compounds," Eur. J. Med. Chem. Dec. 1, 2015 ; 106 : 194-210.
Wiemann et al., "Targeting cancer cells with oleanolic and ursolic acid derived hydroxamates," Bioorg. Med. Chem. Lett. Feb. 1, 2016 ; 26(3) : 907-9.
Dasgupta et al., "AECHL-1, a novel triterpenoid, targets tumor neo-vasculature and impairs the endothelial cell cytoskeleton," Angiogenesis Jul. 2015; 18(3): 283-99, doi: 10.1007/s10456-015-9466-5.
Jin et al., "Triterpenoids and diarylheptanoids from alnus hirsuta inhibit HIF-1 in ags cells," Arch Pharm Res. Apr. 2007 ; 30(4) : 412-418.
Dai et al., "Sodwanone and Yardenone Triterpenes from a South African Species of the Marine Sponge Axinella Inhibit Hypoxia-Inducible Factor-1 (HIF-1) Activation in Both Breast and Prostate Tumor Cells," J. Nat. Prod. Dec. 2006 ; 69 (12) : 1715-1720.
Potente et al., "Basic and therapeutic aspects of angiogenesis," Cell Sep. 16, 2011 ; 146(6) : 873-887.
Rahtu-Korpela et al., "HIF prolyl 4-hydroxylase-2 inhibition improves glucose and lipid metabolism and protects against obesity and metabolic dysfunction," Diabetes Oct. 2014 ; 63(10) : 3324-3333.
Ech-Chahad et al., "An expeditious hydroxyamidation of carboxylic acids," Tetrahedron Letters 2005; 46: 5113-5115.
Morris et al., "AutoDock4 and AutoDockTools4: Automated docking with selective receptor flexibility," J. Comp. Chem. Dec. 2009 ; 30(16) : 2785-2791.
Trott and Olson, "AutoDock Vina: improving the speed and accuracy of docking with a new scoring function, efficient optimization and multithreading," J. Comp. Chem. Jan. 30, 2010; 31(2):455-461.
Wolf LK, "New Software and Websites for the Chemical Enterprise," Chem. & Eng. News 2009, 87.
Ewa Kama et al., "Betulinic acid inhibits the expression of hypoxia-inducible factor 1 alpha and vascular endothelial growth factor in human endometrial adenocarcinoma cells," Mol. and Cell. Biochem. Feb. 21, 2010; 340(1-2): 15-20.
Rongxin et al., "Oleanolic acid enhances the radiosensitivity of tumor cells under mimetic hypoxia through the reduction in intracellular GSH content and HIF-1 alpha expression," Oncology Rep. Mar. 2014; 31(5): 2399-2406.
Te-Chun Hsia et al., "Maslinic Acid Induces Mitochondrial Apoptosis and Suppresses HIF-1 alpha Expression in A549 Lung Cancer Cells under Normoxic and Hypoxic Conditions," Molecules Nov. 2014; 19(12): 19892-19906.
So Young Park et al.; "Maslinic Acid Induces Mitochondrial Apoptosis and Suppresses HIF-1 alpha Expression in A549 in Lung Cancer Cells under Normoxic and Hypoxic Condition," British J. of Nutrition Apr. 2012; 109(2): 210-222.
Shan Jian-Zhen et al., "Ursolic acid sensitized colon cancer cells to chemotherapy under hypoxia by inhibiting MDR1 through HIF-1 alpha," Int Biomed & Biotech J Sep. 2016; 17(9): 672-682.
F. Jung et al.; "Hypoxic Regulation of Inducible Bitric Oxide ynthase via Hypoxia Inducible Factor-1 in Cardiac Myocytes," Circ. Res. Feb. 2000 ; 86(3) : 319-325.
International Search Report, dated Jan. 30, 2018.

* cited by examiner

1A

1B

2A

2B

3A

3B

3C

12A

12B

12C

12D

13A

13B

13C

HYDROXAMATE TRITERPENOID DERIVATIVES

CROSS-REFERENCE TO RELATED APPLICATIONS

This application claims priority to and the benefit of European Patent Application No. 16193684.4, filed Oct. 13, 2016 and International Patent Application No. PCT/EP2017/075042, filed Oct. 3, 2017, the disclosure of which is incorporated herein by.

FIELD OF THE INVENTION

The present invention relates to novel triterpenoid derivatives, and the synthesis of said compounds. Furthermore, the present invention relates to their use as a medicament and in therapy, particularly as stabilizer of HIF-1α and HIF-2α proteins, activator of the HIF-1 pathway and in treating diseases and conditions responsive to HIF-1α and HIF-2 stabilization. This invention also provides pharmaceutical compositions comprising said compounds and method of treating diseases with said compounds.

BACKGROUND OF THE INVENTION

Mammalian cells need to maintain proper oxygen homeostasis in order to execute their aerobic metabolism and energy generation. Since the discovery of the hypoxia-inducible factor (HIF)-1, signaling mechanisms underlying oxygen-sensing by HIF transcription factors have been extensively studied in biological contexts (Wang et al., Redox Rep. 1996 April; 2(2):89-96). HIFs, composed of oxygen-labile α and constitutively expressed β subunits, drive the transcription of numerous genes involved in diverse cellular processes including erythropoiesis, angiogenesis, energy metabolism, ischemia, and inflammation (Semenza et al., J. Biol. Chem. 1994 Sep. 23; 269(38): 237357-63 and Eltzschig et al., Nat. Rev. Drug Discov. 2014 November; 13(11):852-69). HIF is present in cells almost exclusively in two forms: HIF-1 and HIF-2. They are heterodimeric transcription factors consisting of a constitutively produced highly abundant HIF-β subunit and either a HIF-1α or HIF-2α partner, in the case of HIF-1 and HIF-2, respectively, sharing 48% sequence homology (Rabinowitz M H, J. Med. Chem. 2013 Dec. 12; 56(23):9369-4025). HIF-1 is frequently associated with metabolic and vascular responses to hypoxia, whereas HIF-2 is associated with vascular systems but also somewhat more with erythropoiesis (Ratcliffe P J, J. Clin. Invest. 2007 April; 117(4):862-5).

The mechanism by which oxygen controls HIF-1α has been revealed by the identification of HIF prolyl hydroxylases (PHDs) (Bruick and McKnight, Science 2001 Nov. 9; 294(5545):1337-40). Under normoxia, PHD hydroxylates proline residues in the oxygen dependent degradation (ODD) domain of HIF-1α, thereby allowing binding to von Hippel Lindau protein (pVHL)-elonginB-elonginC, leading to active ubiquitination and degradation with a half-life of approximately 5 min. On the other hand, the oxygen deprivation under hypoxia impairs hydroxylation of HIF-1α, by PHDs, resulting in reduced HIF-1α, turnover and subsequent induction of target gene transcription (Rabinowitz M H, J. Med. Chem. 2013 Dec. 12; 56(23):9369-4025). PHDs belong to the family of the dioxygenase enzymes that require oxygen, iron, and 2-oxyglutarate (2-OG) for their catalytic activity. Their low affinity to oxygen, which is about 2 to 10 times higher than physiological oxygen concentrations, enables the enzymes to act as oxygen sensors. Three PHD isoforms (PHD1, PHD2, and PHD3) have been identified, and their substrates are known to be quite diverse and isoform-specific (Rabinowitz M H, J. Med. Chem. 2013 Dec. 12; 56(23):9369-4025 and; Eltzschig et al., Nat. Rev. Drug Discov. 2014 November; 13(11):852-69).

PHD2 is considered critical in regulating the HIF pathway. Specifically, enhanced angiogenesis, and increased levels of vascular endothelial growth factor (VEGF)-A and erythropoietin (EPO) were observed in conditional knockout of PHD2 (Takeda et al., Circulation 2007 Aug. 14; 116(7): 774-81). Such observations, along with the previous report that HIF enhanced EPO release and concomitantly increased erythropoiesis, imply that activation of HIF by modulating PHDs could be beneficial for patients with anemia and ischemia-related diseases. Accordingly, pharmacological approaches to activate the HIF pathway by inhibiting PHD activity have been pursued to treat systemic and local diseases the treatment of which can benefit from HIF activation (Rabinowitz M H, J. Med. Chem. 2013 Dec. 12; 56(23):9369-4025 and; Eltzschig et al., Nat. Rev. Drug Discov. 2014 November; 13(11):852-69).

Hypoxia and inflammation are intimately linked on many levels and have functional roles in many human diseases. Indeed, a wide range of clinical conditions is characterized by hypoxia- or ischemia-driven inflammation or by inflammation-associated hypoxia. Accumulating evidence shows that inflammatory lesions are characterized by the occurrence of tissue hypoxia that is probably a result of increased metabolism and diminished oxygen supply. For example, this is the case during the intestinal inflammation observed in patients suffering from inflammatory bowel disease (IBD), including ulcerative colitis and Crohn's disease (Karhausen et al., J. Clin Invest. 2004 October; 114(8):1098-106). Such inflammatory hypoxia is caused by dramatic shifts in metabolic supply and demand ratios. Emerging evidence indicates that concomitant inhibition of PHDs and subsequent stabilization of HIFs during tissue hypoxia could function as an endogenous adaptive response to counterbalance hypoxia-driven inflammation and to restore normal cellular functions (Eltzschig et al., Nat. Rev. Drug Discov. 2014 November; 13(11):852-69).

Neuronal damage secondary to brain injuries such as cerebral hypoxia and neurodegenerative process, is a complex process that involves inflammatory changes. The activation of a common mechanism related to survival or cell death, mediated by the stabilization and trans-activation of HIF-1α, has been observed in these conditions. PHDs are the gatekeepers for the oxygen-dependent degradation of HIF-1α and also function as integrated sensors of cellular metabolism (Aragonés et al., Cell Metab. 2009 Jan. 7; 9(1):11-22). The phenomenon that hypoxic preconditioning (HP) protects against subsequent severer anoxia was discovered approximately two decades ago. Subsequently, the effects of HP have been studied intensively in vitro and in vivo models of acute hypoxia. Although the exact mechanisms are not completely disclosed, the underlying molecular mechanisms have been postulated. For example, HP activates a great variety of endogenous protective mediators including HIF-1α and HIF-2α stabilization increasing the capability of cell survival under severe oxygen deprivation (Wu et al., 2012, The protective role of hypoxic preconditioning in CNS, Anoxia, Dr. Pamela Padilla (Ed.), InTech, DOI: 10.5772/27621).

Brain diseases where hypoxia occurs mainly include stroke, cerebral palsy, traumatic injuries etc. Until now, there are no any effective drugs to protect brain from these diseases. Disclosure of the mechanism of HP will contribute to drug discovery for prevention against said diseases. A number of cellular adaptive responses to hypoxia are mediated by HIF-1α and activation of this factor by HP enhances the capability to tolerate severe anoxia or ischemia. The target genes of HIF-1, on the one hand, are involved in energy homeostasis, such as EPO in the regulation of erythropoiesis, vascular endothelial growth factor (VEGF) in angiogenesis, glucose transmitters (GLUTs) in glucose uptake and glycolytic enzymes of anaerobic glycolysis (Speer et al., Free Radio. Biol. Med. 2013 September; 62:23-36). Moreover, activation of HIF-1α in oligodendrocytes has been reported to induce EPO, which confers protection in oligodendrocytes against excitotoxicity (Sun et al., J. Neurosci. 2010 Jul. 14; 30(28):9621-30). In this sense the benefit of EPO in several diseases such as Multiple Sclerosis, stroke and traumatic brain injuries has been also demonstrated (Peng et al., J. Neurosurg. 2014 September; 121(3):653-64; Ehrenreich et al., Stroke 2009 December; 40(12): e647-56; Li et al., Ann. Neurol. 2004 December; 56(6):767-77). In addition, hypoximimetic agents (i.e. agents producing the same biological responses as the ones produced when hypoxia occurs) such as desferrioxamine (DFX) protect neuronal insults induced by 3-nitropoionic acid (Yang et al., J. Neurochem. 2005 May; 96(3):513-25). Therefore, PHDs inhibition by hypoximimetic small-molecules represents an interesting strategy or the development of neuroprotective therapies for the clinical management of conditions where hypoxia is present such as stroke, cerebral palsy, traumatic injuries and neurodegenerative diseases such as Multiple Sclerosis, Huntington disease, Alzheimer disease and Parkinson disease.

A substantial number of pharmacological studies (generally using nonspecific PDH2 inhibitors) have been conducted in animal models, and a few clinical studies have been performed. Indeed, several companies are involved in the discovery and development of PHD inhibitors for anemia and other indications such as IBD, myocardial ischaemia-reperfusion injury, acute lung injury, organ transplantation, acute kidney injury and arterial diseases are areas in which PHD inhibitors are actively being pursued by many researchers as a novel therapeutic approach (Rabinowitz M H, J. Med. Chem. 2013 Dec. 12; 56(23):9369-4025 and; Eltzschig et al., Nat. Rev. Drug Discov. 2014 November; 13(11):852-69).

The original description of HIF-selective PHDs as regulators of HIF expression has provided a template for the development of PHD-based molecular tools and therapies. Pharmacological inactivation of the PHDs by 2-OG analogues is sufficient to stabilize HIF-1α, but this action is nonspecific with respect to individual PHD isoforms and in vitro studies showed that the ODD sequence of HIF1α is hydroxylated most efficiently by PHD2 (Rabinowitz MH, J. Med. Chem. 2013 Dec. 12;56(23):9369-4025). These observations have generated considerable interest in identifying enzyme-modifying small-molecule inhibitors. Indeed, several PHD inhibitor classes have been described, including iron chelators such as DFX, hydralazine, AKB-4924, FG-2229, TM-6008 and 1-mimosine 1-mimosine; CUL2 deneddylators such as MLN4924; 2-OG mimics such as ximethyloxalylglycine and N-oxalyl-d-phenylalanine; PHD active-site blockers such as pyrazolopyridines, 8-hydroxyquinolines, compound A, FG-4497 and TM-6089; and $Fe^{2+}$ substitutes such as $Co^{2+}$, $Ni^{2+}$ and $Cu^{2+}$. The mechanism of action of these compounds is based on the observation that the binding of the co-substrate 2-OG to the catalytic domain, which harbours an essential $Fe^{2+}$ ion, is crucial for enzymatic PHD2 activity. Therefore, chemical compounds that structurally mimic 2-OG, such as N-oxalylglycine or its precursor DMOG, inhibit PHD2 by blocking the entry of the co-substrate (Rabinowitz M H, J. Med. Chem. 2013 Dec. 12; 56(23):9369-4025 and; Eltzschig et al., Nat. Rev. Drug Discov. 2014 November; 13(11):852-69).

DFX is an hydroxamic acid derivative acting as a metal chelator that is in clinical use for the treatment of acute iron intoxication and of chronic iron overload due to transfusion-dependent anemias. However, DFX is not indicated for the treatment of chronic diseases and it is contraindicated in severe renal diseases since primarily the kidney excretes the drug and the iron chelate. Moreover, DFX only induces HIF-1α stabilization and activation at relatively high concentrations in the cells.

Triterpenoids are widely distributed in edible and medicinal plants and are an integral part of the human diet. Among them, pentacyclic triterpenoids are derived from the linear hydrocarbon squalene and they are highly multifunctional and, thus, have a wide range of commercial applications in the agriculture, food, cosmetics and pharmaceutical sectors as pesticides, drugs, adjuvants, antimicrobials, anticancer agents, surfactants, preservatives, etc. (Sheng et al., Nat. Prod. Rep. 2011 March; 28(3):543-93; Yadav et al., Toxins (Basel) 2010 October; 2(10):2428-66). The acidic function and hydroxyl (—OH) groups of the triterpenoids cannot interact with the stationary phase, as the two groups are located on the opposite sides of the compound. There are three main triterpene families: oleane, ursane, and lupane triterpenes. The main triterpenoids found in the oleane family are oleanolic acid, maslinic acid, erythrodiol, and β-amyrin; in the ursane family are ursolic acid and uvaol; and in the lupane family are lupeol, betulin, and betulinic acid (Yadav et al., Toxins (Basel) 2010 October; 2(10):2428-66).

Dietary triterpenoids such as oleanolic, ursolic, betulinic acid and maslinic acids have been extensively studied for bioactivity and pharmaceutical application and they have been widely used also as templates to produce novel derivatives with improved bioactivities. Triterpenoids have been shown to inhibit the activation of the transcription factors NF-κB (Nuclear factor-kappa B) and STAT3 (Signal transducer and activator of transcription 3), to modulate the Nrf2 (NFE2L2 or Nuclear factor (erythroid-derived 2)-like 2) pathway and to bind and activate the bile receptor TGR5 (Sato et al., Biochem. Biophys. Res. Comm. 2007 Nov. 3; 362(4):793-8). However, the potential activity of triterpenoids on PDH2 inhibition and HIF-1α stabilization has not been described. Surprisingly, ursolic, betulinic, and oleanolic acids, which are the precursors of compounds II to XIV disclosed herein bind to PHD2 but do not activate the HIF-1α pathway. This finding led to generate hydroxamate derivatives able to bind PHD2, to chelate $Fe^{2+}$ in its active pocket and as a consequence these compounds activate the HIF pathway and stabilize HIF-1α and HIF-2α proteins. Compounds III, IV, V, VI, VIII, IX, X, XI, and XIV and XV are novel chemical entities whilst compounds II, VII, XII and XIII have been reported to have anticancer activity in vitro, which is not related to HIF-1α activation (Wiemann et al., Eur. J. Med. Chem. 2015 Dec. 1; 106:194-210; Wiemann et al., Bioorg. Med. Chem. Left. 2016 Feb. 1; 26(3):907-9; CN102180939 B). In fact, HIF-1α inhibition by some triterpenoids, as opposite to HIF-1α activation, has been suggested as a potential strategy for anti-cancer therapies (Dasgupta et al., Angiogenesis. 2015 July; 18(3): 283-99; Jin et al., Arch Pharm Res. 2007 April; 30(4): 412-8; Dai et al., J Nat Prod. 2006 December; 69(12): 1715-20).

BRIEF DESCRIPTION

Departing from the prior art, the problem of the present invention is to provide novel pentacyclic triterpenoid derivatives (triterpenoid derivatives) that induce HIF-1α and HIF-2α stabilization and activate the HIF pathway.

Present invention relates to triterpene derivatives of Formula (Ia) or stereoisomers, pharmaceutically acceptable salts or pharmaceutically acceptable solvates thereof, Formula (Ia)

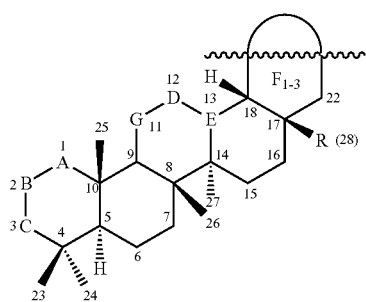

wherein independently,
A-B is selected from a single carbon-carbon bond or a double carbon-carbon bond;
B is selected from a methylene (—$CH_2$—), an olefin methine (=CH—), a hydroxymethine [—CH(OH)—], or a hydroxylated olefin carbon [—C(OH)=];
B-C is selected from a single carbon-carbon bond or a double carbon-carbon bond; or be part of a heterocyclic ring comprising one or more heteroatoms wherein at least one of said heteroatoms is nitrogen; and wherein said heterocyclic ring is a five membered ring comprising one nitrogen and one oxygen;
C is selected from a hydroxymethine [—CH(OH)—], an acyloxymethine [—CH(OCOR')—], an olefin methine (=CH—), a carbonyl [—C(=O)—], an oxime [—C(=N—OH)—] or an hydrazone [—C(=N—$NH_2$)—], wherein R' is methyl;
D-E is a single or a double carbon-carbon bond;
F is selected from $F_{1a}$, $F_{2a}$ or $F_{3a}$;

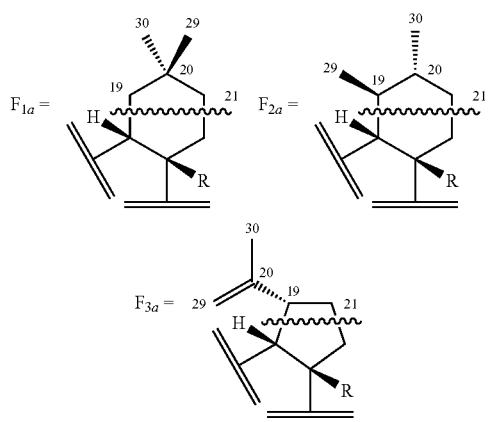

G is selected from a methylene (—$CH_2$—) or a carbonyl [—C(=O)—]; and
R is a hydroxamate group (—CONHOH);
and wherein,
when C is an acyloxymethine [—CH(OCOR')—], the triterpene derivative of Formula (Ia) is (V)

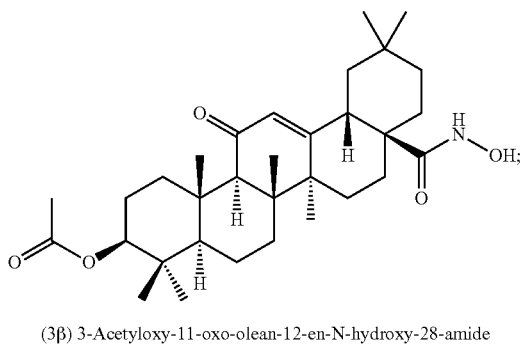

(3β) 3-Acetyloxy-11-oxo-olean-12-en-N-hydroxy-28-amide when B is a methylene (—$CH_2$—), C is a hydroxymethine [—CH(OH)—], D-E is a double carbon-carbon bond, G is a methylene (—$CH_2$—) and R is a hydroxamate (—CONHOH), F is $F_{3a}$;
when B is a methylene (—$CH_2$—), C is a hydroxymethine [—CH(OH)—], D-E is a single carbon-carbon bond, G is a methylene (—$CH_2$—) and R is a hydroxamate (—CONHOH), F is selected from $F_{1a}$ or $F_{2a}$;
when B is a methylene (—$CH_2$—), C is an oxime [—C(=N—OH)—], D-E is a double carbon-carbon bond, G is a methylene (—$CH_2$—) and R is a hydroxamate (—CONHOH), F is selected from $F_{1a}$ or $F_{3a}$.

Additionally, present invention refers to pharmaceutical compositions comprising at least one triterpene derivative of Formula (Ia), as described above herein, as a first active ingredient and at least one excipient or carrier, and optionally further comprising at least a second active ingredient Another aspect of present invention refers to the triterpene derivatives of Formula (Ia), and the pharmaceutical compositions thereof, as described above herein, for use as a medicament.

Present invention also refers to triterpene derivatives of Formula (I) or stereoisomers, pharmaceutically acceptable salts or pharmaceutically acceptable solvates thereof, Formula (I)

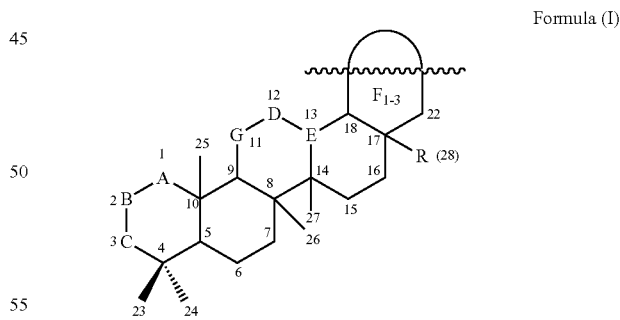

wherein independently,
A-B is selected from a single carbon-carbon bond or a double carbon-carbon bond;
B is selected from a methylene (—$CH_2$—), an olefin methine (=CH—), a hydroxymethine [—CH(OH)—], or a hydroxylated olefin carbon [—C(OH)=];
B-C is selected from a single carbon-carbon bond or a double carbon-carbon bond; or be part of a heterocyclic ring comprising one or more heteroatoms wherein at least one of said heteroatoms is nitrogen; and wherein said heterocyclic ring is a five-membered ring comprising one nitrogen and one oxygen;

C is selected from a hydroxymethine [—CH(OH)—], an acyloxymethine [—CH(OCOR')—], an olefin methine (=CH—), a carbonyl [—C(=O)—], an oxime [—C(=N—OH)—] or an hydrazone [—C(=N—NH$_2$)—], wherein R' is methyl;

D-E is a single or a double carbon-carbon bond;

F is selected from $F_1$, $F_2$ or $F_3$;

$F_1$ = [structure]   $F_2$ = [structure]

$F_3$ = [structure]

G is selected from a methylene (—CH$_2$—) or a carbonyl [—C(=O)—]; and

R is a hydroxamate group (—CONHOH);

for use in the treatment of a condition or disease responsive to the activation of the HIF pathway.

Present invention further relates to pharmaceutical compositions comprising triterpene derivatives, as described above herein, for use in the treatment of conditions or diseases responsive to the activation of the HIF pathway.

Detailed Description

Present invention relates to triterpenoid derivatives comprising an hydroxamate functional group at position 28, and compositions comprising said triterpenoids derivatives, which show capacity to bind PHD2, stabilize HIF-1α and HIF-2α proteins, activate the HIF pathway in different cell types, induce angiogenesis in human endothelial vascular cell, show neuroprotective activity in vitro and in vivo, antidiabetic activity in vivo, and increase the plasma levels of Erythropoietin in vivo.

Said triterpenoid derivatives act also in a selective manner and do not induce Nrf2 activation, NF-κB inhibition, STAT3 inhibition, and TGR5 activation, which are known activities of their natural triterpenoid precursors. Said triterpenoid derivatives are useful in the treatment of conditions and or diseases responsive to the activation of the HIF pathway. Therefore, present invention relates to diseases, the treatment of which benefits or is responsive to HIF-1α and HIF-2α activation, and thus, present invention does not refer to diseases or conditions the treatment of which benefits or is responsive to HIF-1α inhibition.

More specifically, present invention refers to triterpene derivatives of Formula (Ia):

Formula (Ia)

[structure]

where independently

A-B is selected from a single carbon-carbon bond or a double carbon-carbon bond;

B is selected from a methylene (—CH$_2$—), an olefin methine (=CH—), a hydroxymethine [—CH(OH)—], or a hydroxylated olefin carbon [—C(OH)=];

B-C is selected from a single carbon-carbon bond or a double carbon-carbon bond; or be part of a heterocyclic ring comprising one or more heteroatoms wherein at least one of said heteroatoms is nitrogen;

C is selected from a hydroxymethine [—CH(OH)—], an acyloxymethine [—CH(OCOR')—], an olefin methine (=CH—), a carbonyl [—C(=O)—], an oxime [—C(=N—OH)—] or an hydrazone [—C(=N—NH$_2$)—], wherein R' is methyl;

D-E is a single or a double carbon-carbon bond;

F is selected from $F_{1a}$, $F_{2a}$ and $F_{3a}$;

$F_{1a}$ = [structure]   $F_{2a}$ = [structure]

$F_{3a}$ = [structure]

G is selected from a methylene (—CH$_2$—) or a carbonyl [—C(=O)—]; and

R is a hydroxamate group (—CONHOH);

and wherein, when B is a methylene (—CH$_2$—), C is a hydroxymethine [—CH(OH)—], D-E is a double carbon-carbon bond, and R is a hydroxamate (—CONHOH), F is $F_{3a}$;

when B is a methylene (—CH$_2$—), C is a hydroxymethine [—CH(OH)—], D-E is a single carbon-carbon bond, and R is a hydroxamate (—CONHOH), F is selected from $F_{1a}$ or $F_{2a}$;

when B is a methylene (—CH$_2$—), C is an oxime [—C(=N—OH)—], D-E is a double carbon-carbon bond, and R is a hydroxamate (—CONHOH), F is selected from $F_{2a}$ or $F_{3a}$.

In one embodiment the triterpene derivatives of Formula (Ia), as disclosed above herein, B-C can be part of a heterocyclic ring comprising one or more heteroatoms wherein at least one of said heteroatoms is nitrogen, and wherein said heterocyclic ring is a five-membered ring.

In one embodiment of the triterpene derivatives of Formula (Ia), as disclosed above herein, B-C can be part of a heterocyclic ring comprising one or more heteroatoms wherein at least one of said heteroatoms is nitrogen, and wherein said heterocyclic ring is a five-membered ring comprising two nitrogen atoms.

In one embodiment of the triterpene derivatives of Formula (Ia), as disclosed above herein, B-C can be part of a heterocyclic ring comprising one or more heteroatoms wherein at least one of said heteroatoms is nitrogen, and wherein said heterocyclic ring is a five-membered ring comprising one nitrogen and one oxygen.

The triterpene derivatives of Formula (Ia), as disclosed above herein, also comprise their analogs, derivatives, tautomeric forms, isomers, stereoisomers, polymorphs, pharmaceutically acceptable salts or pharmaceutically acceptable solvates.

For the purposes of present description, the term "analogue/s" refers to any entity structurally derived or homologous to the compounds disclosed in present invention.

In the context of present description, the term "derivative/s" of the compounds disclosed herein should be interpreted as any triterpenoid analogue, always substituted in the position 28, according to the definition of R above herein, which provides with the pharmacological properties described herein to the triterpenoid compounds, but also featuring other substitutions in the other positions of the triterpenoid molecule, different to the substitutions described herein.

The term "tautomers" are constitutional isomers of organic compounds that readily interconvert by a chemical process (tautomerization).

The term "isomer" is defined formally by the IUPAC (International Union of Pure and Applied Chemistry) as one of several species (or molecular entities) that have the same atomic composition (molecular formula) but different formulae or different stereochemical formulae, whereas "stereoisomers" is defined formally by the IUPAC as compounds, which have identical chemical constitution, but differ with regard to the arrangement of the atoms or groups in space.

As used herein "polymorph" refers to crystalline forms having the same chemical composition but different spatial arrangements of the molecules, atoms, and/or ions forming the crystal.

The term "pharmaceutically acceptable salt" refers to any pharmaceutically acceptable salt, which upon administration to the patient is capable of providing (directly or indirectly) a compound as described herein. Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts. However, it will be appreciated that non-pharmaceutically acceptable salts also fall within the scope of the invention since those may be useful in the preparation of pharmaceutically acceptable salts. Procedures for salt formation are conventional in the art.

The term "solvate" in accordance with this invention should be understood as meaning any form of the active compound in accordance with the invention in which said compound is bonded by a non-covalent bond to another molecule (normally a polar solvent), including especially hydrates and alcoholates.

In a preferred embodiment, the triterpene derivatives disclosed refer to the compounds of Formula (III), (IV), (V), (VI), (VIII), (IX), (X), (XI), (XIV), (XV), or analogs, derivatives, tautomeric forms, isomers, stereoisomers, polymorphs, pharmaceutically acceptable salts or pharmaceutically acceptable solvates thereof.

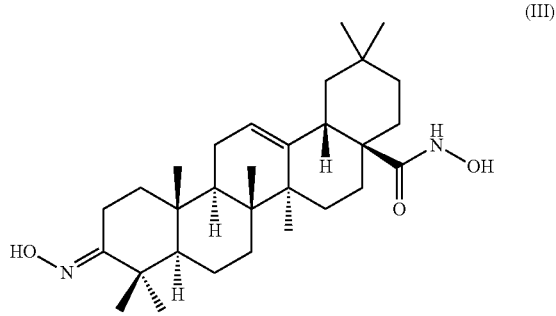

3-Hydroxyimino-N-hydroxy-olean-12-en-28-amide

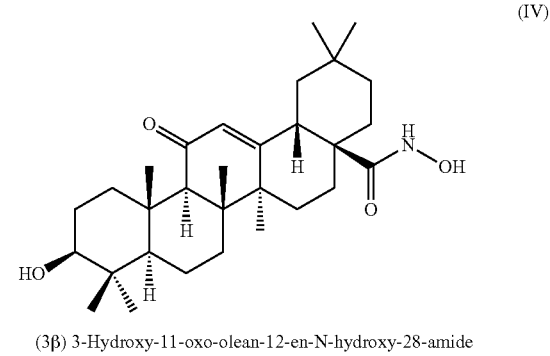

(3β) 3-Hydroxy-11-oxo-olean-12-en-N-hydroxy-28-amide

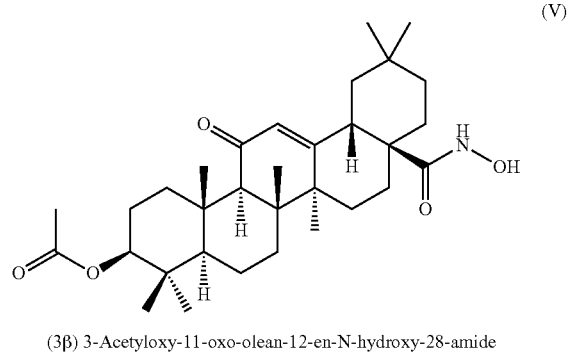

(3β) 3-Acetyloxy-11-oxo-olean-12-en-N-hydroxy-28-amide

-continued (VI)

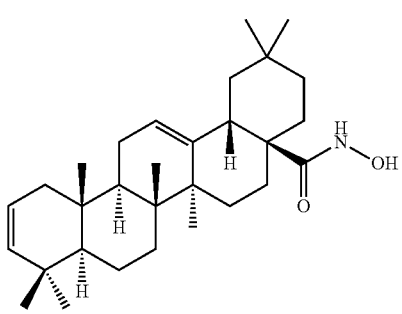

Oleana-2,12-dien-N-hydroxy-28-amide (VIII)

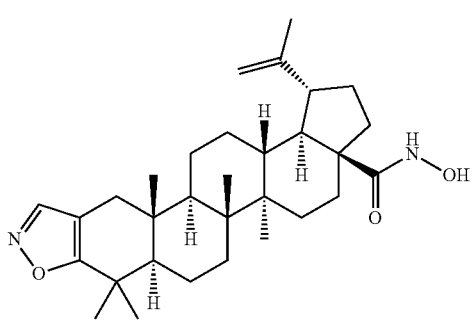

Lup-2-eno[2,3-d]isoxazol-N-hydroxy-28-amide (IX)

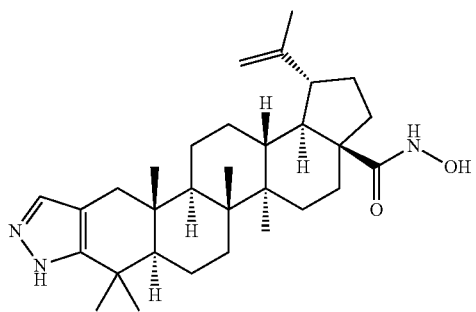

1'H-Lup-20(29)-eno[3,2-c] pyrazol-N-hydroxy-28-amide (X)

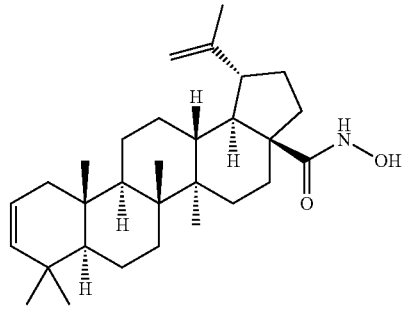

Lupa-2,20(29)-dien-N-hydroxy-28-amide

-continued (XI)

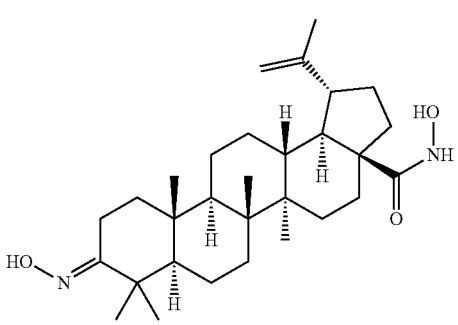

3-Oxo-lup-20(29)-en-28-acid (XIV)

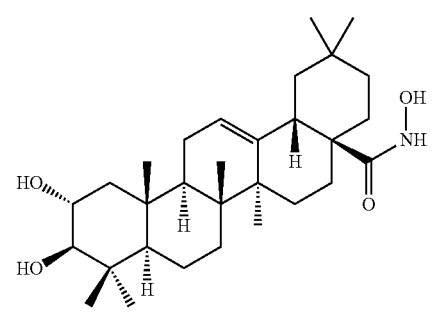

(2α,3β) 2,3-Dihydroxy-N-hydroxy-olean-12-en-28-amide (XV)

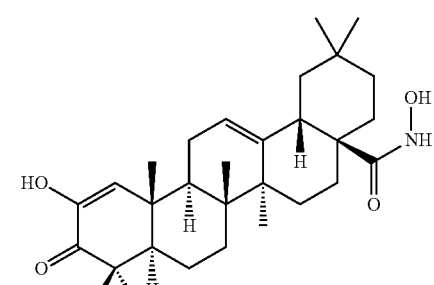

2-Hydroxy-3-oxo-oleana-1,12-dien-N-hydroxy-28-amide

In a preferred embodiment of the triterpene derivatives of Formula (Ia), when C is an acyloxymethine [—CH(OCOR')—], the triterpene derivative of Formula (Ia) is (V)

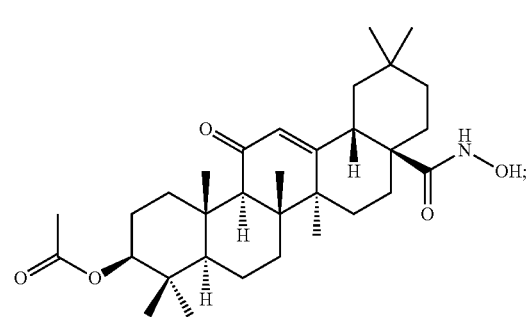

(3β) 3-Acetyloxy-11-oxo-olean-12-en-N-hydroxy-28-amide

As shown in the examples and figures of present description, the modifications comprised in the general Formula (Ia) confer the compounds disclosed herein with the capacity to bind PHD2, stabilize HIF-1α and HIF-2α proteins, activate the HIF pathway in different cell types, induce angiogenesis in human endothelial vascular cell, show neuroprotective activity in vitro and in vivo, antidiabetic activity in vivo, and increase the plasma levels of Erythropoietin in vivo. Said compounds of Formula (Ia) or analogs, derivatives, tautomeric forms, isomers, stereoisomers, polymorphs, pharmaceutically acceptable salts or pharmaceutically acceptable solvates thereof, act in a selective manner and do not induce Nrf2 activation, NF-κB inhibition, STAT3 inhibition, and TGR5 activation, which are known activities of their natural triterpenoid precursors.

An embodiment disclosed herein refers to compositions, particularly pharmaceutical compositions, comprising at least a compound of Formula (Ia) or analog, derivative, tautomeric form, isomer, stereoisomer, polymorph, pharmaceutically acceptable salt or pharmaceutically acceptable solvate thereof, as described above herein, and at least one excipient or carrier.

Said excipient or carrier refers, for the purpose of present invention, to an inert ingredient such as, but not limited to, cosolvents, surfactants, oils, humectants, emollients, preservatives, stabilizers and antioxidants. Any pharmacologically acceptable buffer may be used, such as TRIS or any phosphate buffer.

Another embodiment disclosed herein refers to compositions, particularly pharmaceutical compositions, comprising at least a compound of Formula (Ia) or analog, derivative, tautomeric form, isomer, stereoisomer, polymorph, pharmaceutically acceptable salt or pharmaceutically acceptable solvate thereof, as described above herein, and at least a second active compound having additive or synergistic biological activities.

For the purposes of present description, the term "active compound or active principle" should be taken as synonyms and mean a chemical entity which exerts therapeutic effects when administered to human or animal beings.

A further embodiment disclosed herein refers to the compounds of Formula (Ia) or analogs, derivatives, tautomeric forms, isomers, stereoisomers, polymorphs, pharmaceutically acceptable salts or pharmaceutically acceptable solvates thereof, of present invention, for use as a medicament.

A further embodiment disclosed herein refers to the pharmaceutical compositions described above herein, comprising the compounds of Formula (Ia) or analogs, derivatives, tautomeric forms, isomers, stereoisomers, polymorphs, pharmaceutically acceptable salts or pharmaceutically acceptable solvates thereof, of present invention, for use as a medicament.

Said compounds of Formula (Ia) or analogs, derivatives, tautomeric forms, isomers, stereoisomers, polymorphs, pharmaceutically acceptable salts or pharmaceutically acceptable solvates thereof, show capacity to bind PHD2, stabilize HIF-1α and HIF-2α proteins, activate the HIF pathway in different cell types, induce angiogenesis in human endothelial vascular cell, show neuroprotective activity in vitro and in vivo, antidiabetic activity in vivo, and increase the plasma levels of Erythropoietin in vivo. Said compounds of Formula (Ia) or analogs, derivatives, tautomeric forms, isomers, stereoisomers, polymorphs, pharmaceutically acceptable salts or pharmaceutically acceptable solvates thereof, act in a selective manner and do not induce Nrf2 activation, NF-κB inhibition, STAT3 inhibition, and TGR5 activation, which are known activities of their natural triterpenoid precursors.

Said triterpenoid derivatives of Formula Ia, and pharmaceutical compositions thereof, are useful in the treatment of conditions and diseases which are responsive to the activation of the HIF pathway.

Therefore, the triterpene derivatives of Formula (Ia) are useful in conditions or diseases responsive to the activation of the HIF pathway, wherein thus, the treatment of said conditions or diseases benefits or is responsive to the activation of the HIF pathway.

According to present disclosure, the conditions and diseases responsive to the activation of the HIF pathway do not include solid tumors. This is the case since solid tumors develop neoangiogenesis that facilitate metastatic spread and therefore HIF-1 inhibitors are being developed as anti-cancer drugs to block abnormal vessel growth and function (Potente et al. Cell. 2011 Sep. 16; 146(6):873-87).

Particularly, one embodiment discloses the triterpene derivatives of Formula (Ia) described above herein, and pharmaceutical compositions thereof, for use in the treatment of a range of conditions or diseases which are responsive to the activation of the HIF pathway which comprise but are not limited to stroke, cerebral palsy, traumatic injuries and neurodegenerative diseases. Examples of neurodegenerative diseases include but are not limited to Multiple Sclerosis, Huntington disease, Alzheimer disease or Parkinson disease.

For the purposes of present description stroke refers to neurological deficit of cerebrovascular cause. Strokes can be classified into two major categories: ischemic and hemorrhagic. Ischemic strokes are caused by interruption of the blood supply to the brain, while hemorrhagic strokes result from the rupture of a blood vessel or an abnormal vascular structure.

For the purposes of present description cerebral palsy refers to a group of permanent movement disorders that appear in early childhood and are caused by abnormal development or damage to the parts of the brain that control movement, balance, and posture.

For the purposes of present description traumatic injuries refer to physical injuries of sudden onset and severity, which require immediate medical attention. Traumatic injuries are the result of a wide variety of blunt, penetrating and burn mechanisms. Said traumatic injuries include motor vehicle collisions, sports injuries, falls, natural disasters and a multitude of other physical injuries.

Another embodiment discloses the triterpene derivatives of Formula (Ia) described above herein, and pharmaceutical compositions thereof, for use in the treatment of a range of conditions or diseases which are responsive to the activation of the HIF pathway, wherein said conditions or diseases comprise, but are not limited to IBD, myocardial ischaemia-reperfusion injury, acute lung injury, diabetic and chronic wounds, organ transplantation, acute kidney injury or arterial diseases. More preferably said condition or disease is selected from IBD, myocardial ischaemia-reperfusion injury, acute lung injury, organ transplantation, acute kidney injury or arterial diseases.

For the purposes of present description IBD refers to a group of inflammatory conditions of the colon and small intestine. Crohn's disease and ulcerative colitis are the principal types of inflammatory bowel disease within others.

For the purposes of present description myocardial ischaemia-reperfusion injury refers to the tissue damage caused when blood supply returns to the tissue after a period of myocardial ischemia or lack of oxygen (anoxia, hypoxia).

For the purposes of present description acute lung injury refers to a condition that is characterized by acute severe hypoxia and where its diagnosis is based on the presence of non-cardiogenic pulmonary oedema and respiratory failure in a critically ill patient.

For the purposes of present description infectious diseases refer to diseases caused by pathogenic microorganisms, such as bacteria, viruses, parasites or fungi, and wherein said diseases can be spread, directly or indirectly, from one person to another.

For the purposes of present description diabetic and chronic wounds refer to wounds, which may be caused by a diabetic condition, that do not heal in an orderly set of stages and in a predictable amount of time the way most wounds do. In general, wounds that do not heal within three months are often considered chronic For the purposes of present description acute kidney injury refers an abrupt loss of kidney function from numerous causes that develops within 7 days. Said abrupt loss of kidney function causes damage to the kidney tissue and it is generally caused by decreased renal blood flow (renal ischemia).

For the purposes of present description arterial diseases include a class of diseases that involve the blood vessels.

Particularly, one embodiment discloses the compounds of Formula (Ia) as described herein, and pharmaceutical compositions thereof, for use in the treatment of a condition or disease responsive to the activation of the HIF pathway selected from IBD, myocardial ischaemia-reperfusion injury, acute lung injury, diabetic and chronic wounds, organ transplantation, acute kidney injury or arterial diseases. In a preferred embodiment said condition or disease responsive to the activation of the HIF pathway selected from IBD, myocardial ischaemia-reperfusion injury, acute lung injury, organ transplantation, acute kidney injury or arterial diseases One embodiment of present invention, also discloses the compounds of Formula (Ia), as described above herein, and pharmaceutical compositions thereof, for use in the treatment of a condition or disease responsive to the activation of the HIF pathway wherein said condition or disease responsive to the activation of the HIF pathway a metabolic pathology. In a preferred embodiment said metabolic pathology is diabetes. In another preferred embodiment said metabolic pathology is a lipid metabolism disorder. In yet another preferred embodiment said metabolic pathology is hyperlipidemia. In another preferred embodiment said metabolic pathology is hypertriglyceridemia. It has been described that PHD2 inhibitors improve glucose and lipid metabolism and protects against obesity and metabolic syndrome (Rahtu-Korpela et al. Diabetes. 2014 October; 63(10):3324-33).

The term "metabolic pathologies" refers to pathologies where the normal metabolic process has been altered.

The term "diabetes", for the purposes of present invention, refers a group of metabolic disorders in which high blood sugar levels are present over a prolonged period. Diabetes is due to either a low production of insulin by the pancreas or to an inappropriate response of the body to the insulin produced.

"Hyperlipidemia" refers to a condition wherein the subject presents an abnormally elevated level of any, or all, lipids, or lipoproteins in the blood.

"Hypertriglyceridemia" refers to a condition wherein the subject presents high blood levels of triglycerides. Elevated levels of triglycerides are associated with atherosclerosis, even in the absence of hypercholesterolemia (high cholesterol levels), and predispose to cardiovascular disease. Very high triglyceride levels also increase the risk of acute pancreatitis.

Another embodiment disclosed herein refers to triterpene derivatives of Formula (I) or analogs, derivatives, tautomeric forms, isomers, stereoisomers, polymorphs, pharmaceutically acceptable salts or pharmaceutically acceptable solvates thereof,

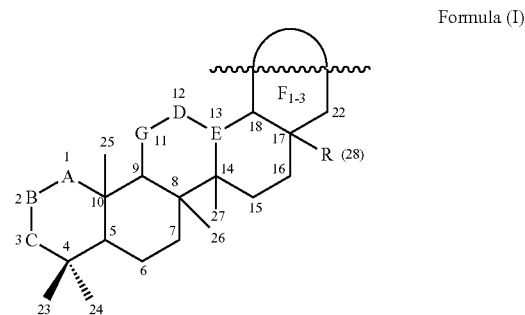

Formula (I)

wherein independently,
A-B is selected from a single carbon-carbon bond or a double carbon-carbon bond;
B is selected from a methylene (—CH$_2$—), an olefin methine (═CH—), a hydroxymethine [—CH(OH)—], or a hydroxylated olefin carbon [—C(OH)═];
B-C is selected from a single carbon-carbon bond or a double carbon-carbon bond; or be part of a heterocyclic ring comprising one or more heteroatoms wherein at least one of said heteroatoms is nitrogen;
C is selected from a hydroxymethine [—CH(OH)—], an acyloxymethine [—CH(OCOR')—], an olefin methine (═CH—), a carbonyl [—C(═O)—], an oxime [—C(═N—OH)—] or an hydrazone [—C(═N—NH$_2$)—], wherein R' is methyl;
D-E is a single or a double carbon-carbon bond;
F is selected from F$_1$, F$_2$ or F$_3$;

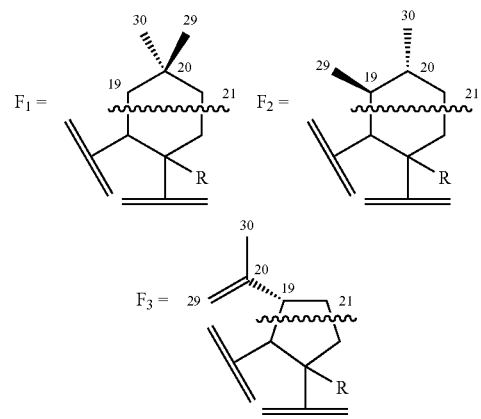

G is selected from a methylene (—CH$_2$—) or a carbonyl [—C(═O)—]; and
R is a hydroxamate group (—CONHOH);
for use in the treatment of conditions or diseases responsive to the activation of the HIF pathway.

Therefore, the triterpene derivatives of Formula (I) are useful in conditions or diseases responsive to the activation of the HIF pathway, wherein thus, the treatment of said conditions or diseases benefits or is responsive to the activation of the HIF pathway.

The triterpene derivatives of Formula (I), as disclosed above herein, also comprise their analogs, derivatives, tautomeric forms, isomers, stereoisomers, polymorphs, pharmaceutically acceptable salts or pharmaceutically acceptable solvates, as defined above herein for the purposes of present invention. In particular, the triterpene derivatives of Formula (I) of present invention, as disclosed above herein, comprise all stereoisomers, and any pharmaceutically acceptable salts or pharmaceutically acceptable solvates thereof.

In one embodiment the triterpene derivatives of Formula (I), as disclosed above herein, B-C can be part of a heterocyclic ring comprising one or more heteroatoms wherein at least one of said heteroatoms is nitrogen, and wherein said heterocyclic ring is a five-membered ring.

In one embodiment of the triterpene derivatives of Formula (I), as disclosed above herein, B-C can be part of a heterocyclic ring comprising one or more heteroatoms wherein at least one of said heteroatoms is nitrogen, and wherein said heterocyclic ring is a five-membered ring comprising two nitrogen atoms.

In one embodiment of the triterpene derivatives of Formula (I), as disclosed above herein, B-C can be part of a heterocyclic ring comprising one or more heteroatoms wherein at least one of said heteroatoms is nitrogen, and wherein said heterocyclic ring is a five-membered ring comprising one nitrogen and one oxygen.

In another embodiment of the triterpene derivatives of Formula (I), when C is an acyloxymethine [—CH(OCOR')—], the triterpene derivative of Formula (I) is

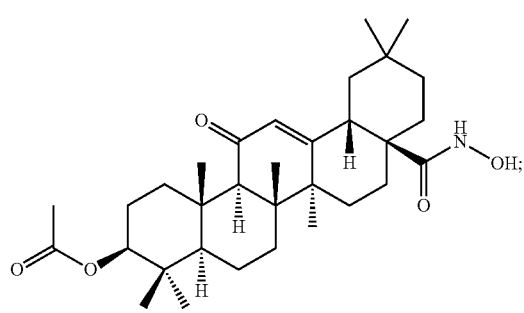

(3β) 3-Acetyloxy-11-oxo-olean-12-en-N-hydroxy-28-amide

One embodiment of the triterpene derivatives of Formula (I) refers to the stereoisomer thereof Formula (Ia):

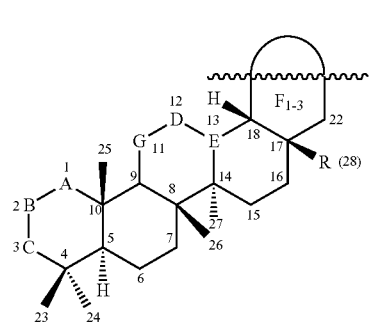

Formula (Ia)

where independently
A-B is selected from a single carbon-carbon bond or a double carbon-carbon bond;

B is selected from a methylene (—CH$_2$—), an olefin methine (=CH—), a hydroxymethine [—CH(OH)—], or a hydroxylated olefin carbon [—C(OH)=];

B-C is selected from a single carbon-carbon bond or a double carbon-carbon bond; or be part of a heterocyclic ring comprising one or more heteroatoms wherein at least one of said heteroatoms is nitrogen;

C is selected from a hydroxymethine [—CH(OH)—], an acyloxymethine [—CH(OCOR')—], an olefin methine (=CH—), a carbonyl [—C(=O)—], an oxime [—C(=N—OH)—] or an hydrazone [—C(=N—NH$_2$)—], wherein R' is methyl;

D-E is a single or a double carbon-carbon bond;

F is selected from

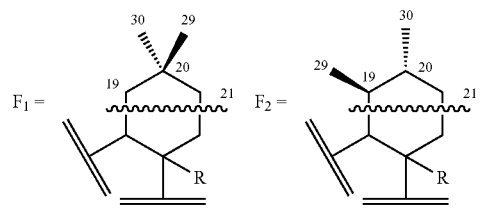

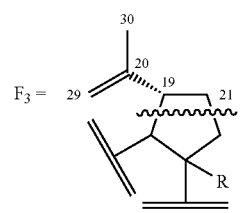

and wherein $F_1$ is $F_{1a}$, $F_2$ is $F_{2a}$ and $F_3$ is $F_{3a}$;

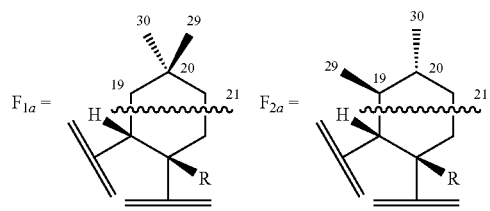

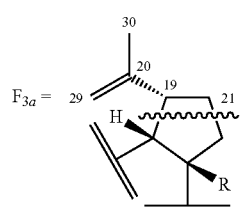

G is selected from a methylene (—CH$_2$—) or a carbonyl [—C(=O)—]; and

R is a hydroxamate group (—CONHOH);

for use in the treatment of conditions or diseases responsive to the activation of the HIF pathway.

Another embodiment of the triterpene derivatives of Formula (I) refers to the stereoisomer thereof Formula (Ib):

Formula (Ib)

wherein independently,
A-B is selected from a single carbon-carbon bond or a double carbon-carbon bond;
B is selected from a methylene (—CH$_2$—), an olefin methine (=CH—), a hydroxymethine [—CH(OH)—], or a hydroxylated olefin carbon [—C(OH)=];
B-C is selected from a single carbon-carbon bond or a double carbon-carbon bond; or be part of a heterocyclic ring comprising one or more heteroatoms wherein at least one of said heteroatoms is nitrogen;
C is selected from a hydroxymethine [—CH(OH)—], an acyloxymethine [—CH(OCOR')—], an olefin methine (=CH—), a carbonyl [—C(=O)—], an oxime [—C(=N—OH)—] or an hydrazone [—C(=N—NH$_2$)—], wherein R' is methyl;
D-E is a single or a double carbon-carbon bond;
F is selected from F$_1$, F$_2$ or F$_3$;

and wherein when F is F$_3$, F$_3$ is F$_{3b}$:

for use in the treatment of a condition or disease responsive to the activation of the HIF pathway.

The compounds of Formula (I) or analogs, derivatives, tautomeric forms, isomers, stereoisomers, polymorphs, pharmaceutically acceptable salts or pharmaceutically acceptable solvates thereof, described in present invention, show capacity to:
bind PHD2, as shown in Example 2 disclosed below herein,
stabilize HIF-1α and HIF-2α proteins, as shown in Example 4 disclosed below herein,
activate the HIF pathway in different cell types, as shown in Example 3 disclosed below herein,
induce angiogenesis in human endothelial vascular cell, as shown in Example 5 disclosed below herein,
show neuroprotective activity in vitro and in vivo, as shown in Example 7 disclosed below herein, and
increase the plasma levels of Erythropoietin in vivo, as shown in Example 6 disclosed below herein;
show antidiabetic activity and reduce the levels of lipids in vivo, as shown in Example 9 disclosed below herein.

Said triterpenoid derivatives act also in a selective manner and do not induce Nrf2 activation, NF-κB inhibition, STAT3 inhibition, and TGR5 activation, which are known activities of their natural triterpenoid precursors (as shown in Example 3 of present description).

Example 3 of present invention shows, as mentioned above, how the compounds of Formula (I) activate the HIF pathway in different cell types. Example 3 also tested two comparative compounds XX and CDDO-ME.

Comparative compound XX, derived from glycyrrethinic acid, comprises an hydroxamate group in position 20 and thus not in position 28 as the compounds of present invention.

(XX)

(3β) 3-Hydroxy-11-oxo-olean-12-en-N-hydroxy-29-amide

The results of Example 3 indicate that the change of the position of the hydroxamate, from the position 28 featured by the compounds of present invention, results in the absence of the activation of the HIF pathway.

On the other hand, comparative compound CDDO-Me (2-Cyano-3,12-dioxo-oleana-1,9(11)-dien-28-oic acid methyl ester, CAS num. 218600-53-4), is an oleanolic acid derivative, but which includes a cyano group in position 2 (substituent at the position B of Formula I) which is a substituent substantively different from the ones featured in said position by the compounds of Formula I disclosed in present invention.

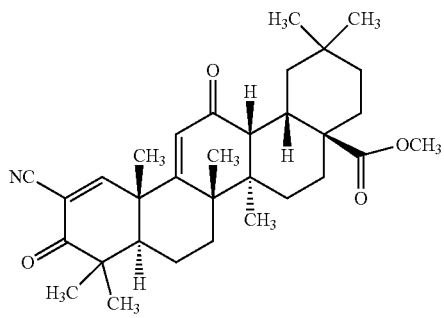

CDDO-Me

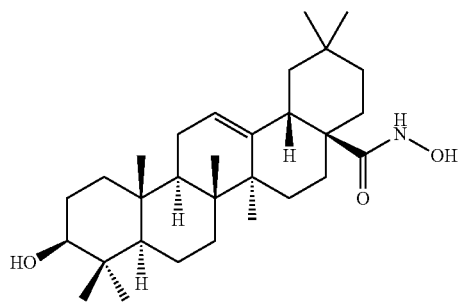

(3β) 3-Hydroxy-N-hydroxy-olean-12-en-28-amide (II)

The results of Example 3 show that CDDO-Me does not provide activation of the HIF pathway and thus, none of comparative compounds XX and CDDO-Me, which do not present the structural characteristics of the compounds of Formula I, provide activation of the HIF pathway.

Therefore, the triterpenoid derivatives defined by Formula I, disclosed in present invention, are useful in the treatment of conditions or diseases which are responsive to the activation of the HIF pathway, i.e., conditions or diseases the treatment of which benefits from HIF-1α and HIF-2α activation.

Particularly, one embodiment discloses the triterpene derivatives of Formula (I) described above herein for use in the treatment of conditions or diseases which are responsive to the activation of the HIF pathway, which comprise but are not limited to stroke, cerebral palsy, traumatic injuries and neurodegenerative diseases. Examples of neurodegenerative diseases include but are not limited to Multiple Sclerosis, Huntington disease, Alzheimer disease or Parkinson disease.

Another embodiment discloses the triterpene derivatives of Formula (I) described above herein, for use in the treatment of conditions or diseases which are responsive to the activation of the HIF pathway, which comprise but are not limited to IBD, myocardial ischaemia-reperfusion injury, acute lung injury, diabetic and chronic wounds, organ transplantation, acute kidney injury or arterial diseases. More preferably said condition or disease is selected from IBD, myocardial ischaemia-reperfusion injury, acute lung injury, organ transplantation, acute kidney injury or arterial diseases.

One embodiment of present invention, also discloses the compounds of Formula (I), as described above herein, for use in the treatment of a condition or disease responsive to the activation of the HIF pathway wherein said condition or disease responsive to the activation of the HIF pathway a metabolic pathology. In a preferred embodiment said metabolic pathology is diabetes. In another preferred embodiment said metabolic pathology is a lipid metabolism disorder. In yet another preferred embodiment said metabolic pathology is hyperlipidemia. In another preferred embodiment said metabolic pathology is hypertriglyceridemia.

Another embodiment disclosed herein refers to the compounds of Formula (I) or analogs, derivatives, tautomeric forms, isomers, stereoisomers, polymorphs, pharmaceutically acceptable salts or pharmaceutically acceptable solvates thereof selected from (II), (III), (IV), (V), (VI), (VII), (VIII), (IX), (X), (XI), (XII), (XIII), (XIV) or (XV).

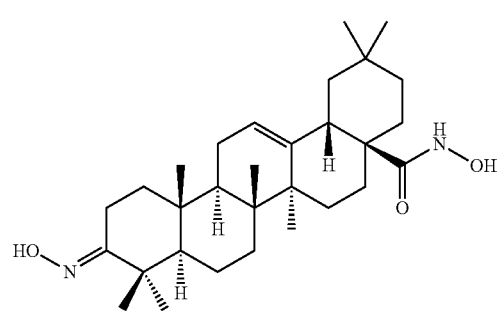

3-Hydroxyimino-N-hydroxy-olean-12-en-28-amide (III)

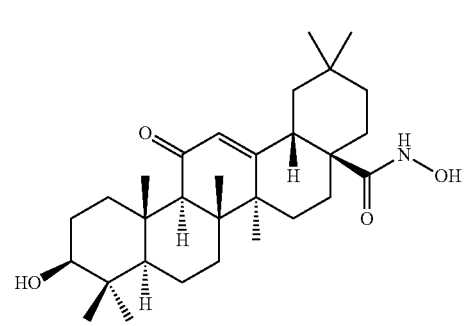

(3β) 3-Hydroxy-11-oxo-olean-12-en-N-hydroxy-28-amide (IV)

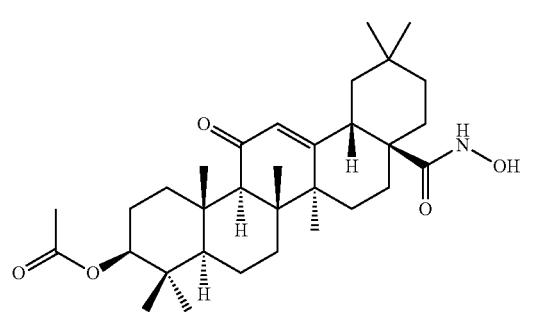

(3β) 3-Acetyloxy-11-oxo-olean-12-en-N-hydroxy-28-amide (V)

-continued
(VI)
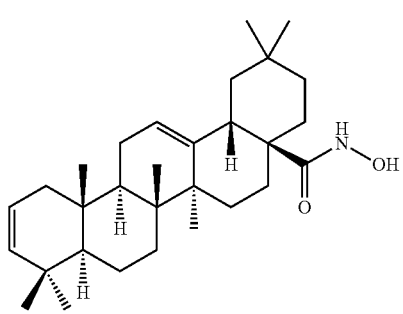
Oleana-2,12-dien-N-hydroxy-28-amide
(VII)
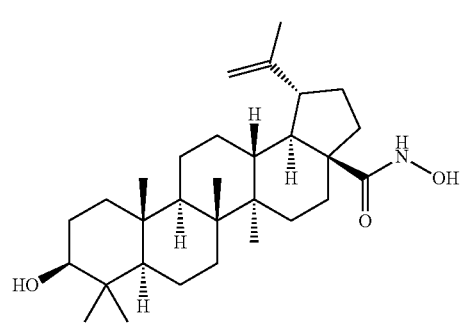
(3β) 3-Hydroxy-N-hydroxy-lup-20(29)-en-28-amide
(VIII)
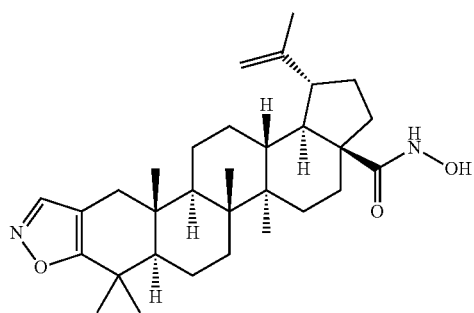
Lup-2-eno[2,3-d]isoxazol-N-hydroxy-28-amide
(IX)
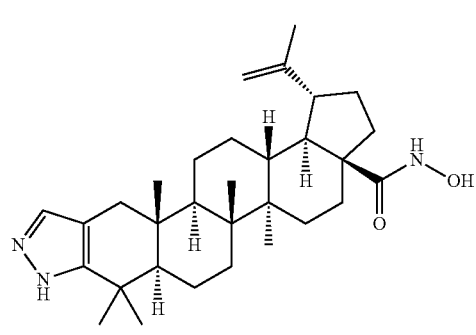
1′H-Lup-20(29)-eno[3,2-c] pyrazol-N-hydroxy-28-amide
-continued
(X)
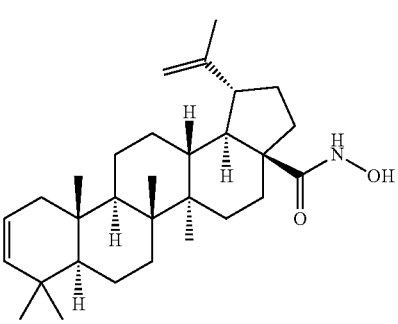
Lupa-2,20(29)-dien-N-hydroxy-28-amide
(XI)
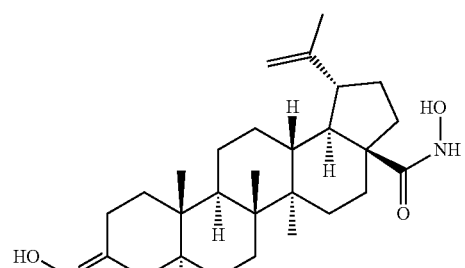
3-Hydroxyimino-N-hydroxy-lup-20(29)-en-28-amide
(XII)
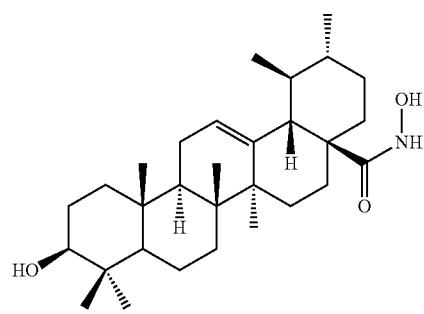
(3β) 3-Hydroxy-N-hydroxy-urs-12-en-28-amide
(XIII)
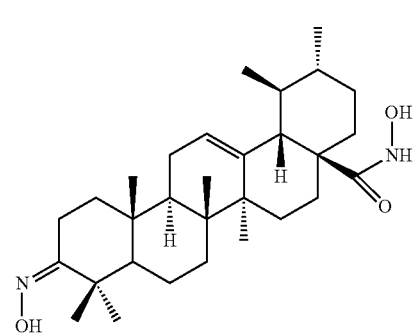
3-Hydroxyimino-N-hydroxy-urs-12-en-28-amide

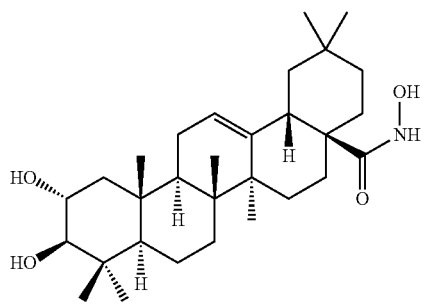

(2α,3β) 2,3-Dihydroxy-N-hydroxy-olean-12-en-28-amide

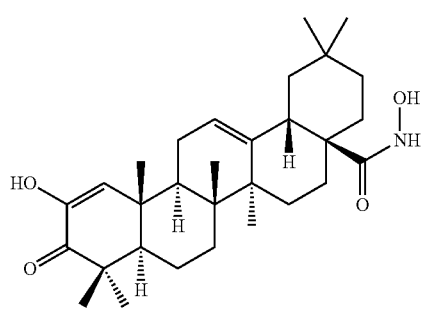

2-Hydroxy-3-oxo-oleana-1,12-dien-N-hydroxy-28-amide for use in the treatment of conditions or diseases responsive to the activation of the HIF pathway. A preferred embodiment refers to the compounds of Formula (I) or analogs, derivatives, tautomeric forms, isomers, stereoisomers, polymorphs, pharmaceutically acceptable salts or pharmaceutically acceptable solvates thereof selected from (II), (III), (IV), (V), (VI), (VII), (VIII), (X), (XI), (XII), (XIII), (XIV) or (XV) for use in the treatment of conditions or diseases responsive to the activation of the HIF pathway.

The above mentioned compounds II to XV, or analogs, derivatives, tautomeric forms, isomers, stereoisomers, polymorphs, pharmaceutically acceptable salts or pharmaceutically acceptable solvates thereof, show capacity to bind PHD2, stabilize HIF-1α and HIF-2α proteins, activate the HIF pathway in different cell types, induce angiogenesis in human endothelial vascular cell, show neuroprotective activity in vitro and in vivo, antidiabetic activity and reduce levels of lipids in vivo, and increase the plasma levels of Erythropoietin in vivo. Said compounds of Formula (I) or analogs, derivatives, tautomeric forms, isomers, stereoisomers, polymorphs, pharmaceutically acceptable salts or pharmaceutically acceptable solvates thereof, act in a selective manner and do not induce Nrf2 activation, NF-κB inhibition, STAT3 inhibition, and TGR5 activation, which are known activities of their natural triterpenoid precursors.

As shown in Example 1, starting from a known derivative of a natural triterpenic acid (betulinic, oleanolic, ursolic, or maslinic acids) or a natural triterpenic acid itself, and ending with the compounds of general Formula (I), a common synthetic route was used to convert the acid group of position 28 into the hydroxamate derivative, wherein, depending on the functionalization of the final compound of Formula (I) other extra synthetic steps were carried out for each of the specific compounds of Formula (I).

Compounds III to VI of present invention can be synthesized starting from known derivatives of natural oleanolic acid. Compounds VIII to XI of the present invention can be synthesized by starting from natural betulinic acid or a known derivative thereof. Compounds XIV and XV of the present invention can be synthesized starting from a known derivative of natural maslinic acid.

Example 1 also describes compounds XVII and XVIII, and XIX that are novel compounds intermediate in the synthesis of compounds XV and XIV respectively.

Another embodiment disclosed herein refers to the pharmaceutical compositions comprising at least one triterpene derivative of Formula (I) or analogs, derivatives, tautomeric forms, isomers, stereoisomers, polymorphs, pharmaceutically acceptable salts or pharmaceutically acceptable solvates thereof, Formula (I)

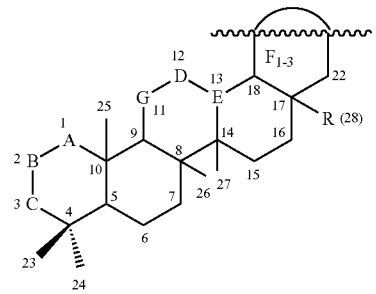

wherein independently,

A-B is selected from a single carbon-carbon bond or a double carbon-carbon bond;

B is selected from a methylene (—CH$_2$—), an olefin methine (=CH—), a hydroxymethine [—CH(OH)—], or a hydroxylated olefin carbon [—C(OH)=];

B-C is selected from a single carbon-carbon bond or a double carbon-carbon bond; or be part of a heterocyclic ring comprising one or more heteroatoms wherein at least one of said heteroatoms is nitrogen;

C is selected from a hydroxymethine [—CH(OH)—], an acyloxymethine [—CH(OCOR')—], an olefin methine (=CH—), a carbonyl [—C(=O)—], an oxime [—C(=N—OH)—] or an hydrazone [—C(=N—NH$_2$)—], wherein R' is methyl;

D-E is a single or a double carbon-carbon bond;

F is selected from F$_1$, F$_2$ or F$_3$;

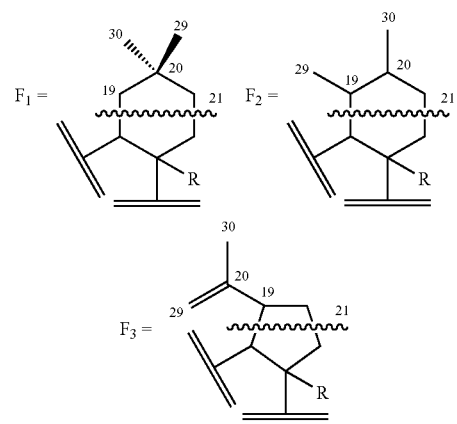

G is selected from a methylene (—CH$_2$—) or a carbonyl [—C(=O)—]; and

R is a hydroxamate group (—CONHOH);

for use in the treatment of conditions or diseases responsive to the activation of the HIF pathway.

In one embodiment of the pharmaceutical compositions comprising the triterpene derivatives of Formula (I), as disclosed above herein, B-C can be part of a heterocyclic ring comprising one or more heteroatoms wherein at least one of said heteroatoms is nitrogen, and wherein said heterocyclic ring is a five-membered ring.

In one embodiment of the pharmaceutical compositions comprising the triterpene derivatives of Formula (I), as disclosed above herein, B-C can be part of a heterocyclic ring comprising one or more heteroatoms wherein at least one of said heteroatoms is nitrogen, and wherein said heterocyclic ring is a five-membered ring comprising two nitrogen atoms.

In one embodiment of the pharmaceutical compositions comprising the triterpene derivatives of Formula (I), as disclosed above herein, B-C can be part of a heterocyclic ring comprising one or more heteroatoms wherein at least one of said heteroatoms is nitrogen, and wherein said heterocyclic ring is a five-membered ring comprising one nitrogen and one oxygen.

In one embodiment of the triterpene derivatives of Formula (I), when C is an acyloxymethine [—CH(OCOR')—], the triterpene derivative of Formula (I) is

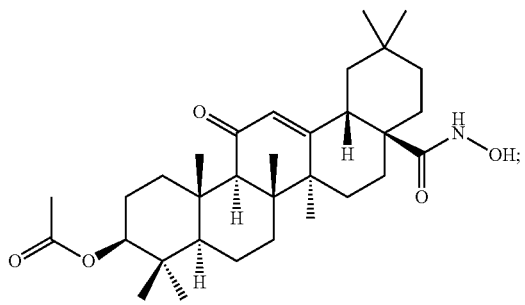

(V)

(3β) 3-Acetyloxy-11-oxo-olean-12-en-N-hydroxy-28-amide

Said pharmaceutical compositions comprising compounds of Formula (I) or analogs, derivatives, tautomeric forms, isomers, stereoisomers, polymorphs, pharmaceutically acceptable salts or pharmaceutically acceptable solvates thereof, show capacity to bind PHD2, stabilize HIF-1α and HIF-2α proteins, activate the HIF pathway in different cell types, induce angiogenesis in human endothelial vascular cell, show neuroprotective activity in vitro and in vivo, antidiabetic activity and reduce the levels of lipids in vivo, and increase the plasma levels of Erythropoietin in vivo. Said compositions comprising compounds of Formula (I) or analogs, derivatives, tautomeric forms, isomers, stereoisomers, polymorphs, pharmaceutically acceptable salts or pharmaceutically acceptable solvates thereof, act in a selective manner and do not induce Nrf2 activation, NF-κB inhibition, STAT3 inhibition, and TGR5 activation, which are known activities of their natural triterpenoid precursors.

Another embodiment disclosed herein refers to the pharmaceutical compositions comprising at least one triterpene derivative of Formula (I) or analogs, derivatives, tautomeric forms, isomers, stereoisomers, polymorphs, pharmaceutically acceptable salts or pharmaceutically acceptable solvates thereof, as described above herein, for use in the treatment of conditions or diseases responsive to the activation of the HIF pathway, which comprise but are not limited to stroke, cerebral palsy, traumatic injuries and neurodegenerative diseases; or for use in the treatment of conditions or diseases responsive to the activation of the HIF pathway, which comprise but are not limited to IBD, myocardial ischaemia-reperfusion injury, acute lung injury, diabetic and chronic wounds, organ transplantation, acute kidney injury or arterial diseases. More preferably said condition or disease is selected from IBD, myocardial ischaemia-reperfusion injury, acute lung injury, organ transplantation, acute kidney injury or arterial diseases.

Another embodiment disclosed herein refers to the pharmaceutical compositions comprising at least one triterpene derivative of Formula (I) or analogs, derivatives, tautomeric forms, isomers, stereoisomers, polymorphs, pharmaceutically acceptable salts or pharmaceutically acceptable solvates thereof, as described above herein, for use in the treatment of a condition or disease responsive to the activation of the HIF pathway wherein said condition or disease responsive to the activation of the HIF pathway a metabolic pathology. In a preferred embodiment said metabolic pathology is diabetes. In another preferred embodiment said metabolic pathology is a lipid metabolism disorder. In yet another preferred embodiment said metabolic pathology is hyperlipidemia. In another preferred embodiment said metabolic pathology is hypertriglyceridemia.

Said compositions may further comprise another active ingredient which exerts therapeutic effects when administered to human or animal beings.

Typical compositions include the compounds of Formula (I), or analogs, derivatives, tautomeric forms, isomers, stereoisomers, polymorphs, pharmaceutically acceptable salts or pharmaceutically acceptable solvates thereof, described above herein associated with pharmaceutically acceptable excipients, which may be a carrier or a diluent, as a way of example. Such compositions can be in the form of a capsule, sachet, paper or other container. In making the compositions, conventional techniques for the preparation of pharmaceutical compositions may be used. For example, the compounds of Formula (I) disclosed above herein may be mixed with a carrier, or diluted by a carrier, or enclosed within a carrier that may be in the form of an ampoule, capsule, sachet, paper, or other container. When the carrier serves as a diluent, it may be solid, semi-solid, or liquid material that acts as a vehicle, excipient, or medium for the active compound. The compounds of Formula (I) as described above herein can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. Said compositions may also include wetting agents, emulsifying and suspending agents, preserving agents, sweetening agents or flavouring agents. The compositions of the invention may be formulated so as to provide quick, sustained, or delayed release of the compounds of Formula (I) disclosed herein after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the compounds disclosed above herein.

One preferred embodiment disclosed herein refers to the route of administration, that may be any route which effectively transports the compound of Formula (I) or analogs, derivatives, tautomeric forms, isomers, stereoisomers, polymorphs, pharmaceutically acceptable salts or pharmaceutically acceptable solvates thereof, disclosed above herein, to the appropriate or desired site of action, such as oral, nasal, topical, pulmonary, transdermal or parenteral, e. g., rectal, subcutaneous, intravenous, intraurethral, intramuscular, intranasal, ophthalmic solution or an ointment.

For nasal administration, the compositions may contain the compound of Formula (I) or analogs, derivatives, tautomeric forms, isomers, stereoisomers, polymorphs, pharmaceutically acceptable salts or pharmaceutically acceptable solvates thereof, disclosed above herein, dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine), or cyclodextrin, or preservatives such as parabens.

To prepare topical compositions, the compound of Formula (I) or analogs, derivatives, tautomeric forms, isomers, stereoisomers, polymorphs, pharmaceutically acceptable salts or pharmaceutically acceptable solvates thereof, disclosed above herein, is placed in a dermatological vehicle as is known in the art. The amount of the compound of Formula (I) or analogs, derivatives, tautomeric forms, isomers, stereoisomers, polymorphs, pharmaceutically acceptable salts or pharmaceutically acceptable solvates thereof, disclosed above herein to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the compound of Formula (I) or analogs, derivatives, tautomeric forms, isomers, stereoisomers, polymorphs, pharmaceutically acceptable salts or pharmaceutically acceptable solvates thereof, disclosed above herein, and selects the amount of formulation administered, depending upon clinical experience with the patient in question or with similar patients.

For ophthalmic applications, the compound of Formula (I) or analogs, derivatives, tautomeric forms, isomers, stereoisomers, polymorphs, pharmaceutically acceptable salts or pharmaceutically acceptable solvates thereof, disclosed above herein, is formulated into solutions, suspensions, and ointments appropriate for use in the eye. The concentrations are usually as discussed above herein for local preparations.

For oral administration, either solid or fluid unit dosage forms can be prepared. For preparing solid compositions such as tablets, the compound of Formula (I) or analogs, derivatives, tautomeric forms, isomers, stereoisomers, polymorphs, pharmaceutically acceptable salts or pharmaceutically acceptable solvates thereof, disclosed above herein, is mixed into formulations with conventional ingredients such as talc, magnesium stearate, di-calcium phosphate, magnesium aluminum silicate, calcium sulfate, starch, lactose, acacia, methylcellulose, and functionally similar materials as pharmaceutical diluents or carriers.

Capsules are prepared by mixing the compound of Formula (I) or analogs, derivatives, tautomeric forms, isomers, stereoisomers, polymorphs, pharmaceutically acceptable salts or pharmaceutically acceptable solvates thereof, disclosed above herein with an inert pharmaceutical diluent, and filling the mixture into a hard gelatin capsule of appropriate size. Soft gelatin capsules are prepared by machine encapsulation of slurry of the compound of Formula (I) with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form syrup. An elixir is prepared by using a hydroalcoholic (e. g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate compositions for parenteral use are apparent to the practitioner of ordinary skill, such as the use of suitable injectable solutions or suspensions. The composition, which is sterile, is suitable for various topical or parenteral routes including intra-dermal, intramuscular, intravascular, and subcutaneous.

In addition to the compound of Formula (I) or analogs, derivatives, tautomeric forms, isomers, stereoisomers, polymorphs, pharmaceutically acceptable salts or pharmaceutically acceptable solvates thereof, disclosed above herein, the compositions may include, depending on the composition and mode of delivery desired, pharmaceutically-acceptable, non-toxic carriers or diluents, which include vehicles commonly used to form pharmaceutical compositions for animal or human administration. The diluents are selected so as not to unduly affect the biological activity of the combination.

Examples of such diluents that are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or non-toxic, non-therapeutic, non-immunogenic stabilizers and the like.

Furthermore, excipients can be included in the compositions disclosed. Examples include but are not limited to cosolvents, surfactants, oils, humectants, emollients, preservatives, stabilizers and antioxidants. Any pharmacologically acceptable buffer may be used, such as, tris or phosphate buffers. Effective amounts of diluents, additives, and excipients are those amounts that are effective to obtain a pharmaceutically acceptable formulation in terms of solubility, biological activity, etc.

The pharmaceutical compositions comprising the compound of Formula (I) or analogs, derivatives, tautomeric forms, isomers, stereoisomers, polymorphs, pharmaceutically acceptable salts or pharmaceutically acceptable solvates thereof, disclosed above herein may be incorporated into a microsphere. The compound of Formula (I) or analogs, derivatives, tautomeric forms, isomers, stereoisomers, polymorphs, pharmaceutically acceptable salts or pharmaceutically acceptable solvates thereof, disclosed above herein can be loaded into albumin microspheres, from which it is possible to recover such microspheres in a dry powder for nasal administration. Other materials suitable for the preparation of microspheres include agar, alginate, chitosan, starch, hydroxyethyl starch, albumin, agarose, dextran, hyaluronic acid, gelatin, collagen, and casein. The microspheres can be produced by various processes known to the person skilled in the art such as a spray drying process or an emulsification process.

For example, albumin microspheres can be prepared by adding rabbit serum albumin in phosphate buffer to olive oil with stirring to produce water in oil emulsion. Glutaraldehyde solution is then added to the emulsion and the emulsion stirred to cross-link the albumin. The microspheres can then be isolated by centrifugation, the oil removed and the spheres washed, e. g., with petroleum ether followed by ethanol. Finally, the microspheres can be sieved and collected and dried by filtration.

Starch microspheres can be prepared by adding a warm aqueous starch solution, e. g. of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurred in a solvent such as ethanol, after which the particles are again filtered off and laid to dry in air. The microspheres can be hardened by well-known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative.

Another preferred embodiment of the invention is the dosage scheme of the compounds of Formula (I) or analogs, derivatives, tautomeric forms, isomers, stereoisomers, polymorphs, pharmaceutically acceptable salts or pharmaceutically acceptable solvates thereof, and of the compositions comprising said compounds, as described above herein. The term "unit dosage form" refers to physically discrete units suitable as unitary dosages for subjects, e.g., mammalian subjects, e. g. humans, dogs, cats, and rodents, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the compound of Formula (I) or analogs, derivatives, tautomeric forms, isomers, stereoisomers, polymorphs, pharmaceutically acceptable salts or pharmaceutically acceptable solvates thereof, disclosed above herein and the particular effect to be achieved and (b) the limitations inherent in the art of compounding said compound of Formula (I) for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions disclosed herein can be included in kits, which can contain one or more-unit dosage forms of the composition and instructions for use to treat one or more of the diseases described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long-term source of therapeutic compound. Such slow release systems are applicable to formulations for delivery via topical, intraocular, oral, and parenteral routes.

An effective amount of the compound of Formula (I) or analogs, derivatives, tautomeric forms, isomers, stereoisomers, polymorphs, pharmaceutically acceptable salts or pharmaceutically acceptable solvates thereof, as described above herein, is comprised in the compositions. The dosage of compounds used in accordance with the invention varies depending on the compound and the condition being treated for example the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

One embodiment disclosed herein refers to a method of use of the compounds of Formula (I) or analogs, derivatives, tautomeric forms, isomers, stereoisomers, polymorphs, pharmaceutically acceptable salts or pharmaceutically acceptable solvates thereof, in the treatment of conditions or diseases responsive to the activation of the HIF pathway.

Said compounds of Formula (I) or analogs, derivatives, tautomeric forms, isomers, stereoisomers, polymorphs, pharmaceutically acceptable salts or pharmaceutically acceptable solvates thereof, show capacity to bind PHD2, stabilize HIF-1$\alpha$ and HIF-2$\alpha$ proteins, activate the HIF pathway in different cell types, induce angiogenesis in human endothelial vascular cell, show neuroprotective activity in vitro and in vivo, antidiabetic activity and reduce the levels of lipids in vivo, and increase the plasma levels of Erythropoietin in vivo. Said compounds of Formula (I) or analogs, derivatives, tautomeric forms, isomers, stereoisomers, polymorphs, pharmaceutically acceptable salts or pharmaceutically acceptable solvates thereof, act in a selective manner and do not induce Nrf2 activation, NF-$\kappa$B inhibition, STAT3 inhibition, and TGR5 activation, which are known activities for their natural triterpenoid precursors.

Another embodiment disclosed herein refers to a method of use of the compounds of Formula (I) for treating diseases responsive to the activation of the HIF pathway such as IBD, myocardial ischaemia-reperfusion injury, acute lung injury, diabetic and chronic wounds, organ transplantation, acute kidney injury or arterial diseases. In a preferred embodiment said diseases are selected from IBD, myocardial ischaemia-reperfusion injury, acute lung injury, organ transplantation, acute kidney injury or arterial diseases.

Another embodiment disclosed herein refers to a method of use of the compounds of Formula (I) in the treatment of a condition or disease responsive to the activation of the HIF pathway, selected from to stroke, cerebral palsy, traumatic injuries or neurodegenerative diseases.

One embodiment disclosed herein refers to a method of treatment of a condition or disease responsive to the activation of the HIF pathway selected from IBD, myocardial ischaemia-reperfusion injury, acute lung injury, diabetic and chronic wounds, organ transplantation, acute kidney injury or arterial diseases, said method comprising administering an effective amount of a compound of Formula (I) or analogs, derivatives, tautomeric forms, isomers, stereoisomers, polymorphs, pharmaceutically acceptable salts or pharmaceutically acceptable solvates thereof, as described above herein, to an individual in need of said treatment. In a preferred embodiment said diseases are selected from IBD, myocardial ischaemia-reperfusion injury, acute lung injury, organ transplantation, acute kidney injury or arterial diseases.

Another embodiment disclosed herein refers to a method of treatment of a condition or disease responsive to the activation of the HIF pathway, said method comprising administering an effective amount of a compound of Formula (I) or analogs, derivatives, tautomeric forms, isomers, stereoisomers, polymorphs, pharmaceutically acceptable salts or pharmaceutically acceptable solvates thereof, as described above herein, to an individual in need of said treatment.

In one embodiment disclosed herein, condition or disease responsive to the activation of the HIF pathway include but are not limited to stroke, cerebral palsy, traumatic injuries and neurodegenerative diseases. Examples of neurodegenerative diseases include but are not limited to Alzheimer disease, Parkinson disease, Huntington disease or Multiple Sclerosis.

EXAMPLES

Figure 1:
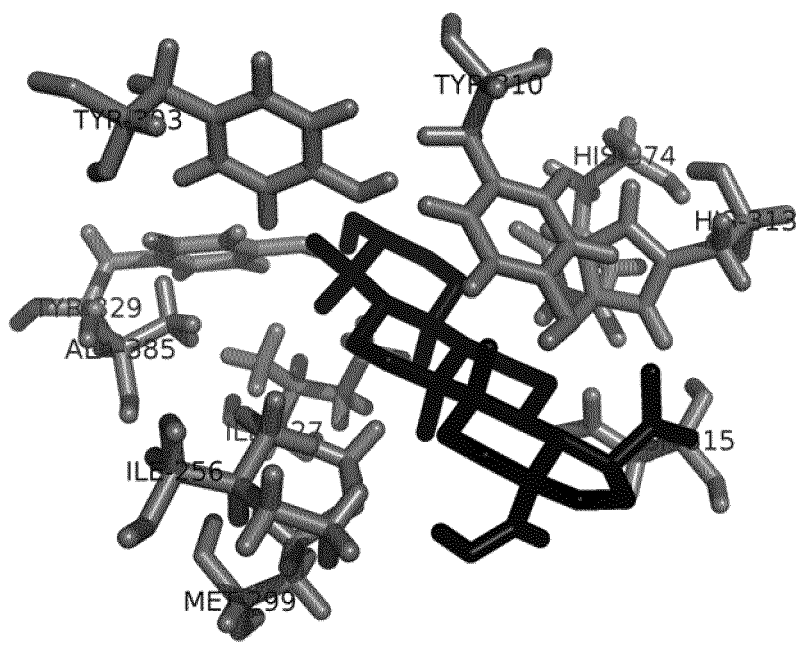
FIG. 1. Top scored conformation of betulinic acid (FIG. 1A) and compound VII (FIG. 1B) bound to PHD2 (PDB 4BQW).
Figure 1:
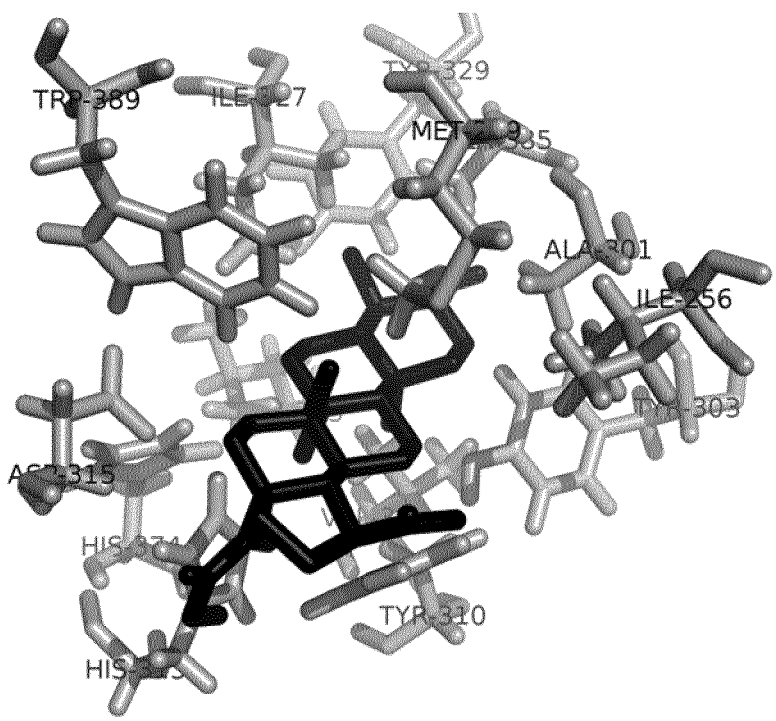

The examples of the present invention described below aim to illustrate its preferred embodiments without limiting its scope of protection.

Example 1. Synthesis of the Triterpenoid Derivatives of Formula (I) and of Comparative Compound XX General Synthesis of the N-Hydroxy-Triterpen-28-Amide Derivatives of Formula (I) (Hydroxamate Formation):

To an ice-cold solution of a triterpenic acid precursor (1 eq/mol) in dry dichloromethane (DCM), oxalyl chloride (6 eq/mol) was added dropwise, and the mixture was heated at 40° C. for 1.5 hours. The solvent was removed in vacuum, the residue was dissolved in dry pyridine or N,N-diisopropylethylamine (DiPEA), and hydroxylammonium chloride (6 eq/mol) were added. The reaction was heated at 40° C. for 3 hours, quenched with 2 N $H_2SO_4$ sol. and extracted with EtOAc. The organic phases were washed with brine, dried over $Na_2SO_4$ and evaporated under vacuum. The crude compound was purified over silica gel.

Known compounds are identified when possible with means of their CAS number.

(3β) 3-Hydroxy-N-hydroxy-olean-12-en-28-amide (Compound II)

CAS num.: 1854922-22-7
Off-white solid (60%). $^1H$ NMR (300 MHz, $CDCl_3$): d: $^1H$ NMR (300 MHz, $CDCl_3$): d=5.41 (brt, 1H, H-12), 3.19 (dd, J=10.0, 4.89 Hz, 1H), 2.44 (d, J=10.8 Hz, 1H), 2.05-1.86 (m, 3H), 1.16 (s, 3H), 0.98 (s, 3H), 0.92 (s, 3H), 0.90 (s, 3H), 0.88 (s, 3H), 0.81 (s, 3H), 0.78 (s, 3H) (only readily peaks are reported); $^{13}C$ NMR (75 MHz, $CDCl_3$): d=176.7, 144.9, 123.9, 78.9, 55.2, 47.6, 46.4, 45.5, 42.0, 40.8, 39.5, 38.8, 38.6, 37.0, 34.0, 32.9, 32.3, 32.0, 30.7, 28.1, 27.3, 27.2, 25.84, 23.7, 23.6, 23.5, 18.3, 16.7, 15.6, 15.4.

3-Hydroxyimino-N-hydroxy-olean-12-en-28-amide (Compound III)

Compound III was obtained according to the general synthetic scheme described above herein (hydroxamate formation), starting from the known precursor CAS num. 17990-42-0:

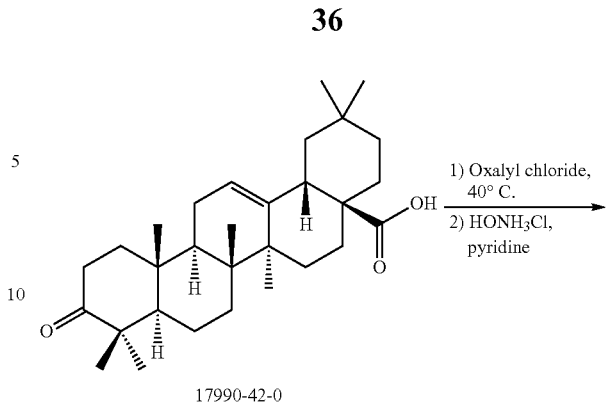

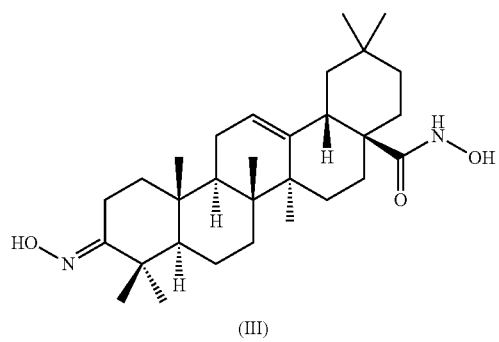

The oxime formation featured in position C of compound III was carried out as well as the hydroxamate formation during the same general synthetic path.

Off-white solid (70%). $^1H$ NMR (300 MHz, $CDCl_3$): d=5.43 (brt, 1H), 3.07 (bdt, J=14.9, 1H), 2.46 (m, 1H), 1.98 (m, 3H), 1.13 (s, 10H), 1.07 (s, 6H), 1.05 (s, 3H), 0.86 (s, 6H), 0.82 (s, 3H) (only readily peaks are reported); $^{13}C$ NMR (75 MHz, $CDCl_3$) d=176.7, 167.5, 144.9, 123.8, 55.7, 47.1, 46.2, 45.5, 42.0, 40.8, 40.3, 39.4, 38.4, 37.0, 33.9, 32.9, 31.9, 30.7, 29.7, 29.2, 27.2, 25.7, 25.5, 23.7, 23.5, 23.4, 19.0, 17.3, 16.7, 14.9.

(3β) 3-Acetyloxy-11-oxo-olean-12-en-N-hydroxy-28-amide (Compound V)

Compound V was obtained according to the general synthetic scheme described above herein (hydroxamate formation), from the known precursor CAS num. 14605-17-5:

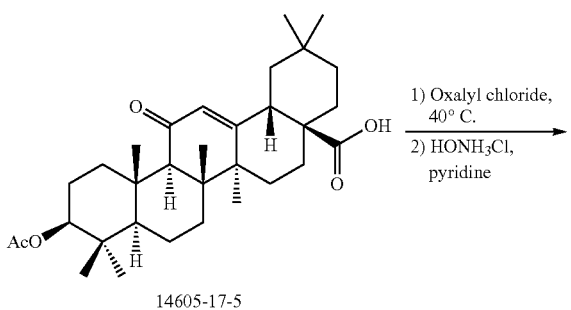

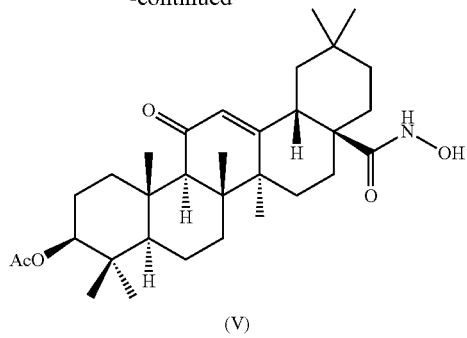

(V)

Pale yellow solid (75%). $^1$H NMR (300 MHz, CDCl$_3$): d=5.65 (s, 1H), 4.47 (dd, J=4.8 J=11.0 Hz, 1H), 3.31 (m, 1H), 2.76 (t, J=12.5 Hz, 2H), 2.32 (s, 1H), 2.00 (s, 3H), 1.12 (s, 3H), 0.91 (s, 3H), 0.88 (s, 6H), 0.82 (s, 9H) (only readily peaks are reported); $^{13}$C NMR (75 MHz, CDCl$_3$) d=200.5, 174.4, 171.2, 168.4, 127.8, 80.7, 61.9, 55.0, 45.3, 44.8, 43.6, 43.0, 40.7, 38.7, 38.0, 37.1, 33.8, 32.8, 32.6, 32.1, 30.7, 28.1, 27.3, 23.6, 23.5, 23.4, 23.1, 21.3, 19.0, 17.3, 16.7, 16.3.

(3β) 3-Hydroxy-11-oxo-olean-12-en-N-hydroxy-28-amide (Compound IV)

To obtain compound IV, the deacetylation of compound V was carried out as follows:

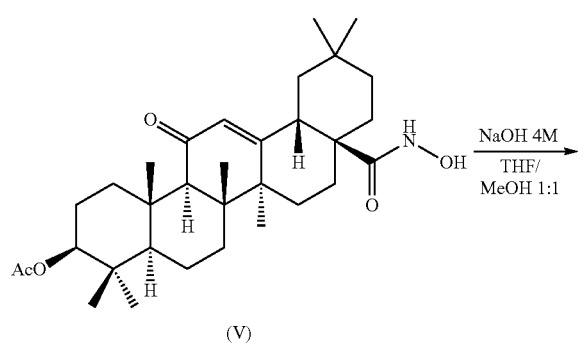

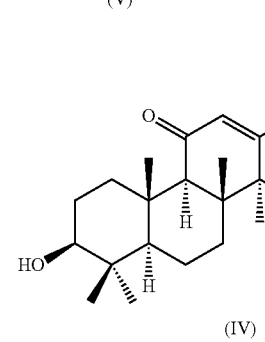

(IV)

To a solution of compound V, (3β) 3-Acetyloxy-11-oxo-olean-12-en-N-hydroxy-28-amide (1 eq/mol) in THF/MeOH 1:1 was added NaOH 4N (50 eq/mol). The mixture was heated at 40° C. overnight, quenched with H$_2$SO$_4$ sol. 2N and extracted with EtOAc. The organic phases were washed with brine, dried over Na$_2$SO$_4$ and evaporated under vacuum. The crude compound was purified over silica gel.

Pale yellow solid (65%). $^1$H NMR (300 MHz, CDCl$_3$): d=5.67 (s, 1H), 3.20 (t, J=6.1 Hz, 1H), 2.74 (d, J=12.2 Hz, 2H), 2.32 (s, 1H), 2.10-2.02 (m, 1H), 1.18 (s, 3H), 0.96 (s, 3H), 0.94 (s, 3H), 0.90 (s, 9H), 0.77 (s, 3H) (only readily peaks are reported); $^{13}$C NMR (75 MHz, CDCl$_3$) d=200.2, 175.8, 167.9, 128.0, 78.8, 62.1, 55.0, 45.2, 44.7, 43.6, 40.9, 39.2, 37.3, 33.7, 32.8, 32.7, 32.1, 30.7, 29.7, 28.1, 27.4, 27.3, 23.7, 23.4, 23.3, 19.0, 17.5, 16.2, 15.6, 14.2.

Oleana-2,12-dien-N-hydroxy-28-amide (Compound VI)

Compound VI was obtained following the general synthetic scheme described above herein (hydroxamate formation), starting from the known precursor CAS num. 272108-04-0:

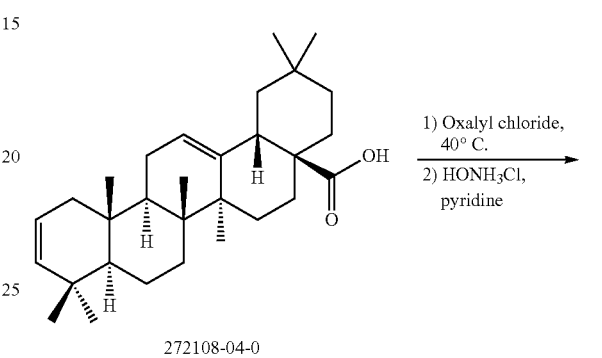

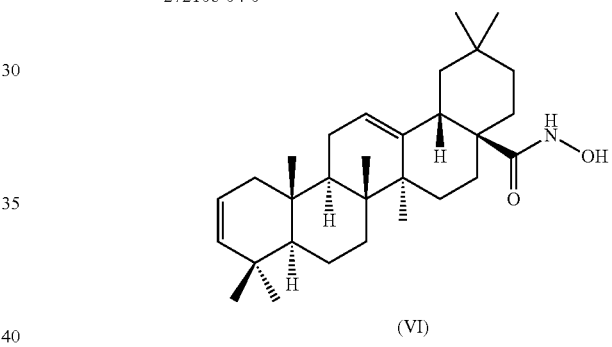

(VI)

Yellow oil (48%). $^1$H NMR (300 MHz, CDCl$_3$): d=5.43-5.32 (m, 3H), 2.44 (d, J=11.3 Hz, 1H), 1.14 (s, 3H), 0.97 (s, 6H), 0.87 (s, 12H) (only readily peaks are reported); $^{13}$C NMR (75 MHz, CDCl$_3$) d=176.4, 144.5, 138.0, 124.1, 121.3, 51.9, 46.4, 46.1, 45.5, 42.1, 41.0, 40.7, 39.5, 36.1, 34.5, 34.0, 33.0, 31.9, 31.8, 31.6, 30.7, 27.2, 25.9, 25.7, 23.8, 23.5, 22.9, 19.6, 16.3, 15.6.

(3β) 3-Hydroxy-N-hydroxy-lup-20(29)-en-28-amide (Compound VII)

CAS num.: 1822375-07-4

Off-white solid (55%). $^1$H NMR (300 MHz, CDCl$_3$): d: 4.73 (s, 1H), 4.60 (s, 1H), 3.20-3.15 (m, 1H), 3.05 (ddd, J=11.4, 6, 4.49 Hz, 1H), 1.67 (s, 3H), 0.95 (s, 6H), 0.92 (s, 3H), 0.80 (s, 3H), 0.74 (s, 3H) (only readily peaks are reported); $^{13}$C NMR (75 MHz, CDCl$_3$): d: 175.2, 150.9, 108.5, 78.4, 55.7, 54.3, 50.8, 50.7, 46.7, 42.3, 40.7, 38.7, 38.2, 37.8, 37.1, 36.9, 34.3, 32.6, 30.7, 29.3, 27.8, 26.9, 25.5, 20.8, 19.2, 18.2, 16.0, 15.9, 15.2, 14.5.

Lup-2-eno[2,3-d]isoxazol-N-hydroxy-28-amide (Compound VIII)

Compound VIII was obtained following the general synthetic scheme described above herein (hydroxamate formation), starting from the known precursor CAS num. 620958-43-2:

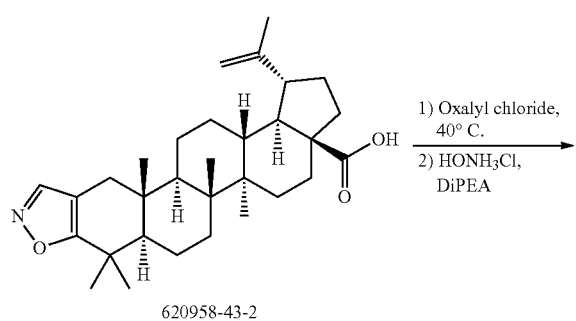

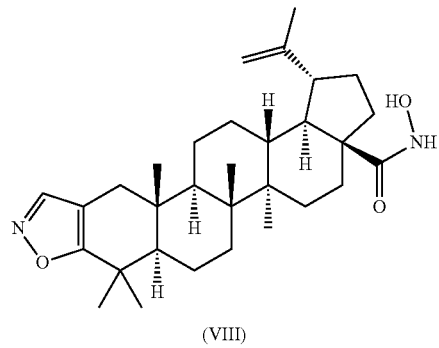

(VIII)

White solid. $^1$H NMR (300 MHz, CD$_3$OD): d=10.36 (s, 1H, NH), 8.32 (s, 1H, OH), 8.26 (s, 1H), 4.67 (s, 1H), 4.55 (s, 1H), 3.00 (t, J=9.3 Hz, 1H), 2.61 (t, J=12.0 Hz, 1H), 1.64 (s, 3H), 1.40 (s, 3H), 1.22 (s, 3H), 1.11 (s, 3H), 0.93 (s, 3H), 0.74 (s, 3H) (only readily peaks are reported); $^{13}$C NMR (75 MHz, CDCl$_3$) d=172.6, 151.3, 151.0, 109.9, 109.4, 54.0, 53.3, 50.6, 49.0, 48.9, 46.7, 42.4, 38.9, 37.3, 35.6, 34.8, 33.4, 32.6, 30.9, 29.0, 25.7, 21.7, 19.5, 18.7, 16.4, 16.2, 14.8.

1'H-Lup-20(29)-eno[3,2-c]pyrazol-N-hydroxy-28-amide (Compound IX)

Compound IX was obtained according to the general synthetic scheme described above herein (hydroxamate formation), starting from the known precursor CAS num. 1334386-31-0:

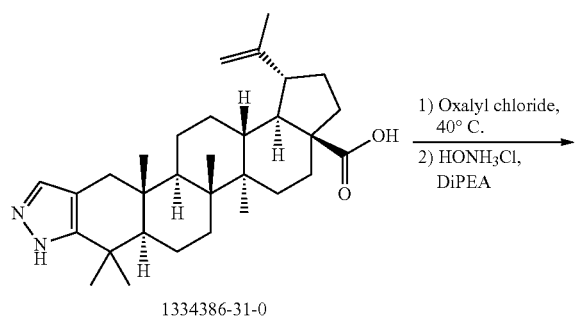

(IX)

Pale yellow solid. $^1$H NMR (300 MHz, (CD$_3$)$_2$CO): d=7.17 (s, 1H), 4.72 (s, 1H), 4.58 (s, 1H), 3.20-3.13 (m, 1H), 2.69-2.61 (m, 1H), 1.69 (s, 3H), 1.28 (s, 3H), 1.18 (s, 3H), 1.02 (s, 3H), 0.98 (s, 3H), 0.80 (s, 3H) (only readily peaks are reported); $^{13}$C NMR (75 MHz, (CD$_3$)$_2$CO) d=172.4, 151.0, 149.1, 132.8, 111.9, 109.0, 59.7, 50.0, 53.7, 50.5, 49.2, 46.8, 42.2, 40.7, 38.6, 37.9, 37.7, 36.6, 33.5, 33.4, 32.3, 30.8, 30.6, 25.7, 23.3, 21.4, 19.1, 18.7, 15.6, 14.2, 13.7.

Lupa-2,20(29)-dien-N-hydroxy-28-amide (Compound X)

Compound X was obtained according to the general synthetic scheme described above herein (hydroxamate formation), starting from the known precursor CAS num. 173106-19-9:

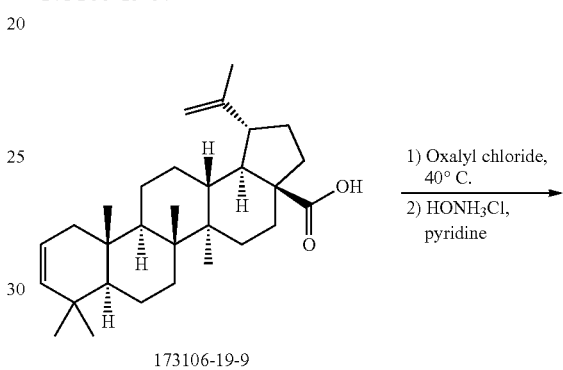

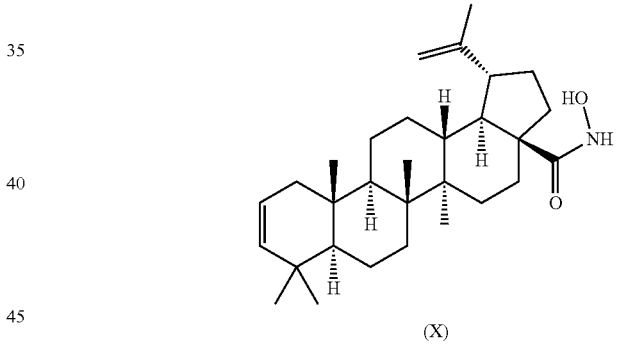

(X)

Pale yellow solid (54%) $^1$H NMR (300 MHz, CDCl$_3$): d=5.38-5.28 (m, 2H), 4.69 (s, 1H), 4.56 (s, 1H), 3.01 (t, J=10.7 Hz, 1H), 2.37 (t, J=12.1 Hz, 1H), 1.63 (s, 3H), 1.21 (s, 3H), 0.93 (s, 3H), 0.89 (s, 3H), 0.82 (s, 3H), 0.81 (s, 3H) (only readily peaks are reported); $^{13}$C NMR (75 MHz, CDCl$_3$) d=175.0, 150.5, 137.9, 121.6, 109.65, 54.3, 52.1, 50.4, 49.2, 42.3, 40.8, 38.4, 37.9, 36.4, 34.6, 33.5, 32.8, 31.7, 30.9, 30.8, 29.7, 29.3, 25.6, 22.6, 19.5, 16.4, 15.8, 14.6, 14.5, 14.3.

3-Hydroxyimino-N-hydroxy-lup-20(29)-en-28-amide—Step (b)—(Compound XI)

Prior to the general synthetic scheme described above herein (hydroxamate formation), the conversion of the hydroxyl group of the C-3 position of betulinic acid into a carbonyl group was carried out as follows:

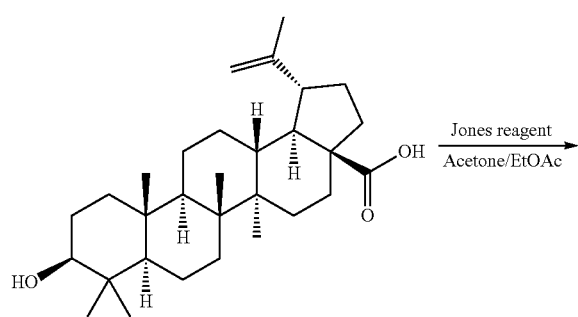
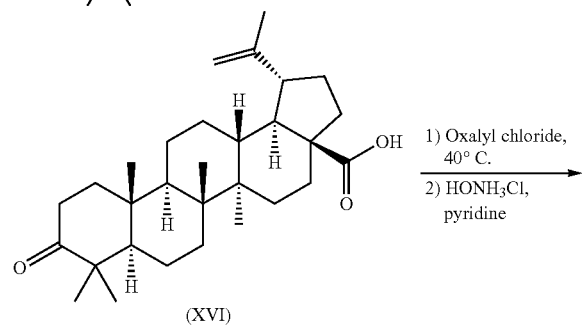
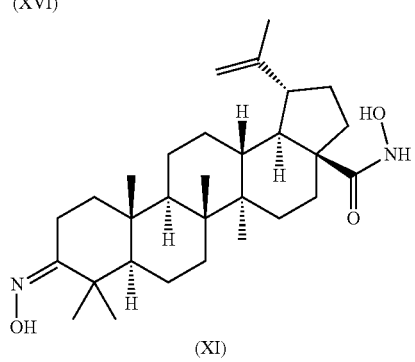

To a solution of betulinic acid (1 gr, 2.19 mmol) in acetone/EtOAc 5:5 (10 mL) was added Jones reagent until the disappearance of the starting material (control by TLC). The reaction was washed with brine and extracted with EtOAc. The organic phases were dried over $Na_2SO_4$ and evaporated under vacuum and the crude was purified over silica gel (PE/EtOAc 9:1), 3-Oxo-lup-20(29)-en-28-acid (compound XVI; CAS num.: 4481-62-3) (89%) as an off-white solid.

Compound XVI was then used to carry out the hydroxamate formation following the general synthetic scheme described above herein to obtain compound XI.

Off-white solid (65%). $^1$H NMR (300 MHz, $CDCl_3$): d=4.73 (s, 1H), 4.61 (t, J=6.1 Hz, 1H), 3.04-3.00 (m, 2H), 2.32 (s, 1H), 1.68 (s, 3H), 1.24 (s, 6H), 1.22 (s, 3H), 1.12 (s, 3H), 0.97 (s, 3H), 0.96 (s, 3H), 0.91 (s, 3H) (only readily peaks are reported); 177.3, 167.3, 150.5, 109.6, 55.6, 55.0, 50.3, 50.2, 46.8, 42.5, 40.8, 40.2, 38.7, 38.2, 37.9, 37.2, 34.0, 33.3, 30.8, 29.4, 27.4, 25.6, 22.9, 21.5, 21.2, 19.4, 19.1, 16.1, 15.8, 14.6.

(3β) 3-Hydroxy-N-hydroxy-urs-12-en-28-amide (Compound XII)

CAS num.: 915415-61-1
Off-white solid (55%). $^1$H NMR (300 MHz, $CDCl_3$): d=5.34 (brt, 1H, H-12), 3.18 (dd, J=9.5, 3.9 Hz, 1H), 2.09-1.92 (m, 3H), 1.06 (s, 3H), 0.94 (s, 3H), 0.90 (d, J=3.2 Hz, 3H), 0.87 (d, J=7.8 Hz, 3H), 0.80 (s, 3H), 0.78 (s, 3H), 0.75 (s, 3H) (only readily peaks are reported); $^{13}$C NMR (75 MHz, $CDCl_3$): d=176.8, 140.1, 126.6, 126.6, 79.0, 55.1, 52.2, 47.5, 42.4, 39.5, 39.5, 39.0, 38.8, 36.9, 28.1, 25.7, 23.3, 21.2, 17.2, 16.7, 15.7, 15.5.

3 Hydroxyimino-N-hydroxy-urs-12-en-28-amide (Compound XIII)

Compound disclosed in patent CN102180939. Said compound was prepared from ursolic acid carrying out an analogous synthesis to compound XI, wherein in a first step the conversion of the C-3 hydroxyl to carbonyl using Jones reagent is carried out, followed by the hydroxamate formation according to the general synthetic scheme described above herein to obtain compound XIII.

Pale yellow solid (70%). $^1$H NMR (300 MHz, $CDCl_3$): d=5.40 (brt, 1H), 3.07 (bdt, J=15.6, 1H), 2.12 (m, 1H), 1.24 (s, 3H), 1.15 (s, 3H), 1.08 (s, 3H), 1.06 (s, 3H), 1.03 (s, 3H), 0.94 (s, 3H), 0.81 (s, 3H) (only readily peaks are reported); $^{13}$C NMR (75 MHz, $CDCl_3$) d=177.3, 167.7, 140.6, 126.5, 55.7, 52.1, 47.0, 42.5, 40.2, 39.6, 39.4, 39.0, 38.5, 37.0, 36.7, 32.2, 30.6, 29.7, 27.7, 27.4, 24.8, 23.5, 23.4, 23.3, 21.1, 19.0, 17.3, 17.2, 16.8, 15.1.

(2α,3β) 2,3-Dihydroxy-N-hydroxy-olean-12-en-28-amide (Compound XIV)

Compound XIV was obtained according to the general synthetic scheme described above herein (hydroxamate formation), starting from the known precursor CAS num.: 6089-92-5

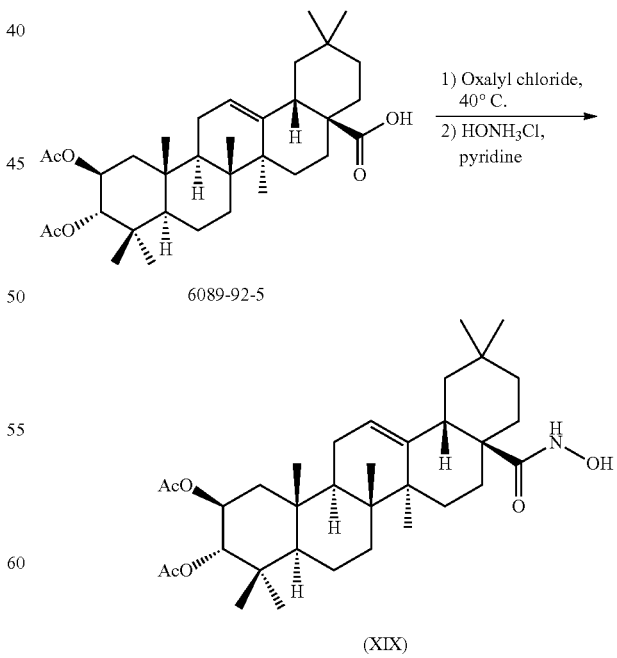

Compound XIX was deacetylated to obtain compound XIV:

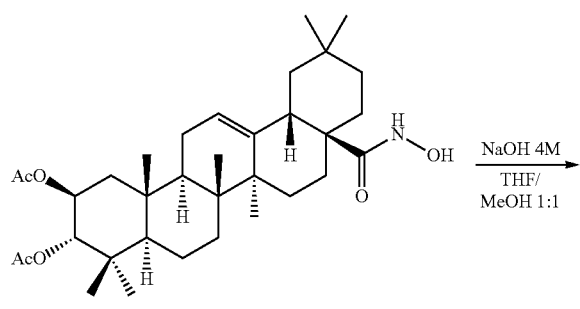

(XIX)

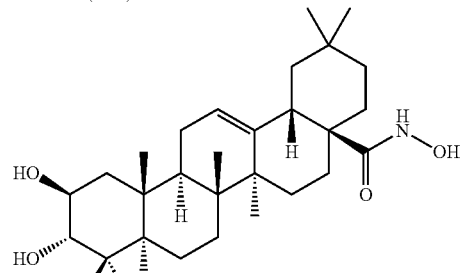

(XIV)

Off-white solid (45%). $^1$H NMR (300 MHz, CDCl$_3$): d=5.44 (brt, 1H), 3.72-3.61 (m, 1H), 2.99 (d, J=9.5 Hz, 1H), 2.45 (d, J=12.2 Hz, 1H), 1.15 (s, 3H), 1.02 (s, 3H), 0.98 (s, 3H), 0.90 (s, 3H), 0.87 (s, 3H), 0.82 (s, 3H), 0.78 (s, 3H) (only readily peaks are reported); $^{13}$C NMR (75 MHz, CDCl$_3$): d=175.9, 144.0, 123.6, 83.7, 68.2, 55.0, 47.3, 46.2, 46.1, 45.6, 41.2, 41.0, 39.0, 38.7, 37.8, 33.6, 32.6, 32.4, 32.3, 31.4, 28.5, 27.4, 27.3, 23.2, 23.1, 22.8, 18.6, 16.3, 16.5, 16.1.

2-Hydroxy-3-oxo-oleana-1,12-dien-N-hydroxy-28-amide (Compound XV)

Prior to the general synthetic scheme described above herein (hydroxamate formation), the acetylation of the hydroxyl group of the C-2 position of a known maslinic acid derivative with CAS num. 1382923-75-2 was carried out as follows:

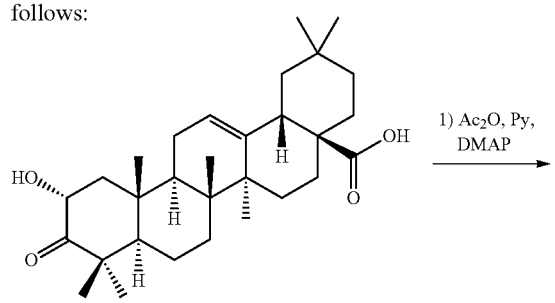

1382923-75-2

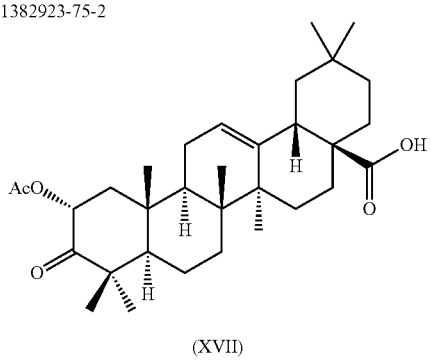

(XVII)

To a solution of the known maslinic acid derivative (1 eq/mol) in dry pyridine (10 mL per gr of acid) were sequentially added acetic anhydride (2 eq/mol) and DMAP (0.1 eq/mol). The reaction is stirred at room temperature until the disappearance of the starting material (control by TLC), quenched with methanol, diluted with H$_2$SO$_4$ sol. 2N and extracted with EtOAc. The organic phases were washed with brine, dried over Na$_2$SO$_4$ and evaporated under vacuum to give compound XVII without further purification.

Compound XVII was then used to carry out the hydroxamate conversion following the general synthetic scheme described above herein as follows:

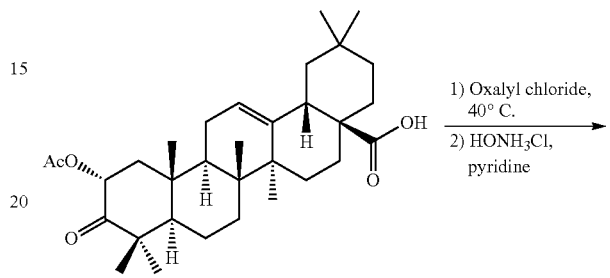

(XVII)

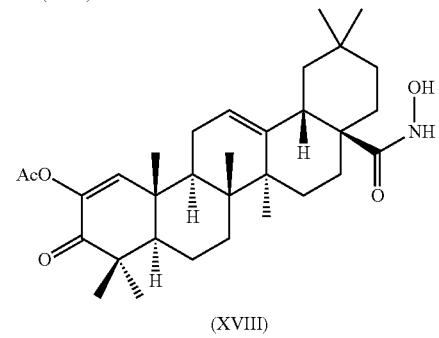

(XVIII)

Compound XVII was then deacetylated to obtain compound XV as follows:

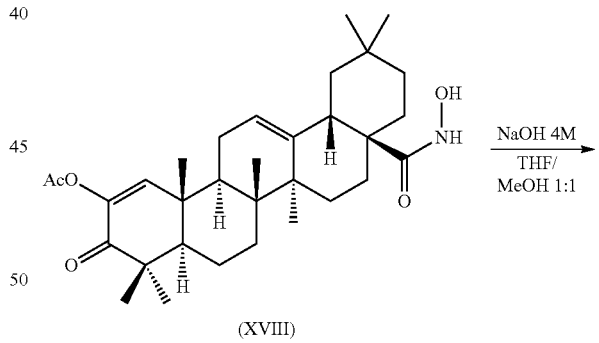

(XVIII)

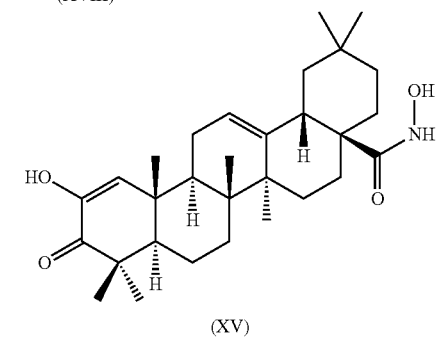

(XV)

To a solution of compound XVII (1 eq/mol) in THF/MeOH 1:1 was added NaOH 4N (50 eq/mol). The mixture was heated at 40° C. overnight, quenched with $H_2SO_4$ sol. 2N and extracted with EtOAc. The organic phases were washed with brine, dried over $Na_2SO_4$ and evaporated under vacuum. The crude compound was purified over silica gel.

Pale yellow solid (69%). $^1$H NMR (300 MHz, CDCl$_3$): d=6.31 (s, 1H), 5.47 (brt, 1H), 2.46 (d, J=11.3 Hz, 1H), 1.20 (s, 3H), 1.19 (s, 3H), 1.13 (s, 3H), 1.10 (s, 3H), 0.88 (s, 3H), 0.86 (s, 6H), (only readily peaks are reported); $^{13}$C NMR (75 MHz, CDCl$_3$) d=201.0, 176.4, 145.2, 143.8, 127.8, 123.2, 53.7, 46.1, 45.5, 44.0, 43.1, 42.4, 40.9, 40.1, 38.4, 33.9, 32.9, 32.0, 30.7, 27.1, 27.0, 25.8, 23.6, 23.4, 21.9, 20.8, 19.6, 18.7, 17.1, 14.2.

As a comparative compound XX was synthesized from glycyrrhetinic acid (GA) by using a T3P/triethylamine protocol without the need of protecting groups (Ech-Chahad et al., Tetrahedron Letters 2005, 46: 5113-5115).

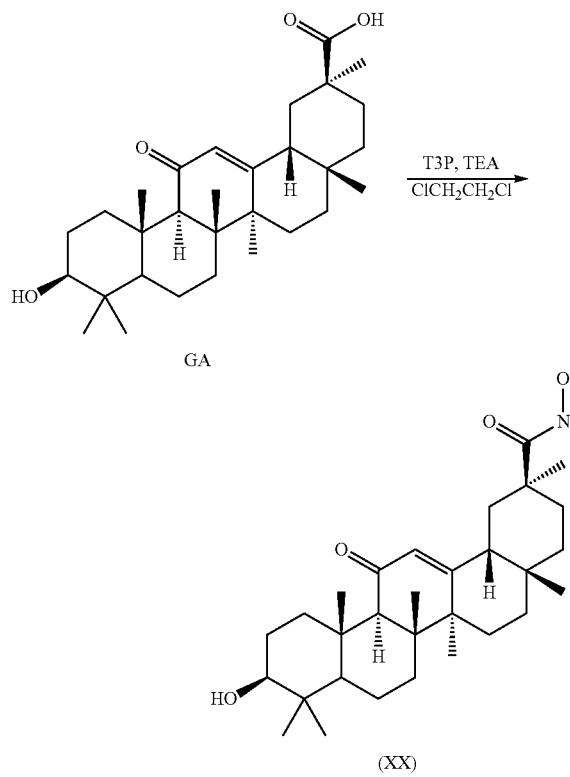

In Silico Assays

Example 2. Calculation of PHD2-Binding Affinity in Silico

Molecular structures were obtained from PubChem (https://pubchem.ncbi.nlm.nih.gov/) or designed with MarvinSketch (ChemAxon, Cambridge, Mass.). The receptor model used was the PDB reference 4BQW. Binding properties were calculated by using the AutoDock4 (Morris et al., J. Comp. Chem. 2009 December; 30(16)2785-91) and the Vina software (Trott and Olson, J. Comp. Chem. 2010 Jan. 30; 31(2):455-61) with the virtual screening tool PyRx (Wolf L K. Chem. & Eng. News 2009, 87) The search space for the docking, around the receptor molecule surface, was set according to previous findings about several binding sites for different PHD2 ligands (Rabinowitz M H, J. Med. Chem. 2013 Dec. 12; 56(23):9369-4025).

Once analysis has been performed, AutoDock Vina provides the estimated binding affinity value, which is the sum of the intermolecular energy, due to the interaction between both molecules, and the torsional free-energy penalty, due to the conformation adopted by these molecules to properly fit the interaction surface. A negative value indicates that bond is thermodynamically stable, whereas a positive value means instability.

Table I shows the PHD2-binding energy (Kcal/mol) for the compounds described in the present invention and also for positive (IOX-2) and negative (glycyrrethinic acid) controls. Mean values from AutoDock-Vina using the structure 4BQW (from Protein Data Bank) are shown. Average values from three independent experiments are shown.

TABLE I

| Energy binding of triterpenoids and derivatives to PDH2. | |
|---|---|
| COMPOUND | B.E. AutoDock (Kcal/mol) |
| Oleanolic acid | −6.35 |
| Compound II | −6.33 |
| Compound III | −3.30 |
| Compound IV | −6.41 |
| Compound V | −3.35 |
| Compound VI | −5.27 |
| Betulinic acid | −4.76 |
| Compound VII | −6.55 |
| Compound VIII | −5.77 |
| Compound IX | −4.33 |
| Compound X | −7.08 |
| Compound XI | −6.09 |
| Ursolic acid | −5.74 |
| Compound XII | −6.01 |
| Compound XIII | −5.45 |
| Maslinic acid | −3.20 |
| Compound XIV | −4.30 |
| Compound XV | −3.57 |
| IOX 2 | −9.05 |
| Glycyrrethinic acid | −1.24 |

PHD2-binding energy (Kcal/mol). Mean values from AutoDock/Vina using the structure 4BQW (from Protein Data Bank) are shown. Average values from three independent experiments are shown.

Search space was restricted to a 300 Å volume around residues H313, D315, H374, R383, Y303, Y310, Y329, I327, I256 and M299, proposed as main binding sites by building a grid surpassing these space in 10 Amstrong along the three axes by (Rabinowitz M H, J. Med. Chem. 2013 Dec. 12; 56(23):9369-4025) (FIG. 1). The resulting binding energy found for Compound VII was −6.55 Kcal/mol, Ki 15.74 uM (at 298.15° K), intermolecular energy −7.38 Kcal/mol and root mean square deviation from atomic position 0.0 Å, thus improving the binding features found for its natural precursor betulinic acid, with a binding energy of −4.76 Kcal/mol.

In Vitro and In Vivo Assays

Example 3. Selective Induction of HIF-1α Activity

Figure 2:
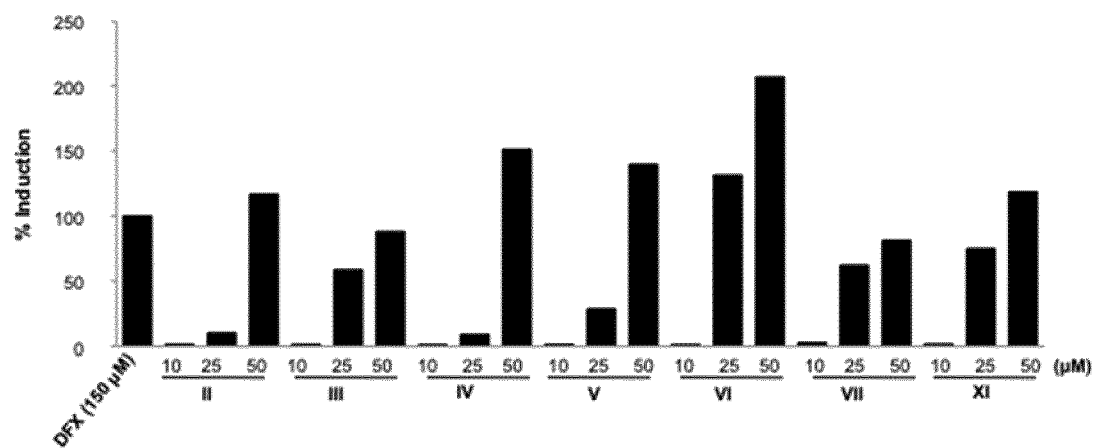
FIG. 2. HIF-1α transactivation assays in HaCaT-EPO Luc keratinocyte cells.
Hypoximimetic effects of DFX and compounds II to XV in HaCaT-EPO-Luc cells. The concentration of the tested compound (μM) is shown at the x-axis and the percentage of HIF-1α activation is shown at the y-axis. This figure shows the effect of DFX versus compounds (FIG. 2A) II, III, IV, V, VI, VII, XI, (FIG. 2B) VIII, IX, X, XII, XIII, XIV and XV on EPO-luc activity considering the induction mediated by DFX (150 μM) as 100% activation over untreated cells.
Figure 2:
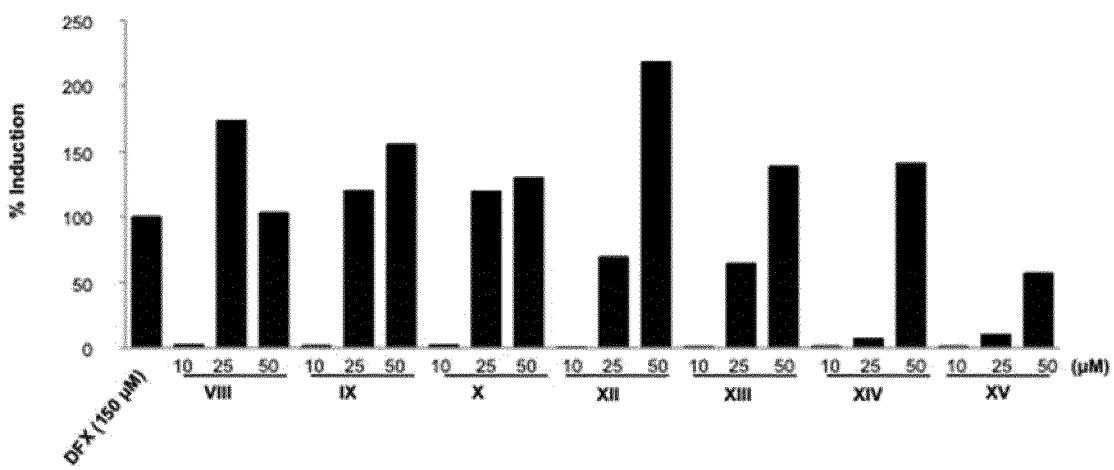

To investigate the biological activities of the different compounds, HIF-1α transactivation assays were performed either in NIH-3T3-EPO-Luc cells (Table II) or in HaCaT-EPO-luc cells (FIG. 2). The NIH3T3-EPO-luc and HaCaT-EPO-luc cells have been stably transfected with the plasmid Epo-Luc plasmid. The EPO-Hypoxia Response Element (HRE)-luciferase reporter plasmid contains three copies of the HRE consensus sequence from the promoter of the erythropoietin gene fused to the luciferase gene. NIH3T3-EPO-luc cells were maintained at 37° C. in a humidified atmosphere containing 5% $CO_2$ in DMEM supplemented with 10% fetal calf serum (FBS), and 1% (v/v) penicillin/streptomycin. DFX was purchased from Sigma-Aldrich (USA). Cells (1×10$^4$/well in 96 well plates) were seeded the day before the assay. The next day, the cells were stimulated either with increasing concentrations of either Oleanolic acid (OA), Betulinic acid (BA), Ursolic acid (UA), Maslinic acid (MA) Glycyrrethinic acid (GA), compounds of Formula (I), II to XV, or comparative compounds XX and CDDO-Me. After six hours of stimulation the cells were lysed in 25 mM Tris-phosphate pH 7.8, 8 mM MgCl$_2$, 1 mM DTT, 1% Triton X-100, and 7% glycerol during 15 min at RT in a horizontal shaker. Luciferase activity is measured using a microplate luminometer (Berthold) following the instructions of the luciferase assay kit (Promega, Madison, Wis., USA). The RLUs are calculated and the EC50 and IRA (Intrinsic relative activity) values were determined relative to 150 μM deferoxamine (DFX) using the following equation: IRA coefficient=(EC$_{50\text{-}DFX}$×E$_{max}$)/(EC$_{50}$×E$_{max\text{-}DFX}$), where EC$_{50}$ and E$_{max}$ denote EC$_{50}$ and E$_{max}$ of the agonist, and EC$_{50\text{-}DFX}$ and E$_{max\text{-}DFX}$ denote EC$_{50}$ and E$_{max}$ values of the standard agonist DFX (Table II).

None of the natural triterpenoids (OA; Olanolic acid, BA; Betulinic acid; UA, Ursolic acid, and MA; Maslimic acid) used as templates for the synthesis of the compounds included in the present invention were able to activate the EPO promoter as a surrogate marker of HIF-1α activation. In contrast all the triterpenoid derivatives of present invention clearly activated the HIF-1α pathway (Table II). Moreover, as shown in Table II below, compounds II to VI which are oleanolic acid derivatives of Formula I provide activation of the HIF pathway, while in contrast, an oleanolic derivative such as CDDO-Me, comprising a cyanide group at position 2 (corresponding to position B of Formula I) does not result in activation of the HIF pathway.

Thus, it can be concluded that the chemical modifications introduced in the compounds described are critical to inhibit the enzymatic activity of PHD2, and as a consequence, to activate the HIF pathway, but not for the binding of the compounds to the protein.

Table II also shows that GA and its hydroxamate derivative compound XX, do not activate the HIF-1α pathway. Thus, particularly, it can be concluded that the chemical modifications introduced at the position 28 of the backbone defined in the present invention is critical to inhibit the enzymatic activity of PHD2, and as a consequence, to activate the HIF pathway, but not for the binding of the compounds to the protein.

TABLE II

HIF-1α transactivation assays in NIH-3T3-EPO Luc fibroblast cells.

| Compound | Efficacy HIF-1α (IRA coefficient) | Potency EC$_{50}$ HIF-1α (μM) |
|---|---|---|
| OA | — | (>50) |
| II | 0.39 | 16.37 |
| III | 0.43 | 3.83 |
| IV | 0.15 | 11.39 |
| V | 0.16 | 6.71 |
| VI | 0.16 | 5.00 |
| BA | — | (>50) |
| VII | 0.36 | 4.81 |
| VIII | 0.55 | 2.58 |
| IX | 0.34 | 2.41 |
| X | 0.48 | 3.24 |
| XI | 0.31 | 2.58 |
| UA | — | (>50) |
| XII | 0.17 | 7.69 |
| XIII | 0.10 | 8.93 |

TABLE II-continued

HIF-1α transactivation assays in NIH-3T3-EPO Luc fibroblast cells.

| Compound | Efficacy HIF-1α (IRA coefficient) | Potency EC$_{50}$ HIF-1α (μM) |
|---|---|---|
| MA | — | (>50) |
| XIV | 0.10 | 7.10 |
| XV | 0.06 | 11.22 |
| GA | — | (>50) |
| XX | — | (>50) |
| CDDO—Me | — | (>50) |

NIH3T3-EPO-luc cell line stably transfected with the Epo-Luc plasmid, which contains three copies of the Hypoxia Response Element consensus sequence from the promoter of the erythropoietin gene fused to luciferase gene. The efficacy and potency for HIF-1α activation is shown.

Next, the activity of the compound in another cell type such as the keratinocyte cell line HaCaT-EPO-Luc was studied. The cells were maintained at 37° C. in a humidified atmosphere containing 5% CO$_2$ in DMEM supplemented with 10% fetal calf serum (FBS), and 1% (v/v) penicillin/streptomycin. The cells (1×10$^5$/well in 24 well plates) were seeded the day before the assay and then stimulated with either DFX (150 μM) or with increasing concentrations of compounds II to XV for 6 h. Then, the cells were lysed in 25 mM Tris-phosphate pH 7.8, 8 mM MgCl$_2$, 1 mM DTT, 1% Triton X-100, and 7% glycerol. Luciferase activity was measured in the cell lysate using a TriStar LB 941 multi-mode microplate reader (Berthold) following the instructions of the Luciferase Assay Kit (Promega, Madison, Wis., USA). The above assay is illustrated by FIG. 2, which shows the hypoximimetic effects of DFX and compounds II to XV in HaCaT-EPO-Luc cells. Data are given as percentage of activation considering DFX (150 μM) as 100% induction over untreated cells. A significant increase in luciferase activity was seen with all triterpenoid derivatives as compared with untreated cells.

To further study the target selectivity of the compounds described in the present invention the effect of the natural triterpenoids (OA; BA, UA, and MA), compounds II to XV of Formula (I) disclosed in present invention, and of comparative compound CDDO-Me on NF-κB inhibition, STAT-3 inhibition, Nrf2 activation and TGR5 activation was analyzed. For this study cell lines NIH-3T3-KBF-Luc, HeLa-STAT3-Luc, HaCaT-ARE-Luc and CHO-TGR5-CRE-luc were used respectively. The NIH3T3-KBF-Luc cell line stably transfected with the plasmid KBF-Luc plasmid, which contains three copies of NF-κB binding site (from major histocompatibility complex promoter), fused to a minimal simian virus 40 promoter driving the luciferase gene. Cells (1×10$^4$/well) were seeded in 96-well plates, treated with increasing concentrations of the compounds II to XV for 15 min and then stimulated with 30 ng/ml TNFα. After 6 h the luciferase activity in the cell lysates was measured as indicated above. The RLU is calculated and the results are expressed as percentage of inhibition of NF-κB activity induced by TNFα (100% activation) (Table III).

TABLE III

Effects on NF-κB, STAT-3, Nrf2 and TGR5 pathways.

| Compound | IC$_{50}$ NF-κB (μM) | IC$_{50}$ STAT3 (μM) | EC$_{50}$ NRF2 (μM) | IC$_{50}$ NRF2 (μM) | EC$_{50}$ TGR5 (μM) |
|---|---|---|---|---|---|
| OA | — (>50) | — (>50) | — (>50) | — (>50) | 18.90 |
| II | — (>50) | — (>50) | — (>50) | — (>50) | — (>50) |
| III | — (>50) | — (>50) | 23.93 | — (>50) | — (>50) |

TABLE III-continued

Effects on NF-κB, STAT-3, Nrf2 and TGR5 pathways.

| Compound | IC$_{50}$ NF-κB (μM) | IC$_{50}$ STAT3 (μM) | EC$_{50}$ NRF2 (μM) | IC$_{50}$ NRF2 (μM) | EC$_{50}$ TGR5 (μM) |
|---|---|---|---|---|---|
| IV | — (>50) | — (>50) | 10.04 | — (>50) | — (>50) |
| V | — (>50) | — (>50) | — (>50) | — (>50) | — (>50) |
| VI | — (>50) | — (>50) | — (>50) | — (>50) | — (>50) |
| BA | — (>50) | — (>50) | 9.02 | — (>50) | 22.15 |
| VII | — (>50) | — (>50) | — (>50) | — (>50) | — (>50) |
| VIII | — (>50) | — (>50) | — (>50) | — (>50) | 9.62 |
| XI | — (>50) | — (>50) | — (>50) | — (>50) | 17.50 |
| X | — (>50) | — (>50) | — (>50) | — (>50) | — (>50) |
| XI | — (>50) | — (>50) | — (>50) | — (>50) | 17.50 |
| UA | — (>50) | — (>50) | 38.36 | — (>50) | 11.46 |
| XII | — (>50) | — (>50) | — (>50) | — (>50) | 5.91 |
| XIII | — (>50) | — (>50) | — (>50) | — (>50) | — (>50) |
| MA | — (>50) | — (>50) | — (>50) | — (>50) | 10.19 |
| XIV | — (>50) | — (>50) | — (>50) | — (>50) | — (>50) |
| XV | (>50) | (>50) | (>50) | (>50) | (>50) |
| CDDO—Me | 1.20 | 2.38 | 40.94 | 0.06 | (>50) |

Effect of compounds II to XV, OA; BA, UA, MA and of comparative compound CDDO—Me, on NF-κB inhibition (IC50), STAT-3 inhibition (IC50), Nrf2 activation (EC50) and inhibition (IC50) and TGR5 activation (EC50) we used the cell lines NIH-3T3-KBF-Luc, HeLa-STAT3-Luc, HaCaT-ARE-Luc and CHO-TGR5-CRE-luc respectively. The IC50 and EC50 data are shown.

The HeLa-STAT3-luc cells stably transfected with the plasmid 4×M67 pTATA TK-Luc. Cells ($20 \times 10^3$ cells/ml) were seeded in 96-well plates, treated with increasing concentrations of the compounds II to XIV, and of comparative compound CDDO-Me, for 15 min and then stimulated with IFN-γ 25 IU/ml. After 6 h the luciferase activity in the cell lysates was measured as indicated above. The RLU was calculated and the results expressed as percentage of inhibition of STAT3 activity induced by IFN-γ (100% activation) (Table III). The HaCaT-ARE-Luc cell line contains the Nqo1 Antioxidant Response Element (ARE)-Luc reporter plasmid. ARE is activated by all members of the CNC family of factors (Nrf1, Nrf2, Nrf3 and p45 NF-E2). The cells were cultivated in 96-well plates at the concentration of $25 \times 10^3$ cells/well in a $CO_2$ incubator at 37° C. For induction of Nrf2 activation the cells were treated with increasing concentrations of the compounds II to XV, and of comparative compound CDDO-Me, for 6 h. As a positive control the cells were treated with 0.02 mM of the antioxidant Tert-butyl-hydroquinone (TBHQ). Luciferase activity in the cell lysates was measured as indicated above and the EC50 calculated (Table III). The CHO-TGR5-CRE-Luc cells stably transfected with the pTGR5 and CRE-Luc. The CRE-responsive luciferase construct encodes the firefly luciferase reporter gene under the control of a minimal (m)CMV promoter and tandem repeats of the CRE transcriptional response element (TRE) and is useful to monitor cAMP signaling pathways activated by TGR5 agonists. Cells ($1 \times 10^4$/well) were seeded in 96-well plates, treated with increasing concentrations of the compounds II to XV and CDDO-Me, for 6 h. As a positive control the cells were treated with 10 μM of LCA (lithocholic acid). Luciferase activity in the cell lysates was measured as indicated above and the EC50 calculated (Table III).

None of the compounds inhibited the NF-κB and STAT3 pathways induced by TNFα and IFNγ respectively. In addition, none of the compounds activated the Nrf2 pathway and only compounds VIII, XI and XII showed agonistic TGR5 activity (Table III). In contrast, CDDO-Me clearly inhibited NF-κB and STAT-3 signaling pathways and activated the Nrf2 pathway. This result further demonstrated that the cyanide group is critical for some biological activities but is not required to activate the HIF-1α pathway (Table III).

Example 4. Triterpenoid Derivatives Stabilize HIF-1α and HIF-2α

Figure 3:
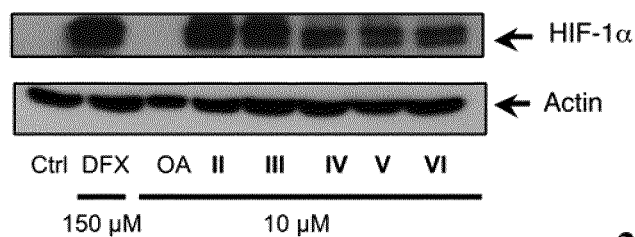
FIG. 3. HIF-1α stabilization in oligodendrocytes.
Stimulation of human oligodendrocyte MO13.3 cells for 3 hours with either 150 μDFX or 10 μM of Olenaolic acid (OA), compounds II, III, IV, V, VI (FIG. 3A), betulinic acid (BA), compounds VII, VIII, IX, X, XI (FIG. 3B), ursolic acid (UA), maslinic acid (MA), compounds XII, XIII, XIV and XV (FIG. 3C) to determine the expression of HIF-1α and β-actin by Western blots.
Figure 3:
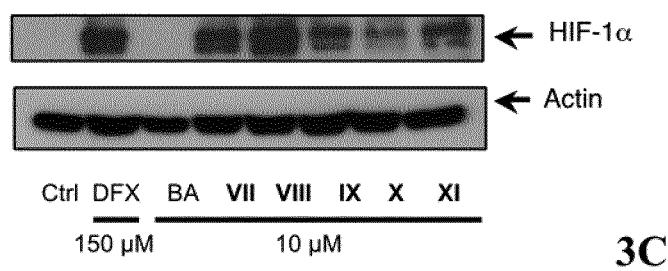
Figure 3:
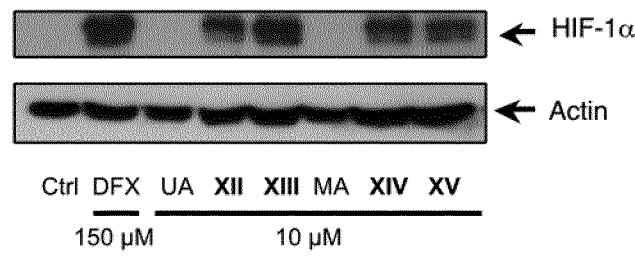

To gain insight into the regulation of HIF-1α stabilization by the compounds described in the present invention the effect on HIF-1α expression in different cell types was investigated. Human oligodendrocyte MO13.3 cells were stimulated for 3 h with either 150 μDFX or 10 μM of Olenaolic acid (OA), compounds II, III, IV, V, VI (FIG. 3A), betulinic acid (BA), compounds VII, VIII, IX, X, XI (FIG. 3B), ursolic acid (UA), maslinic acid (MA), compounds XII, XIII, XIV and XV (FIG. 3C). After that, the cells were washed with PBS and incubated in 50 μl of NP-40 buffer (50 mM Tris-HCl pH 7.5, 150 mM NaCl, 10% glycerol and 1% NP-40) supplemented with 10 mM NaF, 1 mM $Na_3VO_4$, 10 μg/ml leupeptine, 1 μg/ml pepstatin and aprotinin, and 1 μl/ml PMSF saturated. After centrifugation the supernatants were mixed with SDS sample buffer and boiled at 95° C. Proteins were electrophoresed in 8-10% sodium dodecyl sulfate polyacrylamide gel (SDS-PAGE) and transferred to polyvinylidene difluoride membranes (20 V and 30 min per membrane). After blocking with non-fat milk or BSA in TBST buffer, primary antibodies were added. The washed membranes were incubated with appropriate secondary antibodies coupled to horseradish peroxidase that were detected by an enhanced chemiluminescence system (USB). The antibody against HIF-1α (610959) was from BD Biosciences and the antibody anti-β-actin (AC-74) was purchased from Sigma-Aldrich (Saint Louis, Mo., USA).

All the compounds described in the present invention elevated HIF-1α protein level under normoxia conditions (21% $O_2$). The extent of induction was comparable to that of desferrioxamine (DFX), an iron chelator known to stabilize HIF-1α (FIGS. 3A, 3B and 3C).

Next, Human Embryonic Kidney 293 cells (293T) were stimulated with the increasing concentrations of compound VII or with DFX (150 μM) during 3 h. After that, proteins isolation and western blots were performed as in FIG. 3. The antibody against HIF-1α (610959) was from BD Biosciences (USA), the antibodies anti-PHD1 (ab80361) and anti-PHD2 (ab109088) were from Abcam (Cambrigde, UK), and the antibody anti-β-actin (AC-74) was purchased from Sigma-Aldrich (Saint Louis, Mo., USA).

Figure 4:
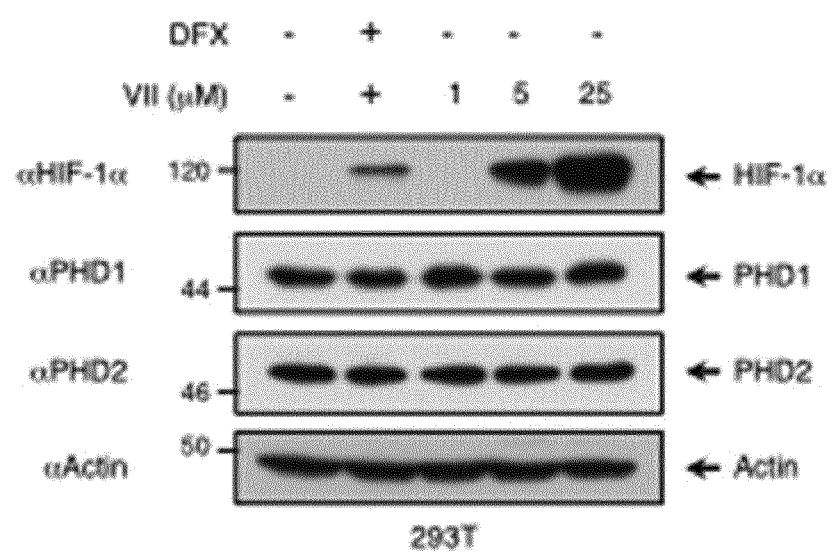
FIG. 4. HIF-1α stabilization in 293T cells.
Stimulation of human Embryonic Kidney 293 cells with increasing concentrations of compound VII or with DFX (150 μM) during 3 h. The steady state levels of the proteins HIF-1α, PHD1, PHD2 and β-actin were determined by Western blots.

The results clearly show that compound VII, as a representative of the compounds described in the present invention stabilized HIF-1α expression without affecting the expression of PDH1 and PDH2 (FIG. 4).

Since PDH2 and PDH3 also regulate the expression of HIF-2α, the effect of compound VII on HIF-2α stabilization in Human Islet-Derived Precursor Cells (hIPCs) obtained from Innoprot SL (Spain) (reference p10472) was investigated. hIPCs were stimulated with the increasing concentrations of compound VII or with DFX (150 μM) during 3 h. After that, proteins isolation and western blots were performed as in FIG. 3. The antibodies against HIF-2α (ab8365) and PHD3 (ab30782) were from Abcam (Cambrigde, UK), and the antibody anti-β-actin (AC-74) was purchased from Sigma-Aldrich (Saint Louis, Mo., USA). (FIG. 5).

Figure 5:
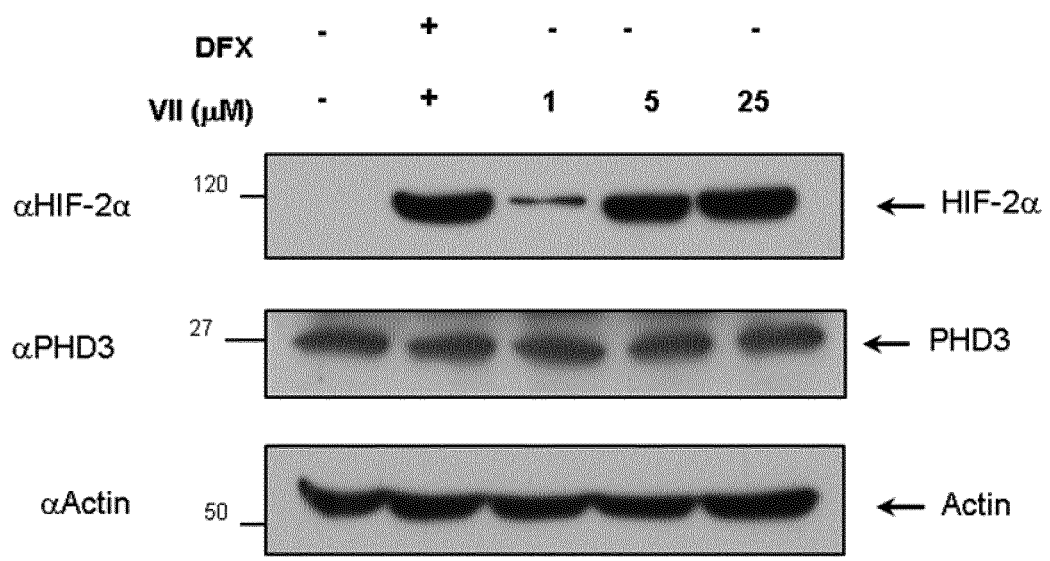
FIG. 5. HIF-2α stabilization in hIPCs.
Stimulation of human Islet-Derived Precursor Cells (hIPCs) with increasing concentrations of compound VII or with DFX (150 μM) during 3 h, and the expression of HIF-2α, PHD3 and β-actin determined by Western blots.

The results clearly show that compound VII, as a representative of the compounds described in the present invention stabilized HIF-2α expression without affecting the expression of PHD3 (FIG. 5).

Altogether, results indicate that compound VII binds PDH2 inhibiting its activity and as consequence HIF-1α and HIF-2α protein levels are stabilized.

Example 5. Compound VII Induces Angiogenesis

To test the functional consequences of compound VII stimulation in a physiological model, endothelial cell tube formation was measured as a model of angiogenesis. CellPlayer™ GFP AngioKit-96 (Essen BioScience Inc., Welwyn Garden City, UK) was supplied as growing co-cultures of human matrix (normal human dermal fibroblast, NHDF) and endothelial cells (HUVEC) at the earliest stages of tubule formation. CellPlayer 96-well kinetic angiogenesis assay was performed according to the manufacturer's protocol. Briefly, lentivirally infected green fluorescent protein (GFP)-HUVECs were cocultured with normal human dermal fibroblasts in a 96-well microplate. The plate was placed in IncuCyte, and images were automatically acquired in both phase and fluorescence every 6 hours for 7 days. At day 1, compound VII (1 and 2.5 µM) or VEGF (10 ng/ml) were added on the endothelial tube networks and kept throughout the experiment. Tube formation over the 7-day assay was quantified using the Essen BioScience Angiogenesis Analysis Module. This module provides multiple assay metrics, including tube length and branch point formation, which are used to assess angiogenic effects on network formation. Briefly, the fluorescent images were analyzed to generate a segmentation mask closely resembling the in vitro network. The mask was then refined to specifically identify tube-forming events, and the kinetic response was plotted using the IncuCyte and GraphPad Prism software (La Jolla, Calif.).

Figure 6:
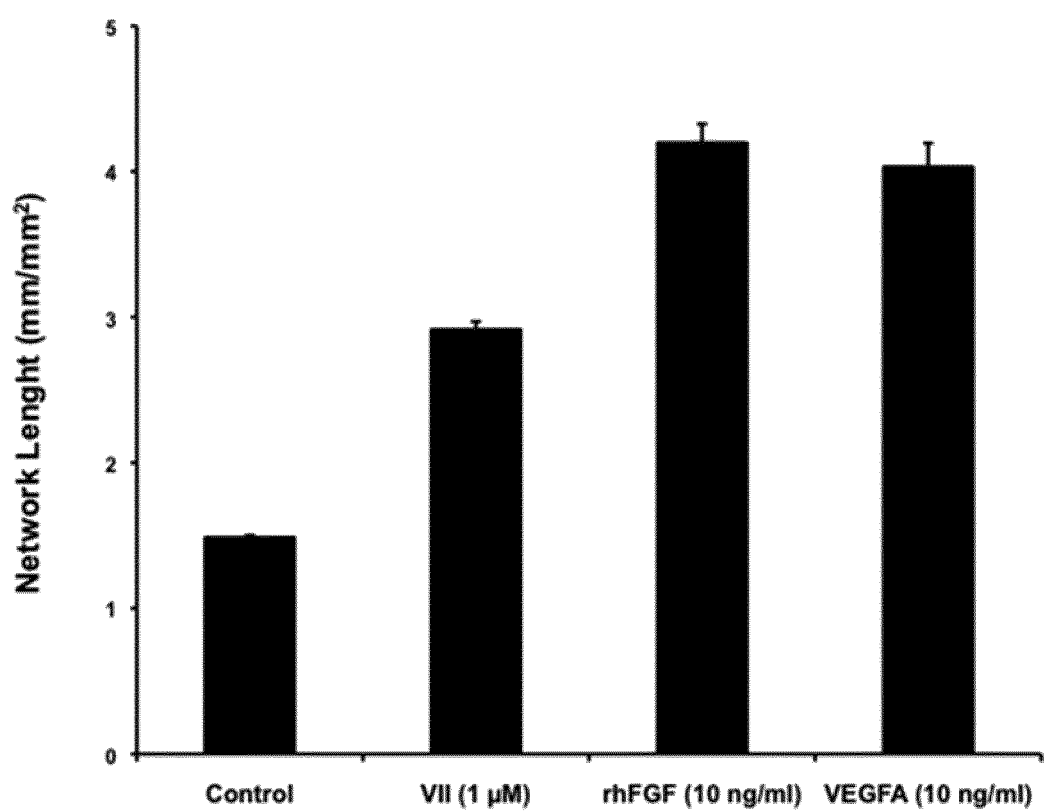
FIG. 6. Compound VII induces angiogenesis.
Measurements of endothelial cell tube formation as a model of angiogenesis in green fluorescent Human endothelial vascular cells (HUVEC) co-cultured with primary fibroblasts and stimulated separately with compound VII (1 μM), rhFGF (10 ng/ml) and VEGFA (10 ng/ml) for 7 days. Values represent the mean±SEM (n=3).

In FIG. 6 it is shown that compound VII 1 µM as well as the positive controls (rFGF; 10 ng/ml and VEGFA; 10 ng/ml) increased significantly the network length in HUVEC cells.

Example 6. Compound VII Increase the Plasma Levels of Erythropoietin (EPO)

Erythropoietin (EPO) is one of the earliest described and most sensitive HIF target genes; being positively regulated at the transcription level. Here, the ability of compound VII to regulated EPO levels in vivo was examined. Sixteen-week-old C57BL/6 male mice were treated intraperitoneally (i.p.) with Betulinic Acid (60 mg/kg) or compound VII (30 mg/kg or 60 mg/kg). Blood samples were taken under general anaesthesia 4 hours after treatment and the circulating levels of EPO in plasma were quantified using a mouse EPO ELISA kit (R&D Systems) according to manufacturer's instructions. EPO values represent the mean±SEM (n=3).

Figure 7:
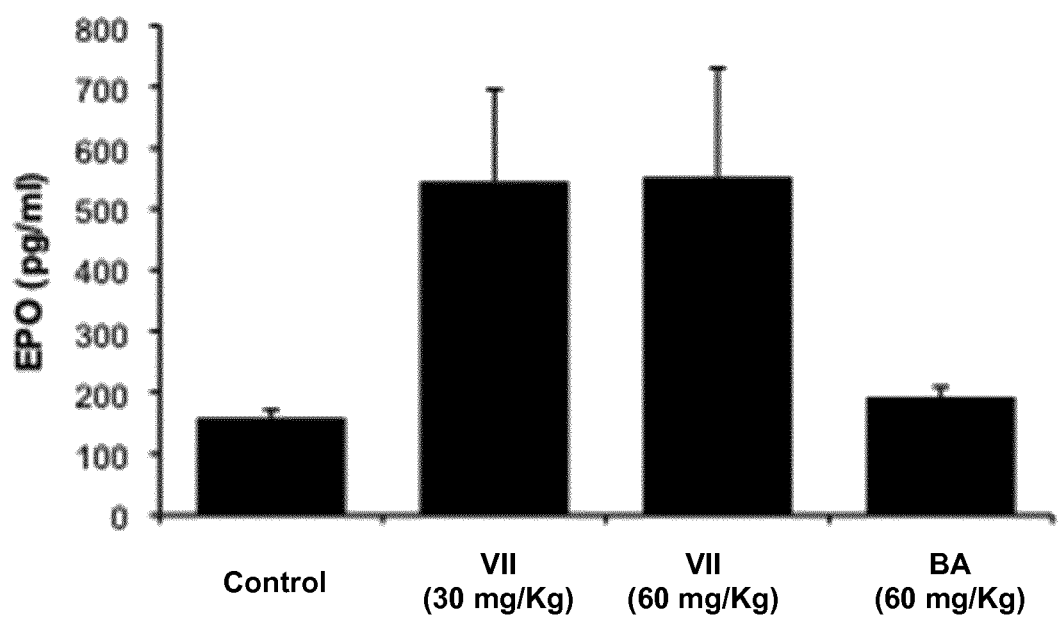
FIG. 7. Influence of compound VII on erythropoietin (EPO) in vivo.
EPO in plasma measured using a mouse EPO ELISA kit in C57BL/6 male mice administered with compound VII (30 mg/kg or 60 mg/kg) or betulinic acid (BA) (60 mg/kg) intraperitoneally. Control group did not receive any treatment. Data are expressed as mean±SEM (n=3).

As shown in FIG. 7 in vivo administration of compound VII, as a representative of the compounds described in the present invention, in mice (30 and 60 mg/kg/day) strongly increased circulating EPO plasma levels. In contrast Betulinic acid (BA), the parental of compound VII, did not influence the levels of EPO in plasma.

Example 7. Effect of Compound VII on 3-NP-Induced Cytotoxicity in Striatal Cells, and Prevention of 3-NP Induced Huntington's Disease in Mice 7.1: Effect of Compound VII on 3-NP-Induced Cytotoxicity in Striatal Cells To investigate whether HIF activation in striatal Q7 and Q111 cells is sufficient to protect striatal neurons (provide neuroprotection), the effect of compound VII on 3-NP induced death was examined. In particular, the effect of 6 h pre-treatment with compound VII on 24 h of 3-Nitropropionic acid (3-NP) exposure in STHdh$^{Q7/Q7}$ (striatal Q7) and STHdh$^{Q111/Q111}$ (striatal Q111) cells was studied.

STHdh$^{Q111/Q111}$ cells express a mutated form of the huntingtin protein and STHdh$^{Q7/Q7}$ cells express the wild type form of this protein. Clonal striatal cell lines established from E14 striatal primordia of Hdh$^{Q111/Q111}$ (mutant) and Hdh$^{Q7/Q7}$ (wild-type) knock-in mouse littermates were immortalized using a replication defective retrovirus transducing the tsA58/U19 large T-antigen (Trettel F. et al., Hum Mol Genet. 2000; 9:2799-2809). Striatal Q7 and Q111 cells were maintained in Dulbecco's modified Eagle medium (DMEM) containing 25 mM D-glucose, 1 mM L-glutamine, 10% fetal bovine serum (FBS), 1 mM sodium pyruvate, and 400 µg/mL Geneticin and were incubated at 33° C. with 5% $CO_2$.

3-Nitropropionic acid (3-NP) is a potent irreversible inhibitor of mitochondrial complex II enzyme and leads to mitochondrial dysfunction and oxidative stress.

STHdh$^{Q7/Q7}$ and STHdh$^{Q111/Q111}$ cells ($10^4$ cells/well in 96-well plates) were incubated with YOYO-1 (Life Technologies) and then treated with 3-NP (10 mM) and or DFX (50 µM) as a positive control for PHDs inhibition. YOYO-1 is diluted in cell culture medium and added to a final concentration of 0.1 µM to both experimental and control wells. YOYO-1 is a cell impermeant cyanine dimer nucleic acid stain that can only enter cells with a compromised plasma membrane and fluorescently stain the nuclear DNA. The uptake of YOYO-1 by damaged cells correlates with the increase in YOYO-1 fluorescence. Treated cells are placed in an Incucyte FLR imaging system, and the YOYO-1 fluorescence is measured after 24 h of 3-NP treatment. Following the incubation period object counting analysis was performed using the Incucyte FLR software to calculate the total number of YOYO-1 fluorescence positive cells and total DNA containing objects (end point). The cytotoxicity index is calculated by dividing the number of YOYO-1 fluorescence positive objects by the total number of DNA containing objects for each treatment group and converted to percentage of cell death.

Figure 8:
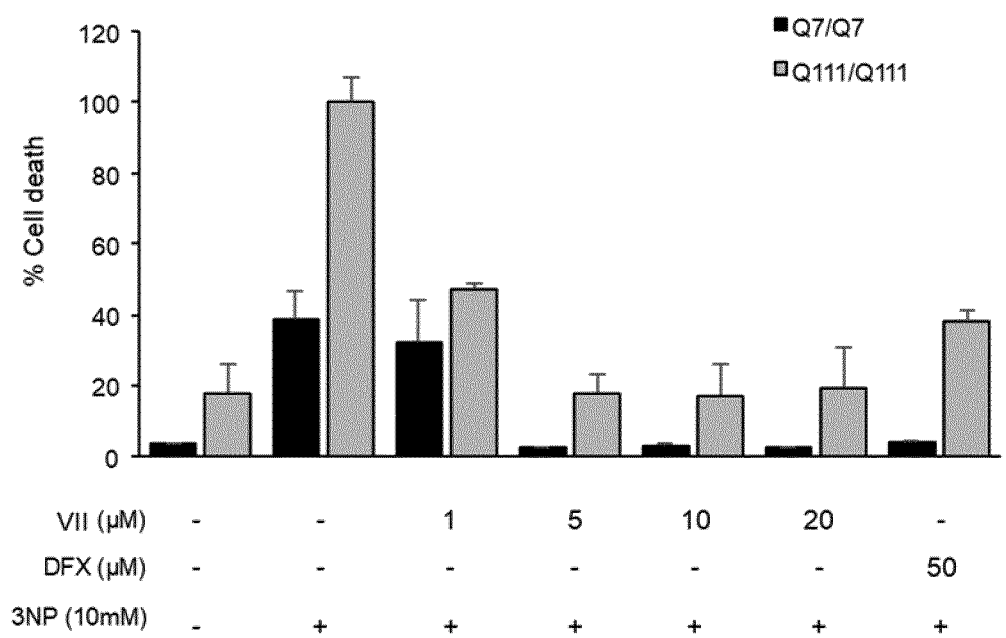
FIG. 8. Compound VII abrogates 3-NP toxicity in Q7 and Q111 striatal cells. Q7 and Q111 Striatal cells were pretreated with increasing concentrations of compound VII for 6 h and then exposed to 3-NP (10 mM) for an additional 24 h, after which YOYO-1 staining was used to investigate cell death. Cell death was determined using the IncuCyte HD software and the treatment with 3-NP alone in Q111 cells was considered as 100% of cell death.

STHdh$^{Q111/Q111}$ cells were more sensitive than STHdh$^{Q7/Q7}$ cells to the exposure to 3-NP and compound VII clearly provided a significant level of neuroprotection to 3-NP-induced cytotoxicity (FIG. 8). Although to a lesser extent, DFX also protected the cells from the cytotoxic activity of 3-NP.

7.2: Prevention of 3-NP Induced Huntington's Disease in Mice

The intoxication of mice with 3-Nitropropionic acid (3-NP), results in a myriad of neurological, biochemical and histological effects that are reminiscent of some aspects of Huntington disease (HD) pathology. 3NP-treated mice exhibited high scores in hindlimb clasping, dystonia, kyphosis and in general locomotor activity compared to control animals (non-intoxicated with 3-NP).

Striatal neurodegeneration was induced in 16-week-old C57BL/6 male mice (Harlan Ibérica, Barcelona, Spain) by six intraperitoneal (i.p.) injections of 3-nitropropionic acid (3NP) (30 mg/kg; one injection each every 12 h prepared in PBS). 3NP-treated animals and the non-lesioned control group (injected with PBS) were used for pharmacological studies with Betulinic acid (30 mg/Kg) and compound VII (30 mg/Kg). Treatments consisted of 5 i.p. injections every 24 h with 50 mg/kg the test compounds or vehicle (10% DMSO plus 6.2% Tween 20 in saline buffer), with the first injection 24 h prior the first 3NP injection and the rest of doses 30 min before the injections of 3NP. Mice were subjected to behavioral tests for determining their neurological status. General locomotor activity, the hindlimb clasping and dystonia, and the truncal dystonia were evaluated. All behavioral tests were conducted prior to drug injections to avoid acute effects of the compounds under investigation. All behavioral tests were conducted prior to drug injections to avoid acute effects of the compounds under investigation and all animals were euthanized 12 h after the last injection of 3NP. Once euthanized, animals were dissected and their brains were rapidly removed. The right hemisphere was used to dissect the striatum, which was quickly frozen in RNAlater (Sigma-Aldrich, Germany) to analyzed inflammatory markers were by Real Time PCR. The left hemisphere was fixed in fresh 4% paraformaldehyde (in 0.1M phosphate buffered-saline) for 48 hours at 4° C. and embedded in paraffin wax for histological analysis.

Figure 9:
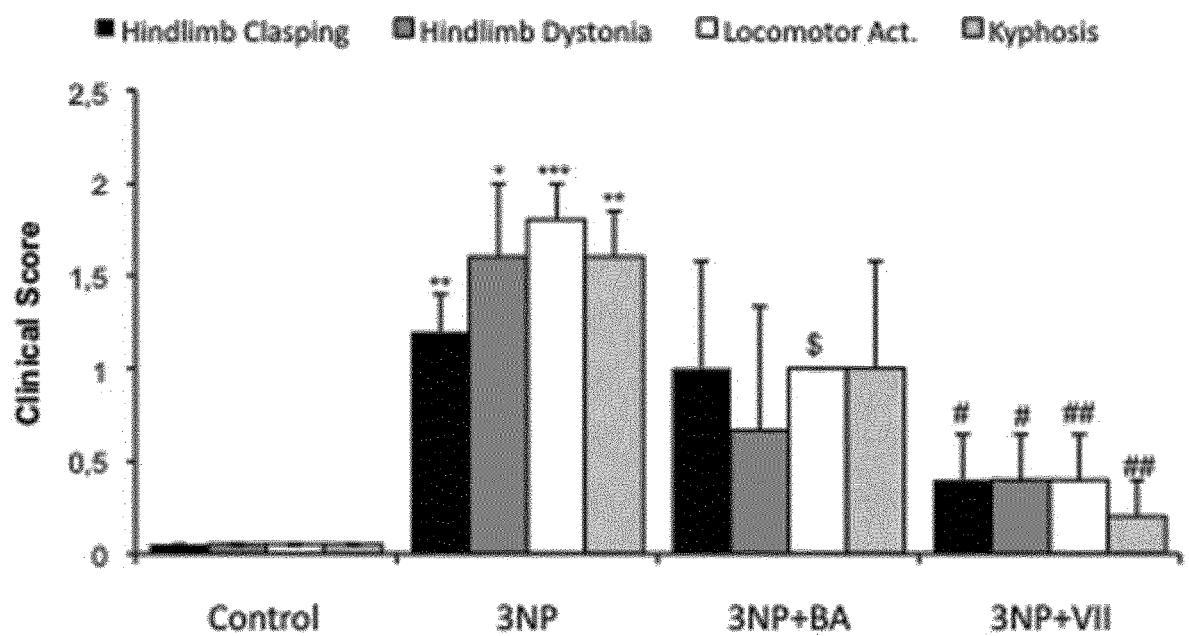
FIG. 9. Behavioral score after 3NP intoxication.
Intoxicated mice with 3-Nitropropionic acid (3-NP) were subjected to behavioral tests for determining their neurological status after the treatment with compound VII (30 mg/kg) and Betulinic acid (BA) (30 mg/kg) versus a control of non-intoxicated mice. Hind limb clasping, Locomotor activity, Hind limb dystonia and Truncal Dystonia were rated from 0 to 2 based on severity: a score of 0 typically indicates normal function and 2 seriously affected. Values are expressed as means±SEM for 6 animals per group.

FIG. 9 shows that compound VII clearly alleviated the clinical symptoms induced by 3-NP intoxication. Betulinic acid (BA) also showed some neuroprotective activity although to a lesser extent.

Figure 10:
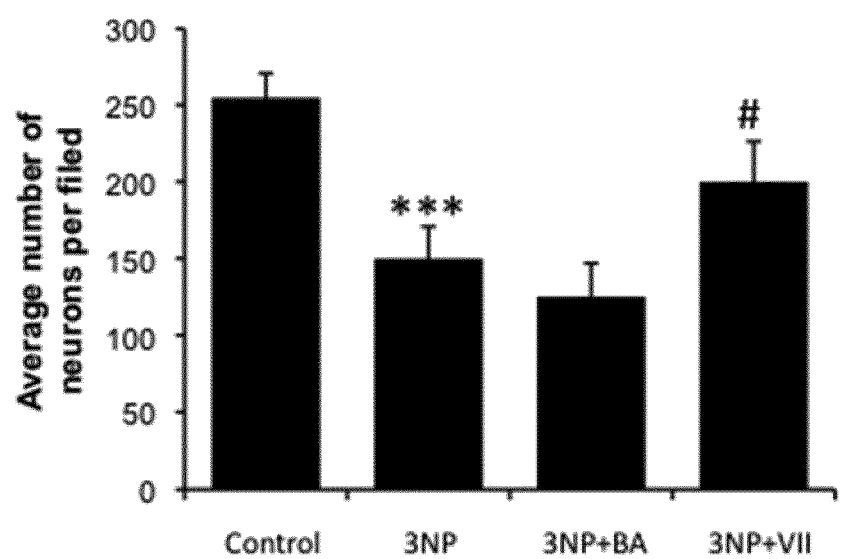
FIG. 10. Effect of compound VII on neuronal loss.
Intoxicated mice with 3-Nitropropionic acid (3-NP) for determining degeneration in the striatum including Control (non-intoxicated mice), 3NP, 3NP+BA and 3NP+Compound VII). Quantification of Nissl-positive cells in the mouse striatum. Total average number of neurons (100× magnification) is shown. Values are expressed as means±SEM for 6 animals per group. Data were subjected to one-way analysis of variance followed by the Student-Newman-Keuls test. ***P<0.001 when comparing the control group with the 3NP and control group. #P<0.05 when comparing the 3NP group with the 3NP+compound VII group FIG. 11. Effect of compound VII on microgliosis (Iba1$^+$) and astrogliosis (GFAP$^+$) induced by 3NP
Intoxicated mice with 3-Nitropropionic acid (3-NP) for determining microglia activation and astrogliosis including Control (non-intoxicated mice), 3NP, 3NP+BA and 3NP+Compound VII). Iba-1 and glial fibrillary acidic protein (GFAP) expression were determined by immunostaining of brain sections through the different group of mice and quantification of the different markers was performed with Image J software. Total average number of microglia (Iba1$^+$) and astrocytes (GFAP$^+$) is shown.

Next, striatal parenchyma of 3NP-lesioned mice was also used for analysis of some histological and molecular markers related to inflammation and neurodegeneration, which are affected in this experimental model. The striatal parenchyma of these 3NP-treated animals showed an important reduction in Nissl-stained cells, which indicates an important degree of neuronal death caused by 3NP, that was clearly prevented by treatment with compound VII but not by Betulinic acid (BA) (FIG. 10).

Figure 11:
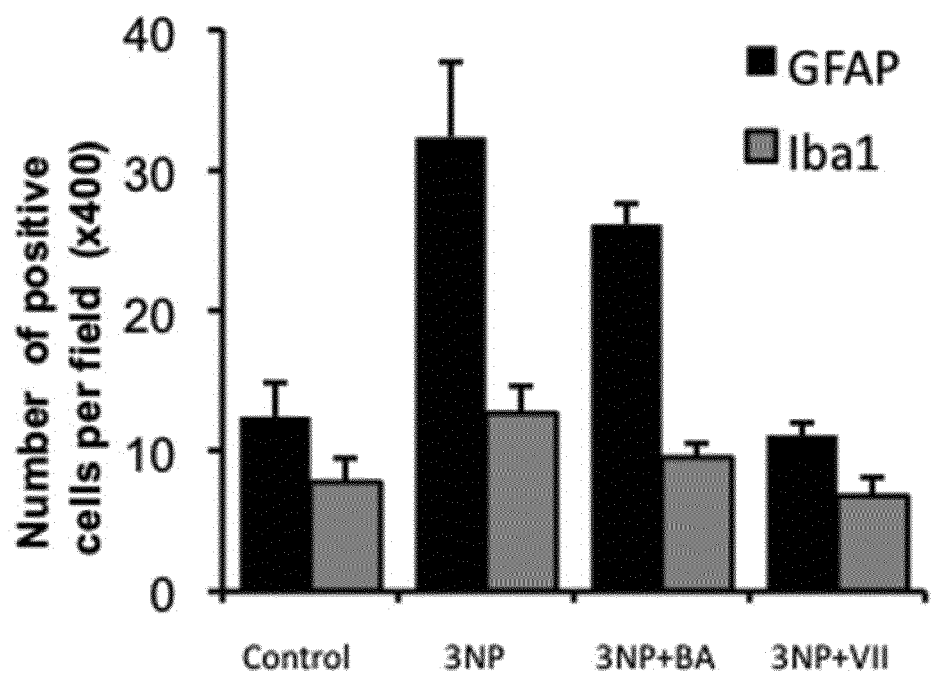

In addition, compound VII-mediated neuroprotection was associated with reduced 3NP-induced microgliosis and astrogliosis as determined by Iba1 and GFAP immunohistochemistry (FIG. 11). For this test, intoxicated mice with 3-Nitropropionic acid (3-NP) were used for determining microglia activation and astrogliosis including a Control with non-intoxicated mice (3NP, 3NP+BA and 3NP+Compound VII). Iba-1 and glial fibrillary acidic protein (GFAP) expression were determined by immunostaining of brain sections through the different group of mice. Quantification of the different markers was performed with Image J software. Total average number of microglia (Iba1$^+$) and astrocytes (GFAP$^+$) is shown in FIG. 11.

Figure 12:
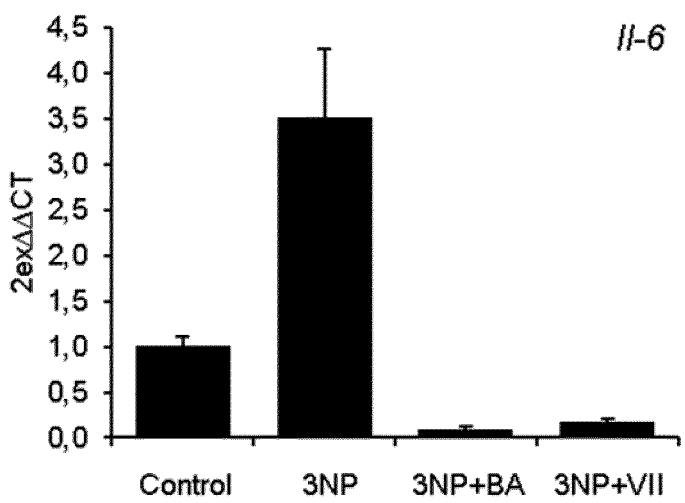
FIG. 12. Compound VII reduces the expression on inflammatory marker mRNAs in the striatum.
Gene expression of inflammatory markers including COX-2 (FIG. 12D), IL-1β (FIG. 12B), IL-6 (FIG. 12A) and iNOS (FIG. 12C), was down regulated in 3NP+compound VII (30 mg/kg) treated mice compared with 3NP+Vehicle mice. Betulinic acid (BA) treatment (30 mg/kg) also inhibited the expression of inflammatory markers. Expression levels were calculated using the $2^{-\Delta\Delta Ct}$ method. Values are expressed as means±SEM for 6 animals per group.
Figure 12:
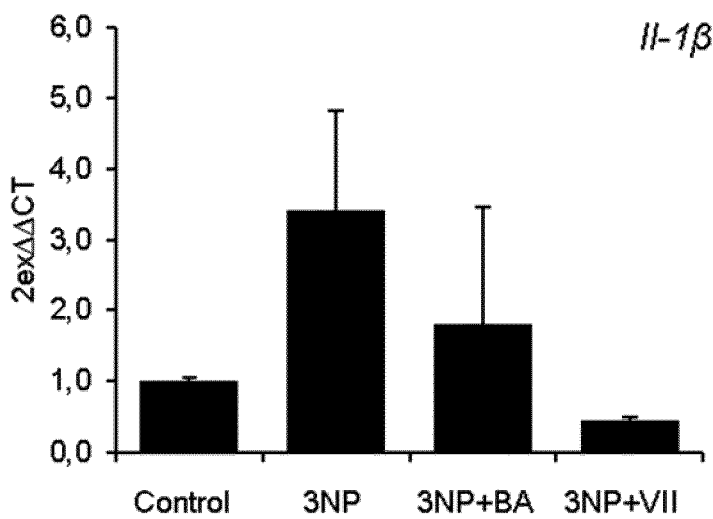
Figure 12:
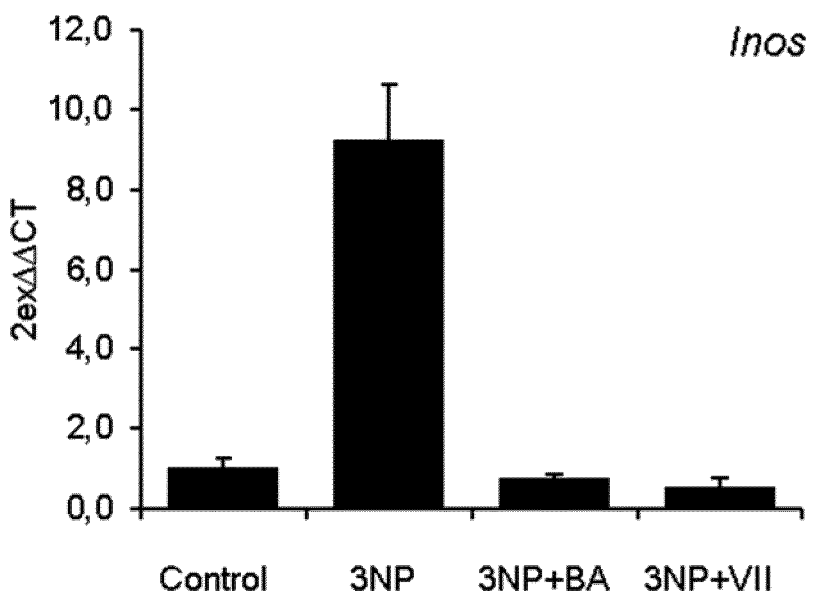
Figure 12:
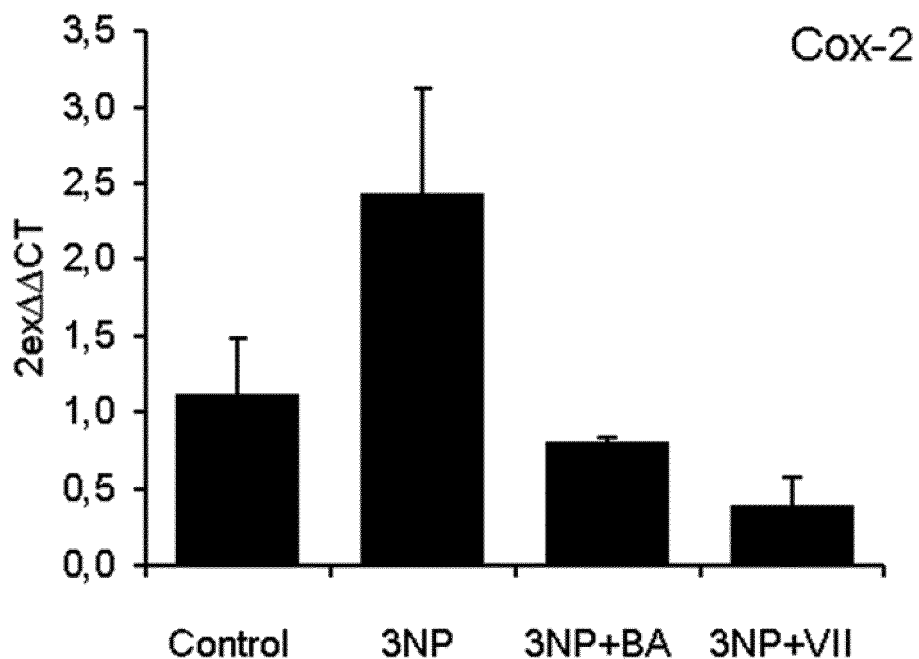

Finally, the expression of inflammatory enzymes COX-2 and iNOs was significantly up regulated in 3NP-lesioned mice in parallel to increased expression of proinflammatory cytokines IL-1β and IL-6. The mRNA expression for COX-2 (FIG. 12D), IL-1β (FIG. 12B), IL-6 (FIG. 12A) and iNOS (FIG. 12C), was down regulated in 3NP+compound VII (30 mg/kg) treated mice compared with 3NP+Vehicle mice. Betulinic acid (BA) treatment (30 mg/kg) also inhibited the expression of inflammatory markers (as shown in FIG. 12). Expression levels were calculated using the $2^{-\Delta\Delta Ct}$ method. Values are expressed as means±SEM for 6 animals per group Example 8. Real-Time Quantitative PCR Used in the Invention (Example 7)

Total RNA was isolated from striata (3NP model) using RNeasy Lipid Tissue Mini Kit (Qiagen, GmbH). The total amount of RNA extracted was quantitated by spectrometry at 260 nm and its purity from the ratio between the absorbance values at 260 and 280 nm. Genomic DNA was removed to eliminate DNA contamination. Single-stranded complementary DNA was synthesized from up to 1 µg of total RNA (pool from at least 3 animals per group) using iScript™ cDNA Synthesis Kit (Bio-Rad, Hercules, Calif., USA). The reaction mixture was kept frozen at −20° C. until enzymatic amplification. The iQ™ SYBR Green Supermix (Bio-Rad) was used to quantify mRNA levels for COX-2, IL-6, IL-1β, and iNOS. Real-time PCR was performed using a CFX96 Real-Time PCR Detection System (Bio-Rad). The GAPDH housekeeping gene was used to standardize the mRNA expression levels in every sample. Expression levels were calculated using the $2^{-\Delta\Delta Ct}$ method. Sequences of oligonucleotide primers are given in Table IV.

TABLE IV

List of mouse primer sequences used in quantitative Polymerase Chain Reaction.

| Gene | Forward | Reverse |
|---|---|---|
| IL-6 | 5'-GAACAACGATG ATGCACTTGC-3' | 5'-TCCAGGTAGCT ATGGTACTCC-3' |
| iNOS | 5'-AACGGAGAAC GTTGGATTTG-3' | 5'-CAGCACAAGG GGTTTTCTTC-3' |
| COX-2 | 5'-TGAGCAACTAT TCCAAACCAGC-3' | 5'-GCACGTAGTCTT CGATCACTATC-3' |
| IL-I β | 5'-CTCCACCTCA ATGGACAGAA-3' | 5'-GCCGTCTTTC ATTACACAGG-3' |
| GAPDH | 5'-TGGCAAAGTGG AGATTGTTGCC-3' | 5'-AAGATGGTGAT GGGCTTCCCG-3' |

The present results substantiate the therapeutic use of the compounds described in the present inventions, for the clinical management of conditions and diseases the treatment of which is responsive to HIF activation such as stroke, cerebral palsy, traumatic injuries, neurodegenerative diseases such as Multiple Sclerosis, Huntington disease, Alzheimer disease and Parkinson disease, IBD, myocardial ischaemia-reperfusion injury, acute lung injury, organ transplantation, acute kidney injury and arterial diseases.

Example 9. Effect of Compound VII on a High Fat Diet (HFD) Model of Diabetes and Metabolic Pathologies High-fat diet-fed mouse is a widely used model for impaired glucose tolerance (IGT) and type 2 diabetes. Eight-week-old male C57BL/6 mice (Charles River-France) were used for experiments. Mice were maintained under controlled conditions [12 h light/dark cycle; temperature 20° C. (±2° C.) and 40-50% relative humidity] with free access to tap water and standard rodent chow ad libitum. After 1 week of acclimatization, mice were divided into two groups and fed ad libitum with a standard diet—CD- (Code U8220G10R, SAFE Diets, Augy, France) or a High-Fat diet—HFD- (D12451; Research Diets, New Brunswick, N.J.) in order to induce obesity for 15 weeks (diet-induced obesity, DIO). In order to assess the potential beneficial metabolic effects of compound VII in this model of DIO, pharmacological administration of the compound (30 mg/kg body weight) was performed by intraperitoneal (i.p.) injection every 24 h from $12^{th}$ to $15^{th}$ week of diet exposure. Control animals received the corresponding vehicle injections (1:1:18 Ethanol:Cremophor:Saline).

To ensure the effectiveness of HFD feeding regimen and assess the efficacy of compounds in terms of amelioration of the metabolic phenotype, body composition analyses of fat and lean masses were performed by QMR (quantitative magnetic resonance) using the EchoMRI™ 700 analyzer (Houston, Tex., software v. 2.0). In this sense, MRI scans were taken in three time points during the experimental period: before starting diet exposure, after 12 week of feeding regimen (coinciding with start of treatment) and at the end of experimental procedures (on the 15$^{th}$ week of diet exposure). Additionally, five days before sacrifice, glucose tolerance test (GTT) was performed in overnight food-deprived mice. To this end, mice were injected intraperitoneally with 2 mg of glucose/g body weight and blood glucose was measured before and 30, 60 and 120 min after injection utilizing an Accu-Chek Advantage® (Roche) glucometer. At the end of the experiment, mice were sacrificed and blood samples were collected using EDTA-coated tubes and plasma stored at −80° C. Plasma triglycerides were measured using and enzymatic colorimetric kit (QCA, Barcelona, Spain).

Figure 13:
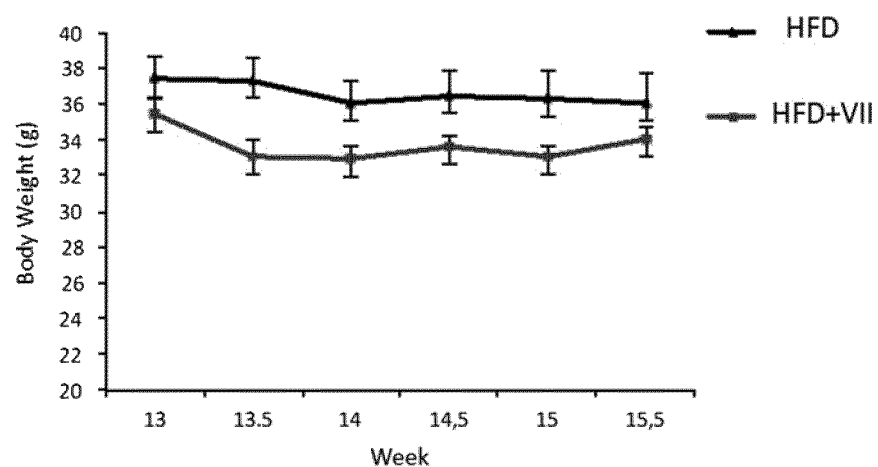
FIG. 13. Effect of compound VII on body weight, fat mass and adiposity in mice subjected to high fat diet (HFD animals).
Mice were fed with HFD for 13 weeks and the treated daily with compound VII (30 mg/Kg) for 21 days and the effect on body weight was monitored every 3-4 days (FIG. 13A). % Lean mass (FIG. 13B) is calculated as the proportion of entire weight of the body without the proportion due to fat. % Fat mass (FIG. 13C) is calculated as the proportion of fat to the total body weight. Fat mass and the percentage of adiposity was calculated at the week 15. Body composition was assessed by Magnetic Resonance Imaging (MRI). Values are expressed as means±SEM for 10 animals per group.
Figure 13:
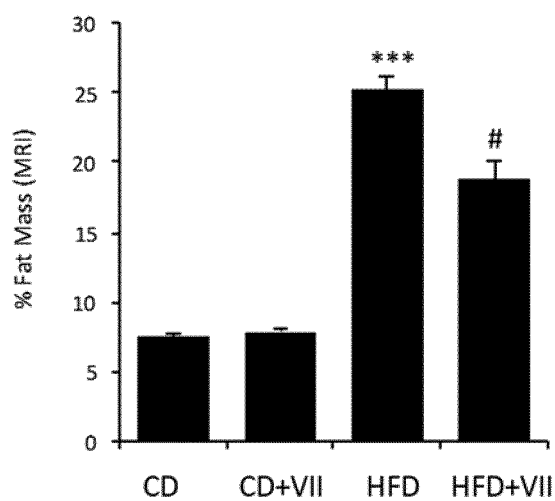
Figure 13:
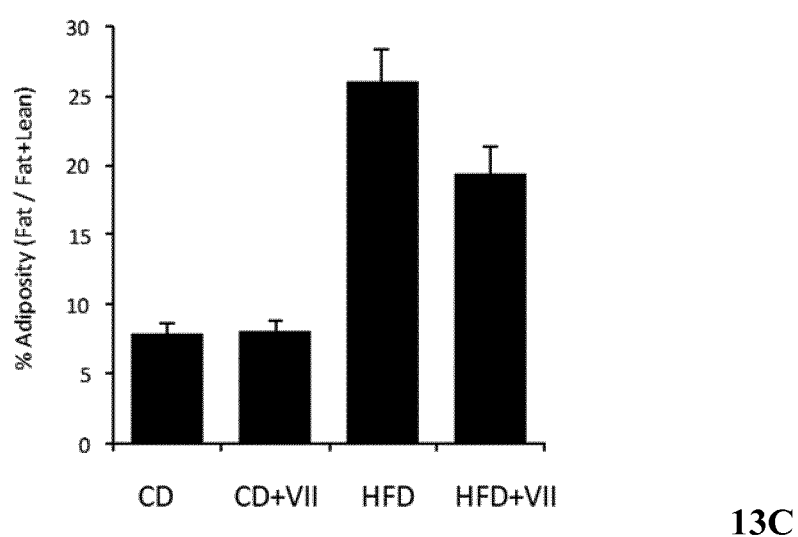
Figure 14:
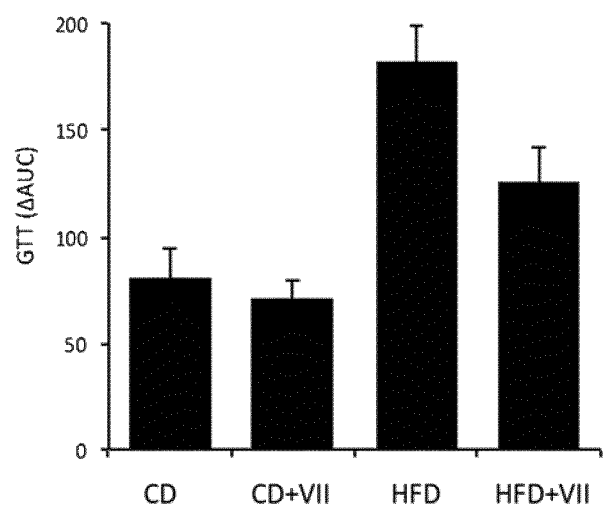
FIG. 14. Compound VII improves glucose tolerance (GTT) in HFD animals.
GTT of the HFD-fed mice after the 3-week vehicle (Control, CD) or compound VII administration (30 mg/Kg). The sum of the trapezoidal areas between the 0, 15, 30, 45, 60, 90 and 120 min time points corresponding to each animal were summed to obtain the area under the curve (AUC). The relative area values are expressed as a percentage relative to the average AUC of the vehicle cohort, which is defined as 100%. Values are expressed as mean±S.E.M (n=6).
Figure 15:
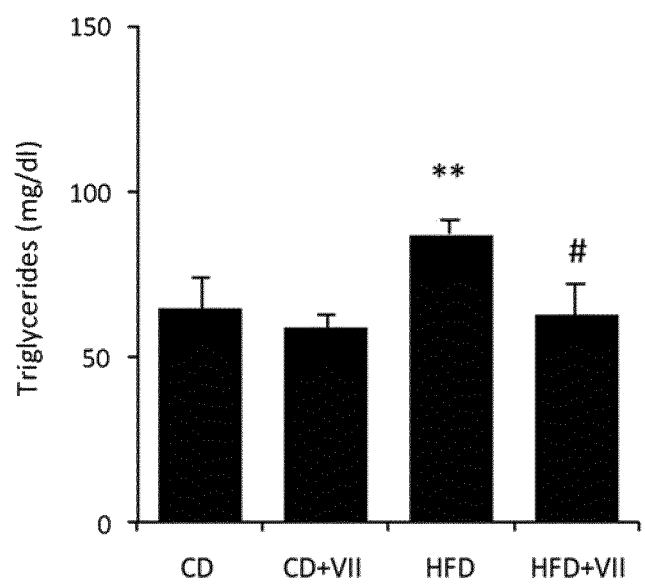
FIG. 15. Compound VII prevents hypertriglyceridemia in HFD animals.
Plasma triglycerides levels in control and HFD-fed mice after the 3-week vehicle (Control, CD) or compound VII administration (30 mg/Kg). Values are expressed as mean±S.E.M (n=6).

We found that compound VII alleviated weight gain (FIG. 13A), increase in Fat Mass (FIG. 13B) and adiposity (FIG. 13C). Moreover, compound VII improved glucose tolerance (FIG. 14) and normalize the plasma levels of triglycerides (FIG. 15) in HFD mice. Our results are in agreement with previous report showing that PDH inhibitors improves glucose and lipid metabolism in murine models of obesity and diabetes induced by HFD (Rahtu-Korpela et al., Diabetes. 2014 October; 63(10):3324-33). Therefore, said results indicate that the compounds of the invention are useful in the treatment of diabetes or other related metabolic pathologies such as hypertriglyceridemia.

The invention claimed is:

1. A triterpene derivative of Formula (Ia) or stereoisomers, pharmaceutically acceptable salts or pharmaceutically acceptable solvates thereof,

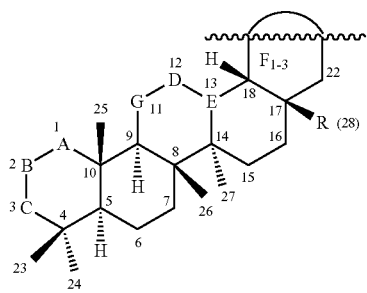

Formula (Ia)

wherein independently,

A-B is a single carbon-carbon bond or a double carbon-carbon bond;

B is a methylene (—$CH_2$—), an olefin methine (=CH—), a hydroxymethine [—CH(OH)—], or a hydroxylated olefin carbon [—C(OH)=];

B-C is a single carbon-carbon bond or a double carbon-carbon bond; or is part of a heterocyclic ring comprising one or more heteroatoms wherein at least one of said heteroatoms is nitrogen; and wherein said heterocyclic ring is a five-membered ring comprising one nitrogen and one oxygen;

C is a hydroxymethine [—CH(OH)—], an acyloxymethine [—CH(OCOR')—], an olefin methine (=CH—), a carbonyl [—C(=O)—], an oxime [—C(=N—OH)—] or an hydrazone [—C(=N—$NH_2$)—], wherein R' is methyl;

D-E is a single or a double carbon-carbon bond;
F is $F_{1a}$, $F_{2a}$ or $F_{3a}$;

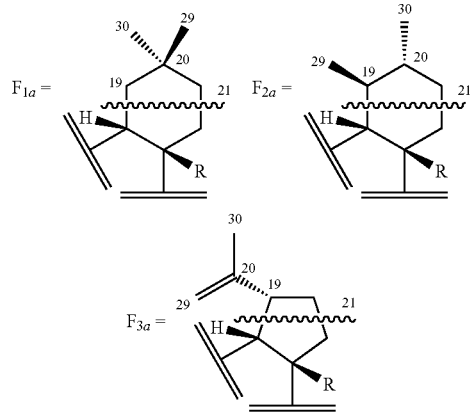

G is a methylene (—CH$_2$—) or a carbonyl [—C(=O)—]; and

R is a hydroxamate group (—CONHOH);

and wherein, when C is an acyloxymethine [—CH(OCOR')—], the triterpene derivative of Formula (Ia) is

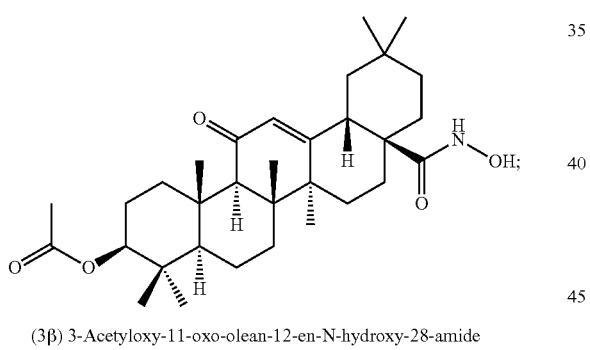

(3β) 3-Acetyloxy-11-oxo-olean-12-en-N-hydroxy-28-amide when B is a methylene (—CH$_2$—), C is a hydroxymethine [—CH(OH)—], D-E is a double carbon-carbon bond, G is a methylene (—CH$_2$—) and R is a hydroxamate (—CONHOH), F is $F_{3a}$;

when B is a methylene (—CH$_2$—), C is a hydroxymethine [—CH(OH)—], D-E is a single carbon-carbon bond, G is a methylene (—CH$_2$—) and R is a hydroxamate (—CONHOH), F is $F_{1a}$ or $F_{2a}$;

when B is a methylene (—CH$_2$—), C is an oxime [—C(=N—OH)—], D-E is a double carbon-carbon bond, G is a methylene (—CH$_2$—) and R is a hydroxamate (—CONHOH), F is $F_{1a}$ or $F_{3a}$.

2. The triterpene derivative according to claim 1, wherein said triterpene derivative is selected from the group consisting of:

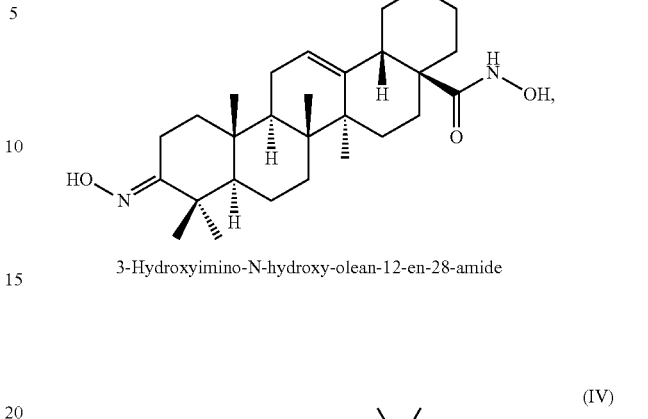

3-Hydroxyimino-N-hydroxy-olean-12-en-28-amide

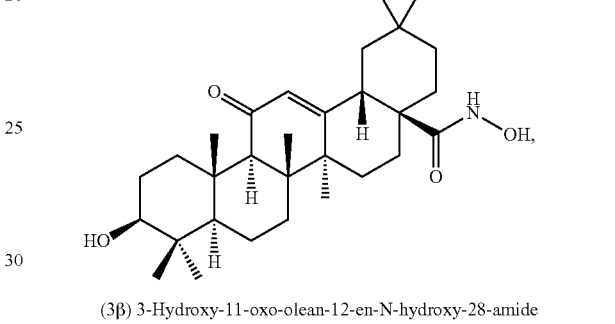

(3β) 3-Hydroxy-11-oxo-olean-12-en-N-hydroxy-28-amide

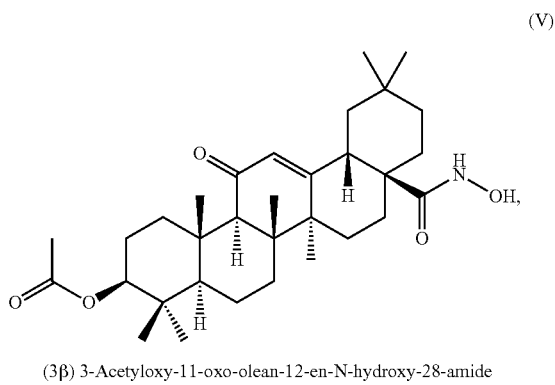

(3β) 3-Acetyloxy-11-oxo-olean-12-en-N-hydroxy-28-amide

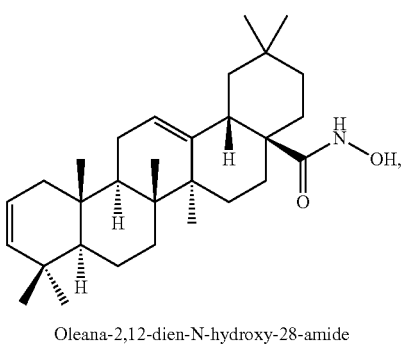

Oleana-2,12-dien-N-hydroxy-28-amide

-continued

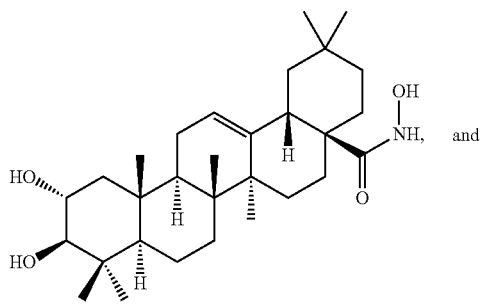

(2α,3β) 2,3-Dihydroxy-N-hydroxy-olean-12-en-28-amide

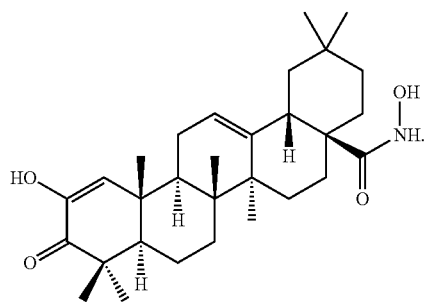

2-Hydroxy-3-oxo-oleana-1,12-dien-N-hydroxy-28-amide

3. A compound selected from the group consisting of XVIII and XIX:

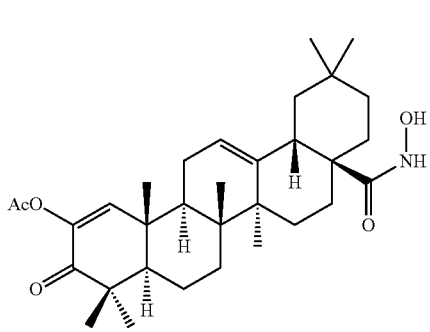

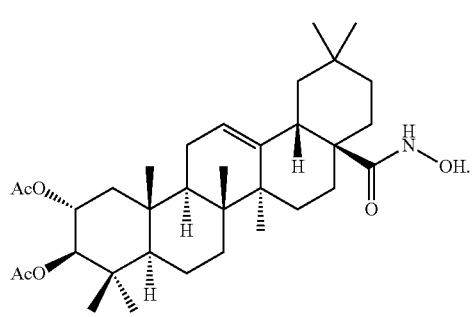

4. A pharmaceutical composition comprising at least one triterpene derivative of Formula (Ia) of claim 1 as a first active ingredient and at least one excipient or carrier.

5. A method of treating a condition or disease responsive to the activation of a HIF pathway, wherein the method comprises administering to a subject in need thereof a therapeutically effective amount of the triterpene derivative of claim 1.

6. The method of claim 5, wherein the condition or disease responsive to the activation of the HIF pathway is selected from the group consisting of stroke, cerebral palsy, traumatic injuries and neurodegenerative diseases.

7. The method of claim 5, wherein the condition or disease responsive to the activation of the HIF pathway is selected from the group consisting of IBD, myocardial ischaemia-reperfusion injury, acute lung injury, diabetic and chronic wounds, organ transplantation, acute kidney injury and arterial diseases.

8. The method of claim 5, wherein the condition or disease responsive to the activation of the HIF pathway is diabetes, hyperlipidemia or hypertriglyceridemia.

9. The method, according to claim 5, wherein said method produces an increase in the erythropoietin plasma levels.

10. A method of treating a condition or disease wherein the treatment of said condition or disease benefits from HIF-1α or HIF-2α activation, the method comprising administering to a subject in need thereof a triterpene derivative of Formula (I) or, stereoisomers, pharmaceutically acceptable salts or pharmaceutically acceptable solvates thereof, Formula (I)

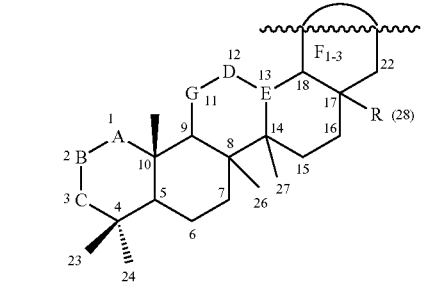

wherein independently,

A-B is a single carbon-carbon bond or a double carbon-carbon bond;

B is a methylene (—CH$_2$—), an olefin methine (=CH—), a hydroxymethine [—CH(OH)—], or a hydroxylated olefin carbon [—C(OH)=];

B-C is a single carbon-carbon bond or a double carbon-carbon bond; or is part of a heterocyclic ring comprising one or more heteroatoms wherein at least one of said heteroatoms is nitrogen; and wherein said heterocyclic ring is a five membered ring comprising one nitrogen and one oxygen;

C is a hydroxymethine [—CH(OH)—], an acyloxymethine [—CH(OCOR')—], an olefin methine (=CH—), a carbonyl [—C(=O)—], an oxime [—C(=N—OH)—] or an hydrazone [—C(=N—NH$_2$)—], wherein R' is methyl;

D-E is a single or a double carbon-carbon bond;

F is F$_1$, F$_2$ or F$_3$;

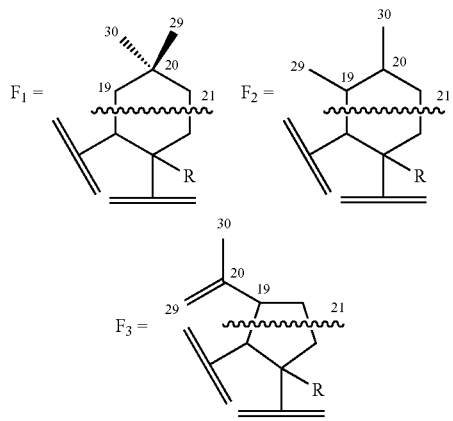

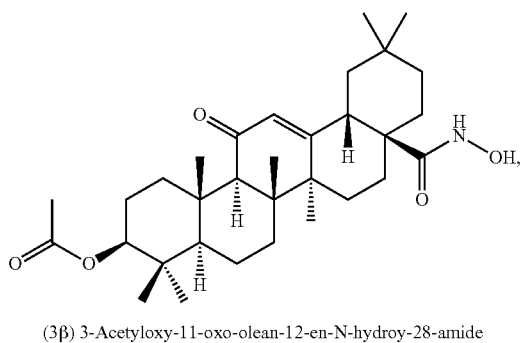

(3β) 3-Acetyloxy-11-oxo-olean-12-en-N-hydroy-28-amide

G is a methylene (—CH₂—) or a carbonyl [—C(=O)—]; and

R is a hydroxamate group (—CONHOH).

11. The method according to claim 10, wherein said triterpene derivative is selected from the group consisting of:

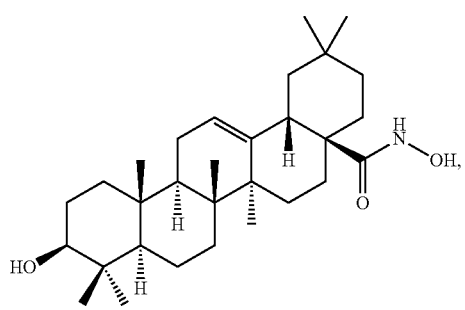

(3β) 3-Hydroxy-N-hydroxy-olean-12-en-28-amide

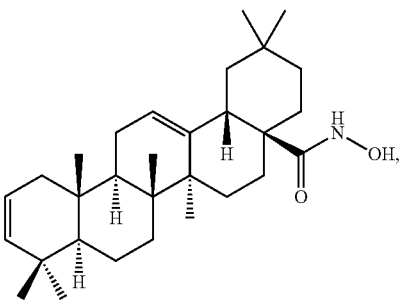

Oleana-2,12-dien-N-hydroxy-28-amide

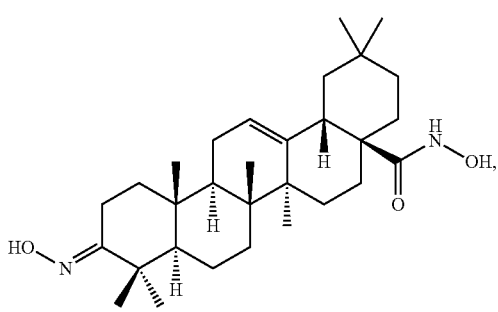

3-Hydroxyimino-N-hydroxy-olean-12-en-28-amide

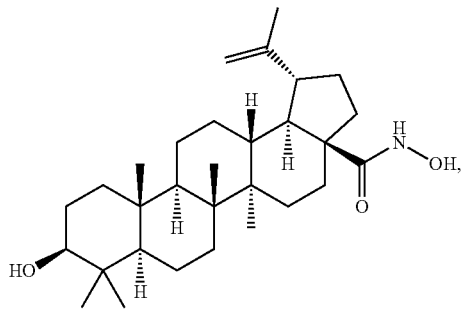

(3β) 3-Hydroxy-N-hydroxy-lup-20(29)-en-28-amide

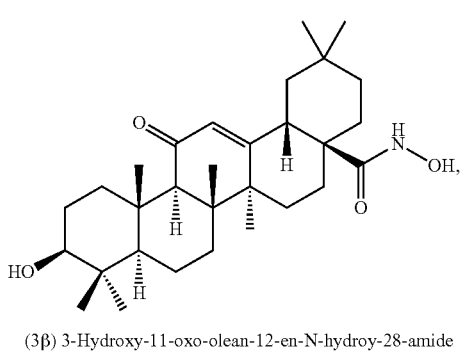

(3β) 3-Hydroxy-11-oxo-olean-12-en-N-hydroy-28-amide

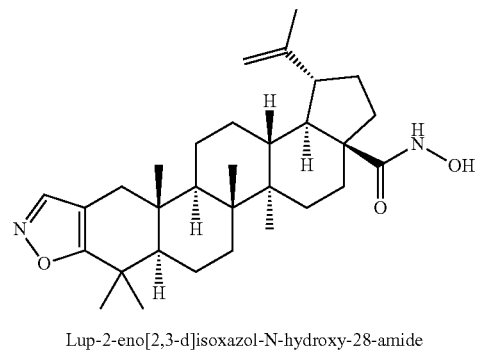

Lup-2-eno[2,3-d]isoxazol-N-hydroxy-28-amide

-continued

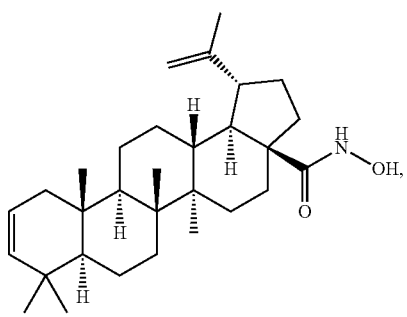

Lupa-2,20(29)-dien-N-hydroxy-28-amide (X)

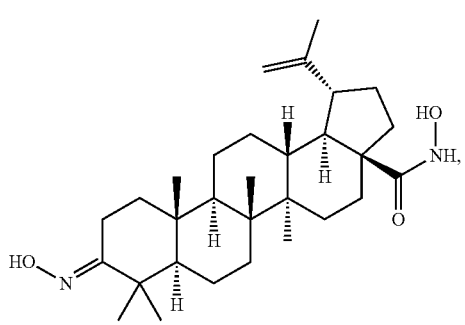

3-Hydroxyimino-N-hydroxy-lup-20(29)-en-28-amide (XI)

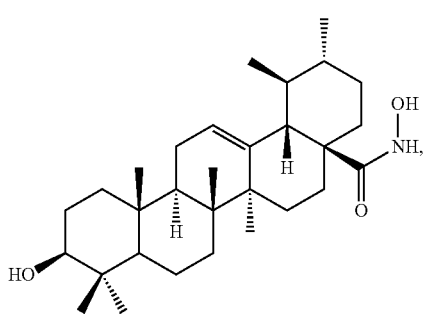

(3β) 3-Hydroxy-N-hydroxy-urs-12-en-28-amide (XII)

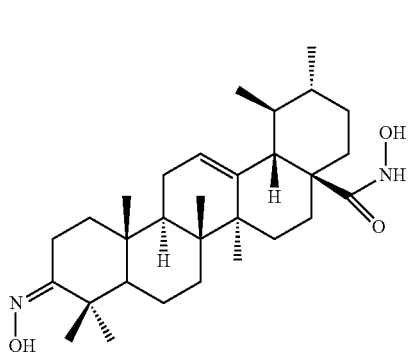

3-Hydroxyimino-N-hydroxy-urs-12-en-28-amide (XIII)

-continued

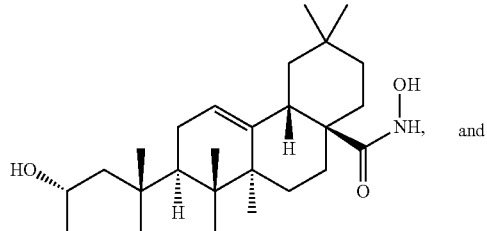

(2α,3β) 2,3-Dihydroxy-N-hydroxy-olean-12-en-28-amide (XIV)

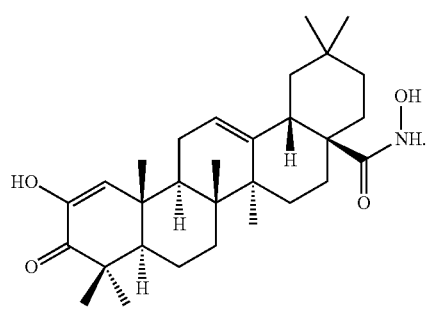

2-Hydroxy-3-oxo-oleana-1,12-dien-N-hydroxy-28-amide (XV)

12. The method of claim 10, wherein said condition or disease is selected from the group consisting of stroke, cerebral palsy, traumatic injuries and neurodegenerative diseases.

13. The method of claim 10, wherein said condition or disease is selected from the group consisting of IBD, myocardial ischaemia-reperfusion injury, acute lung injury, diabetic and chronic wounds, organ transplantation, acute kidney injury and arterial diseases.

14. The method of claim 10, wherein the condition or disease is diabetes, hyperlipidemia or hypertriglyceridemia.

15. The method according to claim 10, wherein said method produces an increase in the erythropoietin plasma levels.

16. The method of claim 10, wherein said triterpene derivative of Formula (I) is a triterpene derivative of Formula (Ib):

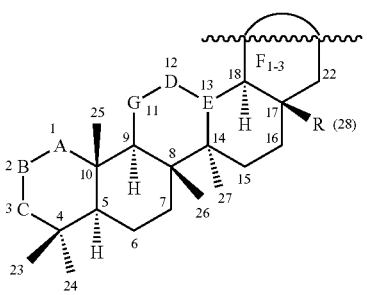

Formula (Ib)

17. The method according to claim 15, wherein said triterpene derivative is selected from (II), (III), (IV), (V), (VI), (VII), (VIII), (X), (XI), (XII), (XIII), (XIV) or (XV):

(II)
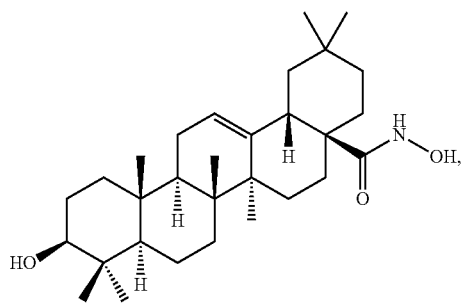
(3β) 3-Hydroxy-N-hydroxy-olean-12-en-28-amide
(III)
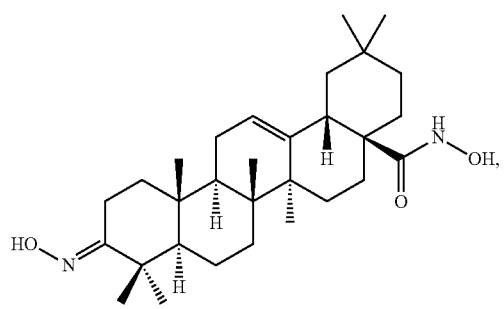
3-Hydroxyimino-N-hydroxy-olean-12-en-28-amide
(IV)
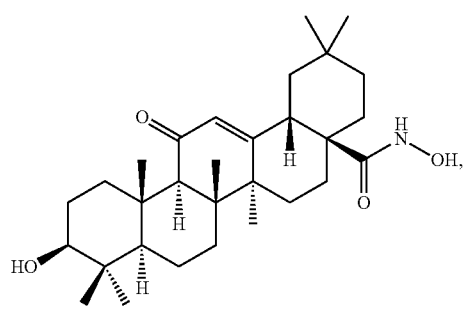
(3β) 3-Hydroxy-11-oxo-olean-12-en-N-hydroy-28-amide
(V)
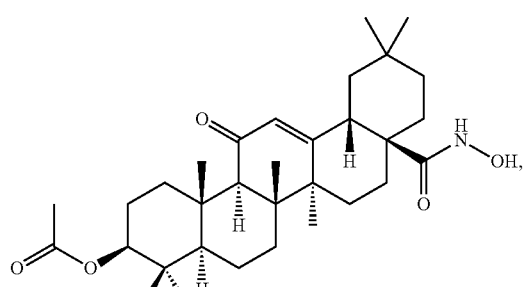
(3β) 3-Acetyloxy-11-oxo-olean-12-en-N-hydroy-28-amide
(VI)
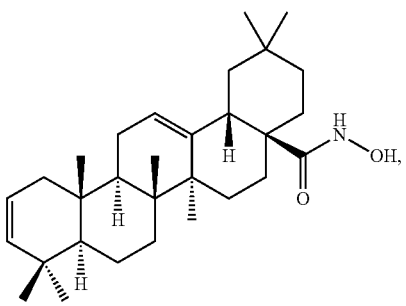
Oleana-2,12-dien-N-hydroxy-28-amide
(VII)
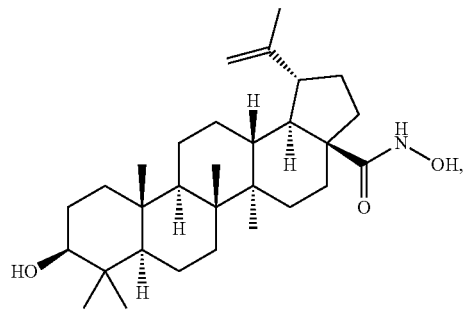
(3β) 3-Hydroxy-N-hydroxy-lup-20(29)-en-28-amide
(VIII)
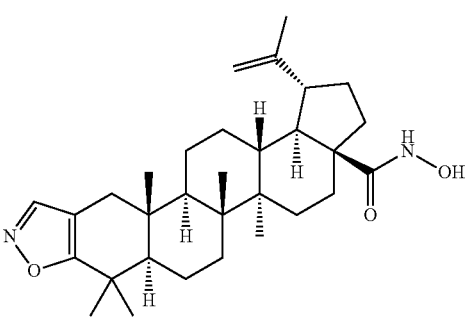
Lup-2-eno[2,3-d]isoxazol-N-hydroxy-28-amide
(X)
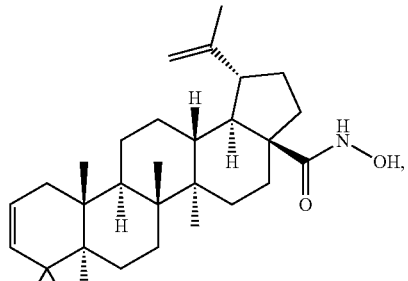
Lupa-2,20(29)-dien-N-hydroxy-28-amide

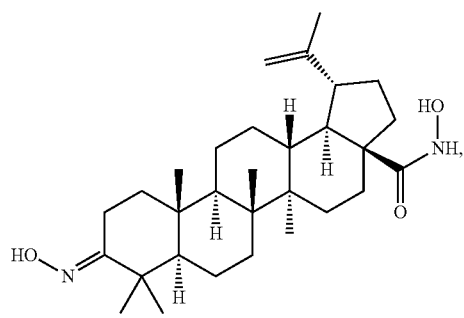
(XI) 3-Hydroxyimino-N-hydroxy-lup-20(29)-en-28-amide
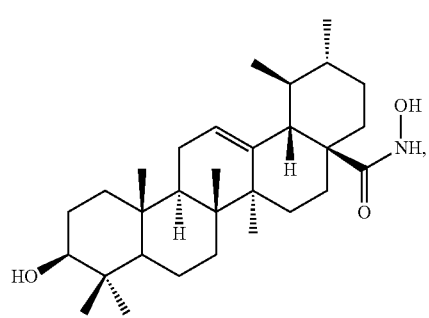
(XII) (3β) 3-Hydroxy-N-hydroxy-urs-12-en-28-amide
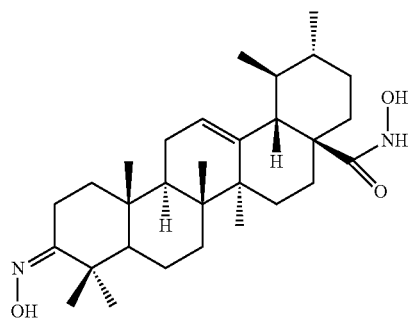
(XIII) 3-Hydroxyimino-N-hydroxy-urs-12-en-28-amide
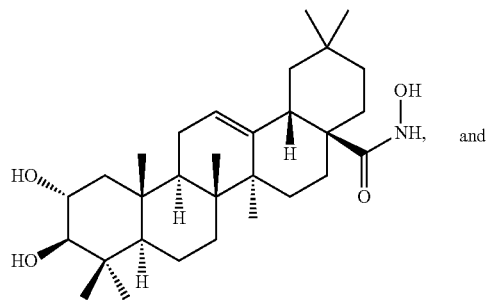
(XIV) (2α,3β) 2,3-Dihydroxy-N-hydroxy-olean-12-en-28-amide
and
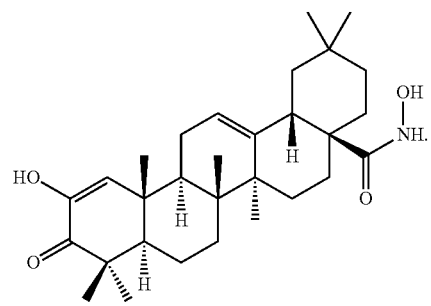
(XV) 2-Hydroxy-3-oxo-oleana-1,12-dien-N-hydroxy-28-amide
* * * * *

UNITED STATES PATENT AND TRADEMARK OFFICE
CERTIFICATE OF CORRECTION

PATENT NO. : 10,766,855 B2
APPLICATION NO. : 16/099800
DATED : September 8, 2020
INVENTOR(S) : Blanco et al.

It is certified that error appears in the above-identified patent and that said Letters Patent is hereby corrected as shown below:

On the Title Page

Item (71) Applicants:
VIVACELL BIOTECHNOLOGY ESPANA S.L., Cordova
Should read:
VIVACELL BIOTECHNOLOGY ESPAÑA S.L., Córdoba Item (72) Inventors:
Eduardo Munoz Blanco, Cordova
Maria Luz Bellido Cabello De Aba, Cordova
Should read:
Eduardo Munoz Blanco, Cordoba
Maria Luz Bellido Cabello De Aba, Cordoba Item (73) Assignee:
VIVACELL BIOTECHNOLOGY ESPAÑA S.L., Cordova
Should read:
VIVACELL BIOTECHNOLOGY ESPAÑA S.L., Córdoba Signed and Sealed this
Fourth Day of October, 2022

Katherine Kelly Vidal
*Director of the United States Patent and Trademark Office*

```
                            SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: IL-6 primer Forward

<400> SEQUENCE: 1
gaacaacgat gatgcacttg c                                                  21

<210> SEQ ID NO 2
<211> LENGTH: 21
<212> TYPE: DNA
<213> ORGANISM: Artificial Sequence
<220> FEATURE:
<223> OTHER INFORMATION: IL-6 primer Reverse

<400> SEQUENCE: 2
tccaggtagc tatggtactc c                                                  21

<210> SEQ ID NO 3
<211> LENGTH: 20
<212> TYPE: DNA
<213> ORGANISM: Artificial Sequence
<220> FEATURE:
<223> OTHER INFORMATION: iNOS primer Forward

<400> SEQUENCE: 3
aacggagaac gttggatttg                                                    20

<210> SEQ ID NO 4
<211> LENGTH: 20
<212> TYPE: DNA
<213> ORGANISM: Artificial Sequence
<220> FEATURE:
<223> OTHER INFORMATION: iNOS primer Reverse

<400> SEQUENCE: 4
cagcacaagg ggttttcttc                                                    20

<210> SEQ ID NO 5
<211> LENGTH: 22
<212> TYPE: DNA
<213> ORGANISM: Artificial Sequence
<220> FEATURE:
<223> OTHER INFORMATION: COX-2 primer Forward

<400> SEQUENCE: 5
tgagcaacta ttccaaacca gc                                                 22
```

```
<210> SEQ ID NO 6
<211> LENGTH: 23
<212> TYPE: DNA
<213> ORGANISM: Artificial Sequence
<220> FEATURE:
<223> OTHER INFORMATION: COX-2 primer Reverse

<400> SEQUENCE: 6
gcacgtagtc ttcgatcact atc                                              23

<210> SEQ ID NO 7
<211> LENGTH: 20
<212> TYPE: DNA
<213> ORGANISM: Artificial Sequence
<220> FEATURE:
<223> OTHER INFORMATION: IL-1Beta primer Forward

<400> SEQUENCE: 7
ctccacctca atggacagaa                                                  20

<210> SEQ ID NO 8
<211> LENGTH: 20
<212> TYPE: DNA
<213> ORGANISM: Artificial Sequence
<220> FEATURE:
<223> OTHER INFORMATION: IL-1Beta primer Reverse

<400> SEQUENCE: 8
gccgtctttc attacacagg                                                  20

<210> SEQ ID NO 9
<211> LENGTH: 22
<212> TYPE: DNA
<213> ORGANISM: Artificial Sequence
<220> FEATURE:
<223> OTHER INFORMATION: GAPDH primer Forward

<400> SEQUENCE: 9
tggcaaagtg gagattgttg cc                                               22

<210> SEQ ID NO 10
<211> LENGTH: 21
<212> TYPE: DNA
<213> ORGANISM: Artificial Sequence
<220> FEATURE:
<223> OTHER INFORMATION: GAPDH primer Reverse

<400> SEQUENCE: 10
aagatggtga tgggcttccc g                                                21
```